(12) United States Patent
Hilden et al.

(10) Patent No.: US 8,361,469 B2
(45) Date of Patent: Jan. 29, 2013

(54) ANTIBODIES AGAINST TISSUE FACTOR PATHWAY INHIBITOR

(75) Inventors: Ida Hilden, Vanløse (DK); Berit Olsen Krogh, Rødovre (DK); Jes Thorn Clausen, Hoeng (DK); Ole Hvilsted Olsen, Brønshøj (DK); Jens Breinholt, Dyssegård (DK); Brian Lauritzen, Herlev (DK); Brit Binow Sørensen, Birkerød (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 13/140,296

(22) PCT Filed: Dec. 18, 2009

(86) PCT No.: PCT/EP2009/067598
§ 371 (c)(1),
(2), (4) Date: Aug. 30, 2011

(87) PCT Pub. No.: WO2010/072691
PCT Pub. Date: Jul. 1, 2010

(65) Prior Publication Data
US 2011/0318356 A1 Dec. 29, 2011

Related U.S. Application Data

(60) Provisional application No. 61/203,479, filed on Dec. 23, 2008.

(30) Foreign Application Priority Data

Dec. 22, 2008 (EP) .................................... 08172520

(51) Int. Cl.
*A61K 39/395* (2006.01)
(52) U.S. Cl. ............... 424/145.1; 424/133.1; 424/139.1; 424/141.1; 514/14.5; 514/14.9

(58) Field of Classification Search .................. None
See application file for complete search history.

(56) References Cited

U.S. PATENT DOCUMENTS

| | | | | |
|---|---|---|---|---|
| 5,902,582 A | * | 5/1999 | Hung | 424/130.1 |
| 6,656,746 B2 | * | 12/2003 | Sprecher et al. | 436/547 |
| 7,015,746 B1 | * | 3/2006 | Martinez et al. | 327/543 |
| 2010/0173847 A1 | * | 7/2010 | Dockal et al. | 514/13 |
| 2012/0108796 A1 | * | 5/2012 | Wang et al. | 530/388.15 |

FOREIGN PATENT DOCUMENTS

| | | | |
|---|---|---|---|
| JP | 06153985 A | * | 6/1994 |
| WO | WO 92/07584 | | 5/1992 |
| WO | WO 2010/017196 | | 2/2010 |

OTHER PUBLICATIONS

Tiemann et al. Eur J Clin Chem Clin Biochem. Nov. 1997;35(11):855-60.*
Campbell A.M., Monoclonal Antibody Technology, Elsevier Science Publishing company Inc., 1984, pp. 1-32.*
Zillmann et al., Biochemical and Biophysical Research Communications, 2001, vol. 281, No. 2, pp. 603-609.
Welsch, et al., Thrombosis Research, 1991, vol. 64, No. 2, pp. 213-222.
Engelmann, Blood, American Society of Hematology, 2004, vol. 104, No. 11, p. 78B.
Erhardtsen et al., Blood Coagulation and Fibrinolysis, 1995, vol. 6, No. 5, p. 388-394.
Brinkmann et al., European Journal of Clinical Chemistry and Clinical Biochemistry, 1994, vol. 32, No. 4, pp. 313-317.
R&D Systems: R&D Systems New Products—Jun. 2007.

* cited by examiner

*Primary Examiner* — Michael Szperka
(74) *Attorney, Agent, or Firm* — Michael J. Brignati

(57) ABSTRACT

The invention relates to antibodies that specifically bind to tissue factor pathway inhibitor (TFPI) and that reduce the clotting time of blood. Such antibodies have utility in the treatment of subjects with a coagulopathy.

4 Claims, 24 Drawing Sheets

Figure 1

```
A. Heavy Chain
          1            2          3            4             5              6
         12345678901234567890123456789012345AB67890123456789012ABC34567890      <- Kabat
         EVQLVESGGGLVKPGGSLKLSCAASGTFSNYAMS   WVRQAPKKLEWVATISR   SGSYSYPP      TFPI4F36
         ************************* ********* ****** *****  ****  ******
         EVQLVESGGGLVKPGGSLRLSCAASGTFSSYSMN   WVRQAPGKGLEWVSSISS  SSSYIYYA      VH3_21/JH6
         EVQLVESGGGLVKPGGSLRLSCAASGTFSNYAMS   WVRQAPGKGLEWVSTISR  SGSYSYYA      hz4F36CDRgraft 7         8           9            10                11
         12345678901234567890123ABC345678901234567890ABCDEFGHIJK1234567890
         DSVQGRFTISRDNAKNTLYLQMSSLRSEDTAMYYCRLGGYDEGD          AMDSWGQGTSVTVSS
         *** ***************  *****    ***** ***                *** ** ******
         DSVKGRFTISRDNAKNSLYLQMNSLYAEDTAVYYCAR                 MDVWGQGTTVTVSS
         DSVKGRFTISRDNAKNSLYLQMNSLRAEDTAVYYCARLGGYDEGD         AMDSWGQGTTVTVSS B. Light Chain
          1            2           3         4            5               6
         1234567890123ABCDEF78901234567ABCDEF8901234567890123456789012345AB67890     <- Kabat
         DIVMTQTPLHLSVTPGQPASISCKSSQSLLHS DGKTYLNWLLQRPGESPKLLIYLVSILDSGVPD  TFPI4F36
         ************* ***************** ************ *** ** ** ** *****
         DIVMTQTPLSLSVTPGQPASISCKSSQSLLES DGKTYLNWYLQKPGQSPQLLIYEVSSRFSGVPD  VKII_A18/JK4
         DIVMTQTPLSLSVTPGQPASISCKSSQSLLES DGKTYLNWYLQKPGQSPQLLIYLVSILDSGVPD  hz4F36CDRgraft 7          8              9          10
         123456789012345678901234567890123AB678901234567890
         RFSGSGSGTDFTLKISRVEAEDVGVYYCLQATHFP   QTFGGGTKLEIKR
         *** ***************    *   *****      ** *********
         RFSGSGSGTDFTLKISRVEAEDVGVYYCMQGIHLP   TFGGGTKVEIKR
         RFSGSGSGTDFTLKISRVEAEDVGVYYCLQATHFP   QTFGGGTKVEIKR
```

TFPI-4F36A1B2 VL (nucleotide and translated sequence, signal peptide omitted):

```
            D   I   V   M   T   Q   T   P   L   T   L   S   V   T   I   G   Q ·
      1   GATATTGTGA TGACCCAGAC TCCACTCACT TTGTCGGTTA CCATTGGACA
          CTATAACACT ACTGGGTCTG AGGTGAGTGA AACAGCCAAT GGTAACCTGT
          · P   A   S   I   S   C   K   S   S   Q   S   L   L   E   S   D   G ·
     51   ACCAGCTTCC ATCTCTTGCA AGTCAAGTCA GAGCCTCTTA GAAAGTGATG
          TGGTCGAAGG TAGAGAACGT TCAGTTCAGT CTCGGAGAAT CTTTCACTAC
          · K   T   Y   L   N   W   L   L   Q   R   P   G   E   S   P   K
    101   GAAAAACCTA TTTAAATTGG TTATTACAGA GGCCAGGCGA GTCTCCAAAG
          CTTTTTGGAT AAATTTAACC AATAATGTCT CCGGTCCGCT CAGAGGTTTC
            L   L   I   Y   L   V   S   I   L   D   S   G   V   P   D   R   F ·
    151   CTCCTAATCT ATCTGGTGTC TATACTGGAC TCTGGAGTCC CTGACAGGTT
          GAGGATTAGA TAGACCACAG ATATGACCTG AGACCTCAGG GACTGTCCAA
          · T   G   S   G   S   G   T   D   F   T   L   K   I   S   R   V   E ·
    201   CACTGGCAGT GGATCAGGGA CAGATTTCAC GCTGAAAATC AGCAGAGTGG
          GTGACCGTCA CCTAGTCCCT GTCTAAAGTG CGACTTTTAG TCGTCTCACC
          · A   E   D   L   G   V   Y   Y   C   L   Q   A   T   H   F   P
    251   AGGCTGAGGA TTTGGGAGTT TATTATTGTT TGCAAGCTAC ACATTTTCCT
          TCCGACTCCT AAACCCTCAA ATAATAACAA ACGTTCGATG TGTAAAAGGA
            Q   T   F   G   G   G   T   K   L   E   I   K   R
    301   CAGACGTTCG GTGGCGGCAC CAAGCTGGAA ATCAAACGG
          GTCTGCAAGC CACCGCCGTG GTTCGACCTT TAGTTTGCC
```

B

TFPI-4F36A1B2 VH (nucleotide and translated sequence, signal peptide omitted):

```
            E   V   E   L   V   E   S   G   G   G   L   V   K   P   G   G   S ·
      1   GAGGTGGAGC TGGTGGAGTC TGGGGGAGGC TTAGTGAAGC CTGGAGGGTC
          CTCCACCTCG ACCACCTCAG ACCCCCTCCG AATCACTTCG GACCTCCCAG
          · L   K   L   S   C   A   A   S   G   F   T   F   S   N   Y   A   M ·
     51   CCTGAAACTC TCCTGTGCAG CCTCTGGATT CACTTTCAGT AACTATGCCA
          GGACTTTGAG AGGACACGTC GGAGACCTAA GTGAAAGTCA TTGATACGGT
          · S   W   V   R   Q   T   P   E   K   R   L   E   W   V   A   T
    101   TGTCTTGGGT TCGCCAGACT CCGGAGAAGA GGCTGGAGTG GGTCGCAACC
          ACAGAACCCA AGCGGTCTGA GGCCTCTTCT CCGACCTCAC CCAGCGTTGG
            I   S   R   S   G   S   Y   S   Y   F   P   D   S   V   Q   G   R ·
    151   ATTAGTCGTA GTGGTAGTTA CTCCTACTTT CCAGACAGTG TGCAGGGTCG
          TAATCAGCAT CACCATCAAT GAGGATGAAA GGTCTGTCAC ACGTCCCAGC
          · F   T   I   S   R   D   N   A   K   N   T   L   Y   L   Q   M   S ·
    201   ATTCACCATC TCCAGAGACA ATGCCAAGAA CACCCTGTAC CTGCAAATGA
          TAAGTGGTAG AGGTCTCTGT TACGGTTCTT GTGGGACATG GACGTTTACT
          · S   L   R   S   E   D   T   A   M   Y   Y   C   T   R   L   G
    251   GCAGTCTGCG GTCTGAGGAC ACGGCCATGT ATTATTGTAC AAGACTTGGG
          CGTCAGACGC CAGACTCCTG TGCCGGTACA TAATAACATG TTCTGAACCC
            G   Y   D   E   G   D   A   M   D   S   W   G   Q   G   T   S   V ·
    301   GGTTACGACG AGGGGGATGC TATGGACTCC TGGGGTCAAG GAACCTCAGT
          CCAATGCTGC TCCCCCTACG ATACCTGAGG ACCCCAGTTC CTTGGAGTCA
          · T   V   S   S
    351   CACCGTCTCC TCA
          GTGGCAGAGG AGT
```

```
            1          2            3            4          5          6
123456789012345678901234567ABCDEF8901234567890123456789012345 67890 Kabat
DIVMTQTPLTLSVTIGQPASISCKSSQSLLES DGKTYLNWLLQRPGESPKLLIYLVSILDSGVPD 4F36

7          8          9           10         11         12
123456789012345678901234567 89012345AB67890123456789012345678901234 Kabat
RFTGSGSGTDFTLKISRVEAEDLGVYYCLQATHFP  QTFGGGTKLEIKRADAAPTVSIFPPSSEQ 4F36

13         14         15         16         17         18         19
567890123456789012345678901234567890123456789012345678901234567890 Kabat
LTSGGASVVCFLNNFYPRDINVKWKIDGSERQNGVLNSWTDQDSKDSTYSMSSTLTLTKDEYERHN 4F36

20         21
1234567890123456789 01234 Kabat
SYTCEATHKTSTSPIVKSFNRNEC 4F36
```

B

```
            1          2          3          4             5             6
1234567890123456789012345678912345AB67890123456789012ABC34567890 Kabat
EVELVESGGGLVKPGGSLKLSCAASGFTFSNYAMS  WVRQTPEKRLEWVATISR  SGSYSYFP 4F36

7          8             9             10              11
12345 67890123456789012ABC345678901234567890ABCDEFGHIJK12345678901 Kabat
DSVQGRFTISRDNAKNTLYLQMSSLRSEDTAMYYCTRLGGYDEGD         AMDSWGQGTSVTV 4F36

12         13         14         15         16         17
234567890123456789012345678901234567890123456789012345678901223456 Kabat
SSAKTTPPSVYPLAPGSAAQTNSMVTLGCLVKGYFPEPVTVTWNSGSLSSGVHTFPAVLQSDLYT 4F36

18         19         20         21
7890123456789012345678901234567890123456 Kabat
LSSSVTVPSSTWPSETVTCNVAHPASSTKVDKKIVPRDCG 4F36
```

Figure 4

```
1          11         21         31         41         51
DSEEDEEHTI ITDTELPPLK LMHSFCAFKA DDGPCKAIMK RFFFNIFTRQ CEEFIYGGCE 61         71         81         91         101        111
GNQNRFESLE ECKKMCTRDN ANRIIKTTLQ QEKPDFCFLE EDPGICRGYI TRYFYNNQTK 121        131        141        151        161        171
QCERFKYGGC LGNMNNFETL EECKNICEDG PNGFQVDNYG TQLNAVNNSL TPQSTKVPSL 181        191        201        211        221        231
FEFHGPSWCL TPADRGLCRA NENRFYYNSV IGKCRPFKYS GCGGNENNFT SKQECLRACK 241        251        261        271
KGFIQRISKG GLIKTKRKRK KQRVKIAYEE IFVKNM
```

C

1    QEKPDFCFLE EDPGICRGYI TRYFYNNQTK
          hhhh         s ssssss
31   QCERFKYGGC LGNMNNFETL EECKNICEDG HHHHHH
     sssssss              h hhhhhh Figure 20
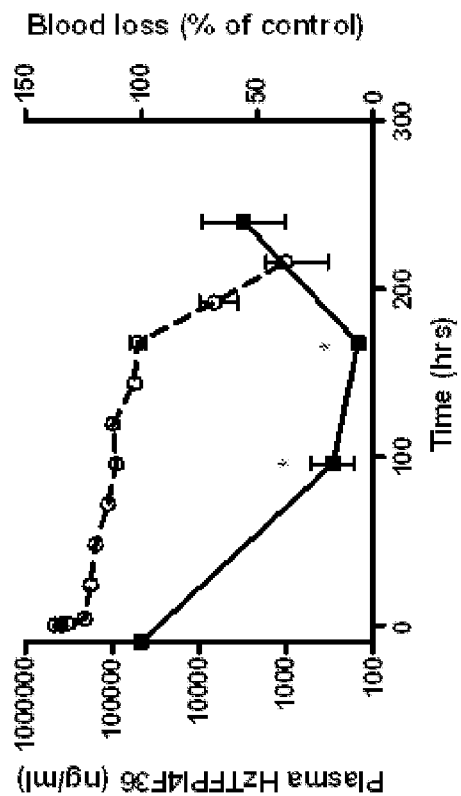
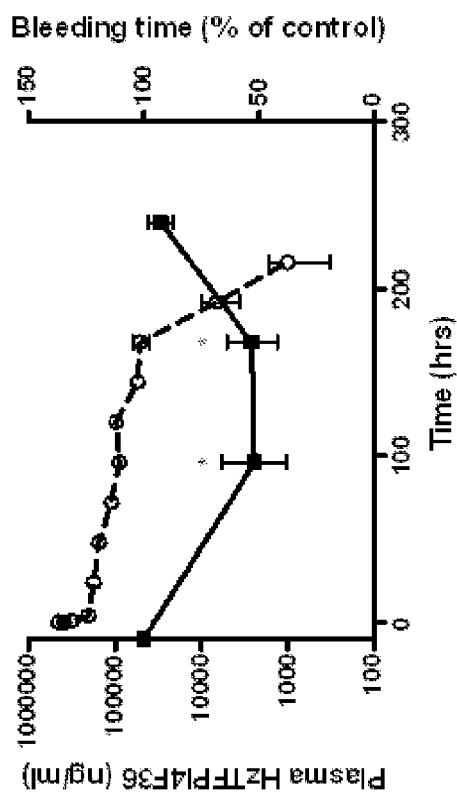

SEQUENCE LISTING

```
<160> NUMBER OF SEQ ID NOS: 34

<210> SEQ ID NO 1
<211> LENGTH: 276
<212> TYPE: PRT
<213> ORGANISM: Homo Sapiens

<400> SEQUENCE: 1

Asp Ser Glu Glu Asp Glu Glu His Thr Ile Ile Thr Asp Thr Glu Leu
1               5                   10                  15

Pro Pro Leu Lys Leu Met His Ser Phe Cys Ala Phe Lys Ala Asp Asp
            20                  25                  30

Gly Pro Cys Lys Ala Ile Met Lys Arg Phe Phe Phe Asn Ile Phe Thr
        35                  40                  45

Arg Gln Cys Glu Glu Phe Ile Tyr Gly Gly Cys Glu Gly Asn Gln Asn
    50                  55                  60

Arg Phe Glu Ser Leu Glu Glu Cys Lys Lys Met Cys Thr Arg Asp Asn
65                  70                  75                  80

Ala Asn Arg Ile Ile Lys Thr Thr Leu Gln Gln Glu Lys Pro Asp Phe
                85                  90                  95

Cys Phe Leu Glu Glu Asp Pro Gly Ile Cys Arg Gly Tyr Ile Thr Arg
            100                 105                 110

Tyr Phe Tyr Asn Asn Gln Thr Lys Gln Cys Glu Arg Phe Lys Tyr Gly
        115                 120                 125
```

```
Gly Cys Leu Gly Asn Met Asn Asn Phe Glu Thr Leu Glu Glu Cys Lys
        130                 135                 140

Asn Ile Cys Glu Asp Gly Pro Asn Gly Phe Gln Val Asp Asn Tyr Gly
145                 150                 155                 160

Thr Gln Leu Asn Ala Val Asn Asn Ser Leu Thr Pro Gln Ser Thr Lys
                165                 170                 175

Val Pro Ser Leu Phe Glu Phe His Gly Pro Ser Trp Cys Leu Thr Pro
            180                 185                 190

Ala Asp Arg Gly Leu Cys Arg Ala Asn Glu Asn Arg Phe Tyr Tyr Asn
        195                 200                 205

Ser Val Ile Gly Lys Cys Arg Pro Phe Lys Tyr Ser Gly Cys Gly Gly
210                 215                 220

Asn Glu Asn Asn Phe Thr Ser Lys Gln Glu Cys Leu Arg Ala Cys Lys
225                 230                 235                 240

Lys Gly Phe Ile Gln Arg Ile Ser Lys Gly Gly Leu Ile Lys Thr Lys
                245                 250                 255

Arg Lys Arg Lys Lys Gln Arg Val Lys Ile Ala Tyr Glu Glu Ile Phe
        260                 265                 270

Val Lys Asn Met
        275

<210> SEQ ID NO 2
<211> LENGTH: 66
<212> TYPE: PRT
<213> ORGANISM: Artificial
<220> FEATURE:
<223> OTHER INFORMATION: Artificial construct used for epitope mapping

<400> SEQUENCE: 2

Gln Glu Lys Pro Asp Phe Cys Phe Leu Glu Glu Asp Pro Gly Ile Cys
1               5                   10                  15

Arg Gly Tyr Ile Thr Arg Tyr Phe Tyr Asn Asn Gln Thr Lys Gln Cys
            20                  25                  30

Glu Arg Phe Lys Tyr Gly Gly Cys Leu Gly Asn Met Asn Asn Phe Glu
        35                  40                  45

Thr Leu Glu Glu Cys Lys Asn Ile Cys Glu Asp Gly His His His His
    50                  55                  60

His His
65

<210> SEQ ID NO 3
<211> LENGTH: 339
<212> TYPE: DNA
<213> ORGANISM: Mus musculus

<400> SEQUENCE: 3
gatattgtga tgacccagac tccactcact ttgtcggtta ccattggaca accagcttcc      60
atctcttgca agtcaagtca gagcctctta gaaagtgatg gaaaaaccta tttaaattgg    120
ttattacaga ggccaggcga gtctccaaag ctcctaatct atctggtgtc tatactggac    180
tctggagtcc ctgacaggtt cactggcagt ggatcaggga cagatttcac gctgaaaatc    240
agcagagtgg aggctgagga tttgggagtt tattattgtt tgcaagctac acattttcct    300
cagacgttcg gtggcggcac caagctggaa atcaaacgg                          339

<210> SEQ ID NO 4
<211> LENGTH: 113
<212> TYPE: PRT
```

<213> ORGANISM: Mus musculus

<400> SEQUENCE: 4

Asp Ile Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Glu Ser
            20                  25                  30

Asp Gly Lys Thr Tyr Leu Asn Trp Leu Leu Gln Arg Pro Gly Glu Ser
        35                  40                  45

Pro Lys Leu Leu Ile Tyr Leu Val Ser Ile Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Leu Gln Ala
                85                  90                  95

Thr His Phe Pro Gln Thr Phe Gly Gly Gly Thr Lys Leu Glu Ile Lys
            100                 105                 110

Arg

<210> SEQ ID NO 5
<211> LENGTH: 339
<212> TYPE: DNA
<213> ORGANISM: Mus musculus

<400> SEQUENCE: 5
ccgtttgatt tccagcttgg tgccgccacc gaacgtctga ggaaaatgtg tagcttgcaa      60
acaataataa actcccaaat cctcagcctc cactctgctg attttcagcg tgaaatctgt    120
ccctgatcca ctgccagtga acctgtcagg gactccagag tccagtatag acaccagata    180
gattaggagc tttggagact cgcctggcct ctgtaataac caatttaaat aggttttttcc   240 atcactttct aagaggctct gacttgactt gcaagagatg gaagctggtt gtccaatggt    300
aaccgacaaa gtgagtggag tctgggtcat cacaatatc                           339

<210> SEQ ID NO 6
<211> LENGTH: 219
<212> TYPE: PRT
<213> ORGANISM: Mus musculus

<400> SEQUENCE: 6

Asp Ile Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Glu Ser
            20                  25                  30

Asp Gly Lys Thr Tyr Leu Asn Trp Leu Leu Gln Arg Pro Gly Glu Ser
        35                  40                  45

Pro Lys Leu Leu Ile Tyr Leu Val Ser Ile Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Leu Gln Ala
                85                  90                  95

Thr His Phe Pro Gln Thr Phe Gly Gly Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe

```
                    130                 135                 140
Tyr Pro Arg Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215

<210> SEQ ID NO 7
<211> LENGTH: 363
<212> TYPE: DNA
<213> ORGANISM: Mus musculus

<400> SEQUENCE: 7
gaggtggagc tggtggagtc tgggggaggc ttagtgaagc ctggagggtc cctgaaactc      60
tcctgtgcag cctctggatt cactttcagt aactatgcca tgtcttgggt tcgccagact     120
ccggagaaga ggctggagtg ggtcgcaacc attagtcgta gtggtagtta ctcctacttt     180
ccagacagtg tgcagggtcg attcaccatc tccagagaca atgccaagaa caccctgtac     240
ctgcaaatga gcagtctgcg gtctgaggac acggccatgt attattgtac aagacttggg     300
ggttacgacg agggggatgc tatggactcc tggggtcaag gaacctcagt caccgtctcc     360
tca                                                                    363

<210> SEQ ID NO 8
<211> LENGTH: 121
<212> TYPE: PRT
<213> ORGANISM: Mus musculus

<400> SEQUENCE: 8

Glu Val Glu Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asn Tyr
            20                  25                  30

Ala Met Ser Trp Val Arg Gln Thr Pro Glu Lys Arg Leu Glu Trp Val
        35                  40                  45

Ala Thr Ile Ser Arg Ser Gly Ser Tyr Ser Tyr Phe Pro Asp Ser Val
    50                  55                  60

Gln Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Thr Arg Leu Gly Gly Tyr Asp Glu Gly Asp Ala Met Asp Ser Trp Gly
            100                 105                 110

Gln Gly Thr Ser Val Thr Val Ser Ser
        115                 120

<210> SEQ ID NO 9
<211> LENGTH: 363
<212> TYPE: DNA
<213> ORGANISM: Mus musculus

<400> SEQUENCE: 9
tgaggagacg gtgactgagg ttccttgacc ccaggagtcc atagcatccc cctcgtcgta      60
```

-continued

```
acccccaagt cttgtacaat aatacatggc cgtgtcctca gaccgcagac tgctcatttg    120
caggtacagg gtgttcttgg cattgtctct ggagatggtg aatcgaccct gcacactgtc    180
tggaaagtag gagtaactac cactacgact aatggttgcg acccactcca gcctcttctc    240
cggagtctgg cgaacccaag acatggcata gttactgaaa gtgaatccag aggctgcaca    300
ggagagtttc agggaccctc caggcttcac taagcctccc ccagactcca ccagctccac    360
ctc                                                                  363
```

<210> SEQ ID NO 10
<211> LENGTH: 445
<212> TYPE: PRT
<213> ORGANISM: Mus musculus

<400> SEQUENCE: 10

| | | | | | | | | | | | | | | |
|---|---|---|---|---|---|---|---|---|---|---|---|---|---|---|
| Glu | Val | Glu | Leu | Val | Glu | Ser | Gly | Gly | Gly | Leu | Val | Lys | Pro | Gly |
| 1 | | | | 5 | | | | | 10 | | | | | 15 |
| Gly | Ser | Leu | Lys | Leu | Ser | Cys | Ala | Ala | Ser | Gly | Phe | Thr | Phe | Ser |
| | | | 20 | | | | | 25 | | | | | 30 | |
| Asn | Tyr | Ala | Met | Ser | Trp | Val | Arg | Gln | Thr | Pro | Glu | Lys | Arg | Leu |
| | | | 35 | | | | | 40 | | | | | 45 | |
| Glu | Trp | Val | Ala | Thr | Ile | Ser | Arg | Ser | Gly | Ser | Tyr | Ser | Tyr | Phe |
| | | | 50 | | | | | 55 | | | | | 60 | |
| Pro | Asp | Ser | Val | Gln | Gly | Arg | Phe | Thr | Ile | Ser | Arg | Asp | Asn | Ala |
| 65 | | | | | 70 | | | | | 75 | | | | | 80 |
| Lys | Asn | Thr | Leu | Tyr | Leu | Gln | Met | Ser | Ser | Leu | Arg | Ser | Glu | Asp |
| | | | | | | | | 85 | | | | | 90 | |
| Thr | Ala | Met | Tyr | Tyr | Cys | Thr | Arg | Leu | Gly | Gly | Tyr | Asp | Glu | Gly |
| | | 95 | | | | | | 100 | | | | | 105 | |
| Asp | Ala | Met | Asp | Ser | Trp | Gly | Gln | Gly | Thr | Ser | Val | Thr | Val | Ser |
| | | | 110 | | | | | 115 | | | | | 120 | |
| Ser | Ala | Lys | Thr | Thr | Pro | Pro | Ser | Val | Tyr | Pro | Leu | Ala | Pro | Gly |
| | | | 125 | | | | | 130 | | | | | 135 | |
| Ser | Ala | Ala | Gln | Thr | Asn | Ser | Met | Val | Thr | Leu | Gly | Cys | Leu | Val |
| | | | 140 | | | | | 145 | | | | | 150 | |
| Lys | Gly | Tyr | Phe | Pro | Glu | Pro | Val | Thr | Val | Thr | Trp | Asn | Ser | Gly |
| | | | | 155 | | | | | 160 | | | | | 165 | |
| Ser | Leu | Ser | Ser | Gly | Val | His | Thr | Phe | Pro | Ala | Val | Leu | Gln | Ser |
| | | | | 170 | | | | | 175 | | | | | 180 | |
| Asp | Leu | Tyr | Thr | Leu | Ser | Ser | Ser | Val | Thr | Val | Pro | Ser | Ser | Thr |
| | | | 185 | | | | | 190 | | | | | | 195 |
| Trp | Pro | Ser | Glu | Thr | Val | Thr | Cys | Asn | Val | Ala | His | Pro | Ala | Ser |
| | | | 200 | | | | | 205 | | | | | 210 | |
| Ser | Thr | Lys | Val | Asp | Lys | Lys | Ile | Val | Pro | Arg | Asp | Cys | Gly | Cys |
| | | | 215 | | | | | 220 | | | | | | 225 |
| Lys | Pro | Cys | Ile | Cys | Thr | Val | Pro | Glu | Val | Ser | Ser | Val | Phe | Ile |
| | | 230 | | | | | | 235 | | | | | 240 | |
| Phe | Pro | Pro | Lys | Pro | Lys | Asp | Val | Leu | Thr | Ile | Thr | Leu | Thr | Pro |
| | | | 245 | | | | | 250 | | | | | 255 | |
| Lys | Val | Thr | Cys | Val | Val | Val | Asp | Ile | Ser | Lys | Asp | Asp | Pro | Glu |
| | | | | 260 | | | | | 265 | | | | | 270 | |
| Val | Gln | Phe | Ser | Trp | Phe | Val | Asp | Asp | Val | Glu | Val | His | Thr | Ala |
| | | | 275 | | | | | 280 | | | | | 285 | |
| Gln | Thr | Gln | Pro | Arg | Glu | Glu | Gln | Phe | Asn | Ser | Thr | Phe | Arg | Ser |
| | | | | 290 | | | | | 295 | | | | | 300 | |
| Val | Ser | Glu | Leu | Pro | Ile | Met | His | Gln | Asp | Trp | Leu | Asn | Gly | Lys |
| | | | | | 305 | | | | | 310 | | | | | 315 |
| Glu | Phe | Lys | Cys | Arg | | | | | | | | | | |
| | | | | 320 | | | | | | | | | | |

```
Val Asn Ser Ala Ala Phe Pro Ala Pro Ile Glu Lys Thr Ile Ser Lys
            325                 330                 335

Thr Lys Gly Arg Pro Lys Ala Pro Gln Val Tyr Thr Ile Pro Pro Pro
            340                 345                 350

Lys Glu Gln Met Ala Lys Asp Lys Val Ser Leu Thr Cys Met Ile Thr
            355                 360                 365

Asp Phe Phe Pro Glu Asp Ile Thr Val Glu Trp Gln Trp Asn Gly Gln
    370                 375                 380

Pro Ala Glu Asn Tyr Lys Asn Thr Gln Pro Ile Met Asp Thr Asp Gly
385                 390                 395                 400

Ser Tyr Phe Val Tyr Ser Lys Leu Asn Val Gln Lys Ser Asn Trp Glu
            405                 410                 415

Ala Gly Asn Thr Phe Thr Cys Ser Val Leu His Glu Gly Leu His Asn
            420                 425                 430

His His Thr Glu Lys Ser Leu Ser His Ser Pro Gly Lys
            435                 440                 445

<210> SEQ ID NO 11
<211> LENGTH: 20
<212> TYPE: DNA
<213> ORGANISM: Artificial
<220> FEATURE:
<223> OTHER INFORMATION: primer

<400> SEQUENCE: 11
cccttgacca ggcatcccag                                                20

<210> SEQ ID NO 12
<211> LENGTH: 36
<212> TYPE: DNA
<213> ORGANISM: Artificial
<220> FEATURE:
<223> OTHER INFORMATION: primer

<400> SEQUENCE: 12
gctctagact aacactcatt cctgttgaag ctcttg                              36

<210> SEQ ID NO 13
<211> LENGTH: 339
<212> TYPE: DNA
<213> ORGANISM: Artificial
<220> FEATURE:
<223> OTHER INFORMATION: Humanized variable light chain

<400> SEQUENCE: 13
gacatcgtga tgacccagac ccctctgtcc ctgtccgtga cccctggcca gcctgcctcc    60
atctcctgca gtcctcccca gtccctgctg gaatccgacg gcaagaccta cctgaactgg   120
tatctgcaga gcctggcca gtcccctcag ctgctgatct acctggtgtc catcctggac   180
tccggcgtgc ctgaccggtt ctccggctcc ggcagcggca ccgacttcac cctgaagatc   240
tcccgggtgg aggccgagga cgtgggcgtg tactactgcc tgcaggccac ccacttccct   300
cagacctttg gcggcggaac aaaggtggag atcaagcgt                         339

<210> SEQ ID NO 14
<211> LENGTH: 339
<212> TYPE: DNA
<213> ORGANISM: Artificial
<220> FEATURE:
<223> OTHER INFORMATION: Humanized variable light chain

<400> SEQUENCE: 14
```

```
ctgtagcact actgggtctg gggagacagg gacaggcact ggggaccggt cggacggagg    60
taggggacgt tcaggagggt cagggacgac cttaggctgc cgttctggat ggacttgacc   120
atagacgtct tcggaccggt caggggagtc gacgactaga tggaccacag gtaggacctg   180
aggccgcacg gactggccaa gaggccgagg ccgtcgccgt ggctgaagtg ggacttctag   240
agggcccacc tccggctcct gcacccgcac atgatgacgg acgtccggtg ggtgaaggga   300
gtctggaaac cgccgccttg tttccacctc tagttcgca                          339
```

<210> SEQ ID NO 15
<211> LENGTH: 113
<212> TYPE: PRT
<213> ORGANISM: Artificial
<220> FEATURE:
<223> OTHER INFORMATION: Humanized variable light chain
<400> SEQUENCE: 15

```
Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Glu Ser
            20                  25                  30

Asp Gly Lys Thr Tyr Leu Asn Trp Tyr Leu Gln Lys Pro Gly Gln Ser
        35                  40                  45

Pro Gln Leu Leu Ile Tyr Leu Val Ser Ile Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Ala
                85                  90                  95

Thr His Phe Pro Gln Thr Phe Gly Gly Gly Thr Lys Val Glu Ile Lys
            100                 105                 110

Arg
```

<210> SEQ ID NO 16
<211> LENGTH: 363
<212> TYPE: DNA
<213> ORGANISM: Artificial
<220> FEATURE:
<223> OTHER INFORMATION: Humanized variable heavy chain
<400> SEQUENCE: 16

```
gaggtgcagc tggtcgagtc tggcggcgga ctggtgaagc ctggcggctc cctgcggctg    60
tcctgcgctg cctccggctt caccttctcc aactacgcca tgtcctgggt gcggcagacc   120
ccagaaaagc ggctggaatg ggtggccacc atctcccgt ccggctccta ctcctacttc   180
cctgactccg tgcagggccg gttcaccatc agcagggaca cgccaagaa ctccctgtac   240 ctgcagatga actccctgag agccgaggac acagccgtgt actactgcgc caggctgggc   300
ggctacgacg agggcgacgc catggacagc tggggccagg gcaccaccgt gaccgtgtcc   360
tcc                                                                 363
```

<210> SEQ ID NO 17
<211> LENGTH: 363
<212> TYPE: DNA
<213> ORGANISM: Artificial
<220> FEATURE:
<223> OTHER INFORMATION: Humanized variable heavy chain
<400> SEQUENCE: 17

```
ctccacgtcg accagctcag accgccgcct gaccacttcg gaccgccgag ggacgccgac        60
aggacgcgac ggaggccgaa gtggaagagg ttgatgcggt acaggaccca cgccgtctgg       120
ggtcttttcg ccgaccttac ccaccggtgg tagagggcca ggccgaggat gaggatgaag       180
ggactgaggc acgtcccggc caagtggtag tcgtccctgt tgcggttctt gagggacatg       240
gacgtctact tgagggactc tcggctcctg tgtcggcaca tgatgacgcg gtccgacccg       300
ccgatgctgc tcccgctgcg gtacctgtcg accccggtcc cgtggtggca ctggcacagg       360
agg                                                                    363
```

<210> SEQ ID NO 18
<211> LENGTH: 121
<212> TYPE: PRT
<213> ORGANISM: Artificial
<220> FEATURE:
<223> OTHER INFORMATION: Humanized variable heavy chain

<400> SEQUENCE: 18

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Tyr
            20                  25                  30

Ala Met Ser Trp Val Arg Gln Thr Pro Glu Lys Arg Leu Glu Trp Val
        35                  40                  45

Ala Thr Ile Ser Arg Ser Gly Ser Tyr Ser Tyr Phe Pro Asp Ser Val
    50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Gly Tyr Asp Glu Gly Asp Ala Met Asp Ser Trp Gly
            100                 105                 110

Gln Gly Thr Thr Val Thr Val Ser Ser
        115                 120
```

<210> SEQ ID NO 19
<211> LENGTH: 657
<212> TYPE: DNA
<213> ORGANISM: Artificial
<220> FEATURE:
<223> OTHER INFORMATION: Humanized constant light chain

<400> SEQUENCE: 19

```
gacatcgtga tgacccagac ccctctgtcc ctgtccgtga cccctggcca gcctgcctcc        60
atctcctgca gtcctcccca gtccctgctg aatccgacg gcaagaccta cctgaactgg       120
tatctgcaga gcctggcca gtcccctcag ctgctgatct acctggtgtc catcctggac       180
tccggcgtgc ctgaccggtt ctccggctcc ggcagcggca ccgacttcac cctgaagatc       240
tcccgggtgg aggccgagga cgtgggcgtg tactactgcc tgcaggccac ccacttccct       300 cagaccctg gcggcggaac aaaggtggag atcaagcgta cggtggctgc accatctgtc       360
ttcatcttcc cgccatctga tgagcagttg aaatctggaa ctgcctctgt tgtgtgcctg       420
ctgaataact tctatcccag agaggccaaa gtacagtgga aggtggataa cgccctccaa       480
tcgggtaact cccaggagag tgtcacagag caggacagca aggacagcac ctacagcctc       540
agcagcaccc tgacgctgag caaagcagac tacgagaaac acaaagtcta cgcctgcgaa       600
gtcacccatc agggcctgag ctcgcccgtc acaaagagct tcaacagggg agagtgt         657
```

<210> SEQ ID NO 20
<211> LENGTH: 657
<212> TYPE: DNA
<213> ORGANISM: Artificial
<220> FEATURE:
<223> OTHER INFORMATION: Humanized constant light chain

<400> SEQUENCE: 20

```
ctgtagcact actgggtctg gggagacagg gacaggcact ggggaccggt cggacggagg      60
tagaggacgt tcaggagggt cagggacgac cttaggctgc cgttctggat ggacttgacc     120
atagacgtct tcggaccggt cagggagtc gacgactaga tggaccacag gtaggacctg     180
aggccgcacg gactggccaa gaggccgagg ccgtcgccgt ggctgaagtg ggacttctag     240
agggcccacc tccggctcct gcacccgcac atgatgacgg acgtccggtg ggtgaaggga     300
gtctggaaac cgccgccttg tttccacctc tagttcgcat gccaccgacg tggtagacag     360
aagtagaagg gcggtagact actcgtcaac tttagacctt gacggagaca acacacggac     420
gacttattga agatagggtc tctccggttt catgtcacct tccacctatt gcgggaggtt     480
agcccattga gggtcctctc acagtgtctc gtcctgtcgt tcctgtcgtg gatgtcggag     540
tcgtcgtggg actgcgactc gtttcgtctg atgctctttg tgtttcagat gcggacgctt     600
cagtgggtag tcccggactc gagcgggcag tgtttctcga agttgtcccc tctcaca       657
```

<210> SEQ ID NO 21
<211> LENGTH: 219
<212> TYPE: PRT
<213> ORGANISM: Artificial
<220> FEATURE:
<223> OTHER INFORMATION: Humanized constant light chain

<400> SEQUENCE: 21

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Glu Ser
            20                  25                  30

Asp Gly Lys Thr Tyr Leu Asn Trp Tyr Leu Gln Lys Pro Gly Gln Ser
        35                  40                  45

Pro Gln Leu Leu Ile Tyr Leu Val Ser Ile Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Ala
                85                  90                  95

Thr His Phe Pro Gln Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 22
<211> LENGTH: 1344
<212> TYPE: DNA
<213> ORGANISM: Artificial
<220> FEATURE:
<223> OTHER INFORMATION: Humanized constant heavy chain

<400> SEQUENCE: 22

| | | | | |
|---|---|---|---|---|
| gaggtgcagc | tggtcgagtc | tggcggcgga | ctggtgaagc | ctggcggctc  cctgcggctg | 60 |
| tcctgcgctg | cctccggctt | caccttctcc | aactacgcca | tgtcctgggt  gcggcagacc | 120 |
| ccagaaaagc | ggctggaatg | ggtggccacc | atctcccgt | ccggctccta  ctcctacttc | 180 |
| cctgactccg | tgcagggccg | gttcaccatc | agcagggaca | acgccaagaa  ctccctgtac | 240 |
| ctgcagatga | actccctgag | agccgaggac | acagccgtgt | actactgcgc  caggctgggc | 300 |
| ggctacgacg | agggcgacgc | catggacagc | tggggccagg | gcaccaccgt  gaccgtgtcc | 360 |
| tccgctagca | ccaagggccc | atccgtcttc | cccctggcgc | cctgctccag  gagcacctcc | 420 |
| gagagcacag | ccgccctggg | ctgcctggtc | aaggactact | ccccgaacc  ggtgacggtg | 480 |
| tcgtggaact | caggcgccct | gaccagcggc | gtgcacacct | tcccggctgt  cctacagtcc | 540 |
| tcaggactct | actccctcag | cagcgtggtg | accgtgccct | ccagcagctt  gggcacgaag | 600 |
| acctacacct | gcaacgtaga | tcacaagccc | agcaacacca | aggtggacaa  gagagttgag | 660 |
| tccaaatatg | gtcccccatg | cccaccatgc | ccagcacctg | agttcctggg  gggaccatca | 720 |
| gtcttcctgt | tccccccaaa | acccaaggac | actctcatga | tctcccggac  ccctgaggtc | 780 |
| acgtgcgtgg | tggtggacgt | gagccaggaa | gaccccgagg | tccagttcaa  ctggtacgtg | 840 |
| gatggcgtgg | aggtgcataa | tgccaagaca | aagccgcggg | aggagcagtt  caacagcacg | 900 |
| taccgtgtgg | tcagcgtcct | caccgtcctg | caccaggact | ggctgaacgg  caaggagtac | 960 |
| aagtgcaagg | tctccaacaa | aggcctcccg | tcctccatcg | agaaaaccat  ctccaaagcc | 1020 |
| aaagggcagc | cccgagagcc | acaggtgtac | accctgcccc | catcccagga  ggagatgacc | 1080 |
| aagaaccagg | tcagcctgac | ctgcctggtc | aaaggcttct | accccagcga  catcgccgtg | 1140 |
| gagtgggaga | gcaatgggca | gccggagaac | aactacaaga | ccacgcctcc  cgtgctggac | 1200 |
| tccgacggct | ccttcttcct | ctacagcagg | ctaaccgtgg | acaagagcag  gtggcaggag | 1260 |
| gggaatgtct | tctcatgctc | cgtgatgcat | gaggctctgc | acaaccacta  cacacagaag | 1320 |
| agcctctccc | tgtctctggg | taaa | | | 1344 |

<210> SEQ ID NO 23
<211> LENGTH: 1344
<212> TYPE: DNA
<213> ORGANISM: Artificial
<220> FEATURE:
<223> OTHER INFORMATION: Humanized constant heavy chain

<400> SEQUENCE: 23

| | | | | |
|---|---|---|---|---|
| ctccacgtcg | accagctcag | accgccgcct | gaccacttcg | gaccgccgag  ggacgccgac | 60 |
| aggacgcgac | ggaggccgaa | gtggaagagg | ttgatgcggt | acaggaccca  cgccgtctgg | 120 |
| ggtcttttcg | ccgaccttac | ccaccggtgg | tagagggcca | ggccgaggat  gaggatgaag | 180 |
| ggactgaggc | acgtcccggc | caagtggtag | tcgtccctgt | tgcggttctt  gagggacatg | 240 |
| gacgtctact | tgagggactc | tcggctcctg | tgtcggcaca | tgatgacgcg  gtccgacccg | 300 |

```
ccgatgctgc tcccgctgcg gtacctgtcg accccggtcc cgtggtggca ctggcacagg      360
aggcgatcgt ggttcccggg taggcagaag ggggaccgcg ggacgaggtc ctcgtggagg      420
ctctcgtgtc ggcgggaccc gacggaccag ttcctgatga aggggcttgg ccactgccac      480
agcaccttga gtccgcggga ctggtcgccg cacgtgtgga agggccgaca ggatgtcagg      540
agtcctgaga tgagggagtc gtcgcaccac tggcacggga ggtcgtcgaa cccgtgcttc      600
tggatgtgga cgttgcatct agtgttcggg tcgttgtggt tccacctgtt ctctcaactc      660
aggtttatac caggggggtac gggtggtacg ggtcgtggac tcaaggaccc ccctggtagt      720
cagaaggaca agggggggttt tgggttcctg tgagagtact agagggcctg ggactccag      780
tgcacgcacc accacctgca ctcggtcctt ctggggctcc aggtcaagtt gaccatgcac      840
ctaccgcacc tccacgtatt acggttctgt tcggcgccc tcctcgtcaa gttgcgtgc      900
atggcacacc agtcgcagga gtggcaggac gtggtcctga ccgacttgcc gttcctcatg      960
ttcacgttcc agaggttgtt tccggagggc aggaggtagc tcttttggta gaggtttcgg     1020
tttcccgtcg gggctctcgg tgtccacatg tgggacgggg gtagggtcct cctctactgg     1080
ttcttggtcc agtcggactg gacggaccag tttccgaaga tggggtcgct gtagcggcac     1140
ctcaccctct cgttacccgt cggcctcttg ttgatgttct ggtgcggagg gcacgacctg     1200
aggctgccga ggaagaagga gatgtcgtcc gattggcacc tgttctcgtc caccgtcctc     1260
cccttacaga gagtacgag gcactacgta ctccgagacg tgttggtgat gtgtgtcttc     1320
tcggagaggg acagagaccc attt                                             1344

<210> SEQ ID NO 24
<211> LENGTH: 448
<212> TYPE: PRT
<213> ORGANISM: Artificial
<220> FEATURE:
<223> OTHER INFORMATION: Humanized constant heavy chain

<400> SEQUENCE: 24

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Thr Pro Glu Lys Arg Leu Glu Trp Val
        35                  40                  45

Ala Thr Ile Ser Arg Ser Gly Ser Tyr Ser Tyr Phe Pro Asp Ser Val
    50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Gly Tyr Asp Glu Gly Asp Ala Met Asp Ser Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
```

```
                      180                 185                 190
Pro Ser Ser Ser Leu Gly Thr Lys Thr Tyr Thr Cys Asn Val Asp His
                195                 200                 205
Lys Pro Ser Asn Thr Lys Val Asp Lys Arg Val Glu Ser Lys Tyr Gly
            210                 215                 220
Pro Pro Cys Pro Pro Cys Pro Ala Pro Glu Phe Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser Gln Glu Asp Pro
            260                 265                 270
Glu Val Gln Phe Asn Trp Tyr Val Asp Gly Val Glu Val His Asn Ala
        275                 280                 285
Lys Thr Lys Pro Arg Glu Glu Gln Phe Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Gly Leu Pro Ser Ser Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Gln Glu Glu Met Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Arg Leu Thr Val Asp Lys Ser
                405                 410                 415
Arg Trp Gln Glu Gly Asn Val Phe Ser Cys Ser Val Met His Glu Ala
            420                 425                 430
Leu His Asn His Tyr Thr Gln Lys Ser Leu Ser Leu Ser Leu Gly Lys
        435                 440                 445

<210> SEQ ID NO 25
<211> LENGTH: 339
<212> TYPE: DNA
<213> ORGANISM: Artificial
<220> FEATURE:
<223> OTHER INFORMATION: HzTFPI4F36-CDRgrafted VL nucleic acid sequence
      (signal peptide sequence omitted)

<400> SEQUENCE: 25
gacatcgtga tgacccagac ccctctgtcc ctgtccgtga cccctggcca gcctgcctcc       60
atctcctgca gtcctcccca gtccctgctg aatccgacg gcaagaccta cctgaactgg      120
tatctgcaga gcctggcca gtcccctcag ctgctgatct acctggtgtc catcctggac      180
tccggcgtgc ctgaccggtt ctccggctcc ggcagcggca ccgacttcac cctgaagatc      240
tcccgggtgg aggccgagga cgtgggcgtg tactactgcc tgcaggccac ccacttccct      300
cagacctttg gcggcggaac aaaggtggag atcaagcgt                              339

<210> SEQ ID NO 26
<211> LENGTH: 113
<212> TYPE: PRT
<213> ORGANISM: Artificial
<220> FEATURE:
<223> OTHER INFORMATION: HzTFPI4F36-CDRgrafted VL amino acid sequence
```

(signal peptide sequence omitted)

<400> SEQUENCE: 26

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Glu Ser
            20                  25                  30

Asp Gly Lys Thr Tyr Leu Asn Trp Tyr Leu Gln Lys Pro Gly Gln Ser
        35                  40                  45

Pro Gln Leu Leu Ile Tyr Leu Val Ser Ile Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Ala
                85                  90                  95

Thr His Phe Pro Gln Thr Phe Gly Gly Gly Thr Lys Val Glu Ile Lys
            100                 105                 110

Arg

<210> SEQ ID NO 27
<211> LENGTH: 363
<212> TYPE: DNA
<213> ORGANISM: Artificial
<220> FEATURE:
<223> OTHER INFORMATION: HzTFPI4F36-CDRgrafted VH nucleic acid sequence
      (signal peptide sequence omitted)

<400> SEQUENCE: 27

```
gaggtgcagc tggtcgagtc tggcggcgga ctggtgaagc ctggcggctc cctgcggctg      60
tcctgcgctg cctccggctt caccttctcc aactacgcca tgtcctgggt gcggcaggcc     120
ccagggaagg gactggaatg ggtgtccacc atctcccggt ccggctccta ctcctactac     180
gccgactccg tgaagggccg gttcaccatc agcagggaca cgccaagaa ctccctgtac      240 ctgcagatga actccctgag agccgaggac acagccgtgt actactgcgc caggctgggc    300
ggctacgacg agggcgacgc catggacagc tggggccagg gcaccaccgt gaccgtgtcc    360
tcc                                                                    363
```

<210> SEQ ID NO 28
<211> LENGTH: 121
<212> TYPE: PRT
<213> ORGANISM: Artificial
<220> FEATURE:
<223> OTHER INFORMATION: HzTFPI4F36-CDRgrafted VH amino acid sequence
      (signal peptide sequence omitted)

<400> SEQUENCE: 28

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Thr Ile Ser Arg Ser Gly Ser Tyr Ser Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Gly Tyr Asp Glu Gly Asp Ala Met Asp Ser Trp Gly
            100                 105                 110

Gln Gly Thr Thr Val Thr Val Ser Ser
            115                 120

<210> SEQ ID NO 29
<211> LENGTH: 219
<212> TYPE: PRT
<213> ORGANISM: Artificial
<220> FEATURE:
<223> OTHER INFORMATION: HzTFPI4F36-CDRgrafted LC amino acid sequence,
      human kappa chain (signal peptide sequence omitted)

<400> SEQUENCE: 29

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Glu Ser
            20                  25                  30

Asp Gly Lys Thr Tyr Leu Asn Trp Tyr Leu Gln Lys Pro Gly Gln Ser
        35                  40                  45

Pro Gln Leu Leu Ile Tyr Leu Val Ser Ile Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Ala
                85                  90                  95

Thr His Phe Pro Gln Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 30
<211> LENGTH: 448
<212> TYPE: PRT
<213> ORGANISM: Artificial
<220> FEATURE:
<223> OTHER INFORMATION: HzTFPI4F36-CDRgrafted HC amino acid sequence,
      human IgG4(S241P) (signal peptide sequence omitted)

<400> SEQUENCE: 30

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Thr Ile Ser Arg Ser Gly Ser Tyr Tyr Ala Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Leu Gly Gly Tyr Asp Glu Gly Asp Ala Met Asp Ser Trp Gly
            100                 105                 110

Gln Gly Thr Thr Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
            195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
            435                 440                 445

<210> SEQ ID NO 31
<211> LENGTH: 112
<212> TYPE: PRT
<213> ORGANISM: Homo sapiens

<400> SEQUENCE: 31

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Ser
        35                  40                  45

Pro Gln Leu Leu Ile Tyr Glu Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Ile His Leu Pro Thr Phe Gly Gly Gly Thr Lys Val Glu Ile Lys Arg
            100                 105                 110

<210> SEQ ID NO 32
<211> LENGTH: 112
<212> TYPE: PRT
<213> ORGANISM: Homo sapiens

<400> SEQUENCE: 32

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Met Asp Val Trp Gly Gln Gly Thr Thr Val Thr Val Ser Ser
            100                 105                 110

<210> SEQ ID NO 33
<211> LENGTH: 224
<212> TYPE: PRT
<213> ORGANISM: Mus musculus

<400> SEQUENCE: 33

Glu Val Glu Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asn Tyr
            20                  25                  30

Ala Met Ser Trp Val Arg Gln Thr Pro Glu Lys Arg Leu Glu Trp Val
        35                  40                  45

Ala Thr Ile Ser Arg Ser Gly Ser Tyr Ser Tyr Phe Pro Asp Ser Val
    50                  55                  60

Gln Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Thr Arg Leu Gly Gly Tyr Asp Glu Gly Asp Ala Met Asp Ser Trp Gly

```
                100             105             110
Gln Gly Thr Ser Val Thr Val Ser Ser Ala Lys Thr Thr Pro Pro Ser
            115                 120                 125

Val Tyr Pro Leu Ala Pro Gly Ser Ala Ala Gln Thr Asn Ser Met Val
            130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
            165                 170                 175

Val Leu Gln Ser Asp Leu Tyr Thr Leu Ser Ser Val Thr Val Pro
            180                 185                 190

Ser Ser Thr Trp Pro Ser Glu Thr Val Thr Cys Asn Val Ala His Pro
            195                 200                 205

Ala Ser Ser Thr Lys Val Asp Lys Lys Ile Val Pro Arg Asp Cys Gly
            210                 215                 220
```

<210> SEQ ID NO 34
<211> LENGTH: 222
<212> TYPE: PRT
<213> ORGANISM: Homo sapiens

<400> SEQUENCE: 34

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Thr Pro Glu Lys Arg Leu Glu Trp Val
            35                  40                  45

Ala Thr Ile Ser Arg Ser Gly Ser Tyr Ser Tyr Phe Pro Asp Ser Val
            50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Leu Gly Gly Tyr Asp Glu Gly Asp Ala Met Asp Ser Trp Gly
            100                 105                 110

Gln Gly Thr Thr Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
            195                 200                 205

Lys Pro Ser Asn Thr Lys Val Asp Lys Arg Val Glu Ser Lys
            210                 215                 220
```

ANTIBODIES AGAINST TISSUE FACTOR PATHWAY INHIBITOR

CROSS-REFERENCE TO RELATED APPLICATIONS

This application is a 35 U.S.C. §371 national stage application of International Patent Application PCT/EP2009/067598 (published as WO 2010/072691 A1), filed Dec. 18, 2009, which claimed priority of European Patent Application 08172520.2, filed Dec. 22, 2008; this application further claims priority under 35 U.S.C. §119 of U.S. Provisional Application 61/203,479, filed Dec. 23, 2008.

FIELD OF THE INVENTION

The present invention relates to antibodies that specifically bind to tissue factor pathway inhibitor (TFPI).

INCORPORATION-BY-REFERENCE OF THE SEQUENCE LISTING

In accordance with 37 C.F.R. §1.52(e)(5), Applicants enclose herewith the Sequence Listing for the above-captioned application entitled "SEQUENCE LISTING", created on May 26, 2011. The Sequence Listing is made up of 46,035 bytes, and the information contained in the attached "SEQUENCE LISTING" is identical to the information in the specification as originally filed. No new matter is added.

BACKGROUND OF THE INVENTION

In subjects with a coagulopathy, such as in human beings with haemophilia A and B, various steps of the coagulation cascade are rendered dysfunctional due to, for example, the absence or insufficient presence of a coagulation factor. Such dysfunction of one part of the coagulation cascade results in insufficient blood coagulation and potentially life-threatening bleeding, or damage to internal organs, such as the joints. Subjects such as human beings with haemophilia A and B may receive coagulation factor replacement therapy such as exogenous FVIIIa or FIXa, respectively. However, such patients are at risk of developing "inhibitors" (antibodies) to such exogenous factors, rendering formerly efficient therapy ineffective. Furthermore, exogenous coagulation factors may only be administered intravenously, which is of considerable inconvenience and discomfort to patients. For example, infants and toddlers may have to have intravenous catheters surgically inserted into a chest vein, in order for venous access to be guaranteed. This leaves them at great risk of developing bacterial infections. Subjects with a coagulopathy may only receive therapy after a bleed has commenced, rather than as a precautionary measure, which often impinges upon their general quality of life.

There are thus still many unmet medical needs in the haemophilia community, in particular, and in subjects with coagulopathies, in general.

When a vessel wall is injured, tissue factor (TF) is exposed to the contents of circulating blood and TF forms a complex with Factor VII/activated Factor VII (FVII/FVIIa) on the surface of TF-bearing cells. This leads to the activation of Factor X (FX) to FXa which together with FVa generates a limited amount of thrombin (FIIa). Small amounts of thrombin activate platelets, which results in surface exposure of phospholipids that supports the binding of the tenase complex consisting of FVIIIa/FIXa.

The tenase complex produces large amounts of FXa, which subsequently facilitates a full thrombin burst. A full thrombin burst is needed for the formation of a mechanically strong fibrin structure and stabilization of the haemostatic plug. FVIII or FIX is missing or present at low levels in haemophilia patients, and due to the lack of tenase activity, the capacity to generate FXa is low and insufficient to support the propagation phase of the coagulation. In contrast, the TF-mediated initiation phase is not dependent on the formation of the tenase complex. However, the TF-pathway will, shortly after an initial FXa generation, be blocked by plasma inhibitors.

Tissue factor pathway inhibitor (TFPI) down-regulates ongoing coagulation by neutralizing the catalytic activity of FXa and by inhibiting the TF-FVIIa complex in the presence of FXa. TFPI either inhibits the TF/FVIIa/FXa complex on the cellular surface or inhibits released FXa followed by FVIIa/TF inhibition.

SUMMARY OF THE INVENTION

The Inventors have identified monoclonal antibodies which specifically bind to tissue factor pathway inhibitor ("TFPI", sometimes referred to as "TFPI1") and thereby modulate its activity. The present invention relates to these antibodies and to other related antibodies that are derived from these antibodies or have similar binding properties to these antibodies.

Accordingly, the present invention relates to antibodies that specifically bind to tissue factor pathway inhibitor (TFPI) and that reduce clotting time in, for example, (a) human FVIII-deficient plasma and/or (b) human whole blood.

One antibody comprises the light chain variable region of SEQ ID NO: 4 and the heavy chain variable region of SEQ ID NO: 8. Another antibody comprises the light chain variable region of SEQ ID NO: 15 and the heavy chain variable region of SEQ ID NO: 18.

The invention also provides polynucleotides which encode an antibody of the invention, such as polynucleotides which encode an antibody light chain and/or an antibody heavy chain of the invention.

The invention also provides pharmaceutical compositions comprising an antibody or polynucleotide of the invention and a pharmaceutically acceptable carrier or diluent.

The antibodies, polynucleotides and compositions of the invention are also provided for use in (a) the treatment or prevention of a coagulopathy (bleeding disorder) or (b) the stimulation of blood clotting. That is, the invention provides a method for (a) the treatment or prevention of a coagulopathy (bleeding disorder) or (b) the stimulation of blood clotting, the method comprising administering to a patient in need thereof a therapeutically or prophylactically effective amount of an antibody, polynucleotide or composition of the invention.

Furthermore, the invention provides dosing regimens of said monoclonal antibody of the invention.

BRIEF DESCRIPTION OF THE FIGURES

FIG. 1 shows the sequences of VH (A) and VL (B) domains of mouse anti-TFPI4F36A1B2 (herein also referred to as MuTFPI4F36 or 4F36), aligned with the sequences for the human germline and the initial CDR grafted version of humanized TFPI4F36. The Kabat numbering scheme is indicated above the sequences.

FIG. 2 shows the nucleotide sequences and translated polypeptide sequences for the VH and VL sequences of the murine antibody TFPI4F36A1B2 (MuTFPI4F36).

FIG. 3 shows the amino acid sequences of the light (A) and heavy (B) chains of Fab fragments of the murine 4F36 antibody, MuTFPI4F36. Numbering above the sequences is shown according to Kabat. Positions corresponding to CDR loops are highlighted in bold underlined text in the Kabat numbering. Amino acid residues constituting the paratope are highlighted in bold underlined text. The paratope is determined from the X-ray structure of the complex between the MuTFPI4F36 Fab and the TFPI K2 domain and is defined as residues in the Fab having a heavy atom within a distance of less than 4 Å from a heavy atom in K2.

FIG. 4 shows the sequence of TFPI (signal peptide sequence omitted). The Kunitz domains are shown in bold: TFPI Kunitz domain 1=amino acids 26 to 76; TFPI Kunitz domain 2=amino acids 97-147; TFPI Kunitz domain 3=amino acids 188-238. The C-terminal part of TFPI is shown in italics at amino acids 240 to 276.

BRIEF DESCRIPTION OF THE SEQUENCE LISTING

Figure 5:
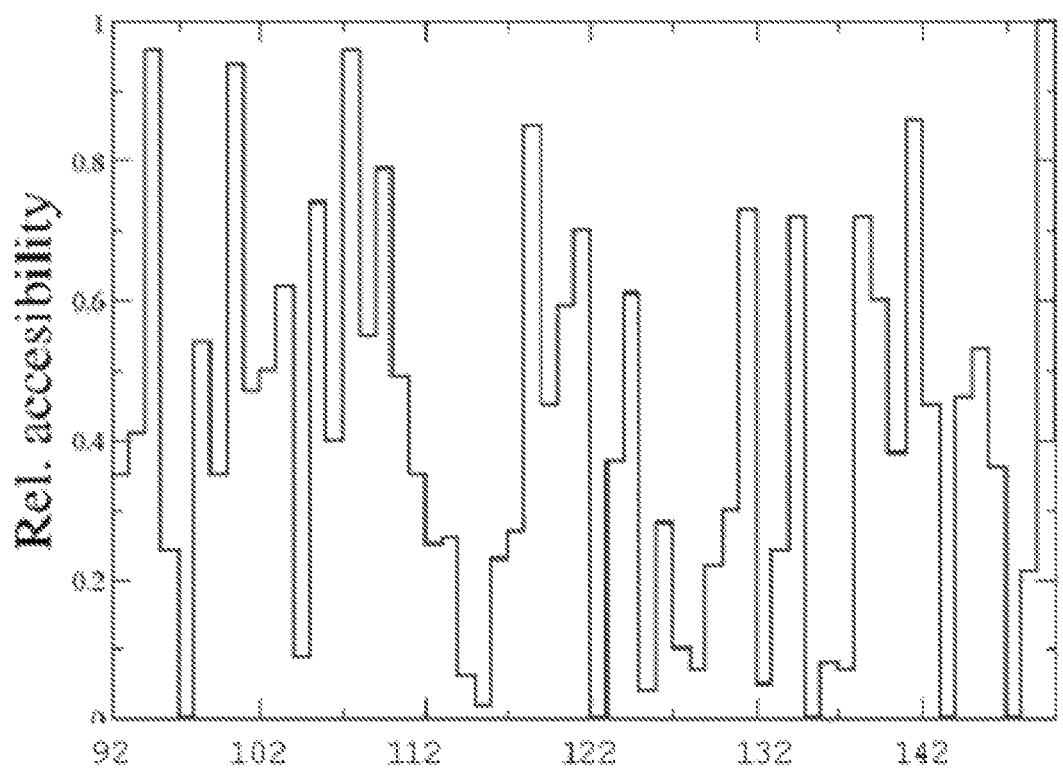
FIG. 5 shows the relative accessibility of residues in TFPI. The residues that have a greater than 40% accessibility are amino acids 94-95, 98, 100-110, 118-121, 123-124, 131, 134, 138-142 and 144-145.

SEQ ID NO: 1 gives the amino acid sequence of human TFPI (signal peptide sequence omitted).

SEQ ID NO: 2 gives the amino acid sequence of a construct used for determining the binding epitope of an antibody. The construct comprises amino acids 91 to 150 from human TFPI and a C-terminal $His_6$ tag.

SEQ ID NOs: 3, 5 and 4 give the polynucleotide (sense and anti-sense) and polypeptide sequences for the light chain variable domain (VL) of the MuTFPI4F36 (TFPI-4F36A1B2) monoclonal antibody. SEQ ID NO: 6 gives the amino acid sequence of the light chain of the MuTFPI4F36 (TFPI-4F36A1B2) monoclonal antibody. Signal peptide sequences are omitted.

SEQ ID NOs: 7, 9 and 8 give the polynucleotide (sense and anti-sense) and polypeptide sequences for the heavy chain variable domain (VH) of the MuTFPI4F36 (TFPI-4F36A1B2) monoclonal antibody. SEQ ID NO: 10 gives the amino acid sequence of the heavy chain of the MuTFPI4F36 (TFPI-4F36A1B2) monoclonal antibody. Signal peptide sequences are omitted.

SEQ ID NO: 11 gives the sequence of a reverse primer used for heavy chain variable domain amplification and SEQ ID NO: 12 gives the sequence of a reverse primer used for light chain amplification.

SEQ ID NOs: 13-15 provide the sense polynucleotide, anti-sense polynucleotide and polypeptide sequences, respectively, for the light chain variable domain (VL) of the humanized monoclonal antibody, HzTFPI4F36 (mAbTFPI2021). Signal peptide sequences are omitted.

SEQ ID NOs: 16-18 provide the sense polynucleotide, anti-sense polynucleotide and polypeptide sequences, respectively, for the heavy chain variable domain (VH) of the humanized monoclonal antibody, HzTFPI4F36 (mAbTFPI2021).

SEQ ID NOs: 19-21 provide the sense polynucleotide, anti-sense polynucleotide and polypeptide sequences, respectively, for the light chain (LC) of the humanized monoclonal antibody, HzTFPI4F36 (mAbTFPI2021).

SEQ ID NOs: 22-24 provide the sense polynucleotide, anti-sense polynucleotide and polypeptide sequences, respectively, for the heavy chain (HC) of the humanized monoclonal antibody, HzTFPI4F36 (mAbTFPI2021). Signal peptide sequences are omitted.

SEQ ID NOs: 25-26 provide the nucleic acid and amino acid sequences, respectively, for the light chain variable domain of the CDR-grafted HzTFPI4F36. Signal peptide sequences are omitted.

SEQ ID NOs: 27-28 provide the nucleic acid and amino acid sequences, respectively, of the heavy chain variable domain of the CDR-grafted HzTFPI4F36. Signal peptide sequences are omitted.

SEQ ID NO: 29 provides the amino acid sequence of the light chain of the CDR-grafted HzTFPI4F36 (human kappa chain). The signal peptide sequence is omitted.

SEQ ID NO: 30 provides the amino acid sequence of the heavy chain of the CDR-grafted HzTFPI4F36, which is a human IgG4 (S241P). The signal peptide sequence is omitted.

SEQ ID NO: 31 provides the germline sequence, VKII_A18/JK4, used for humanization of the light chain of MuTFPI4F36. The signal peptide sequence is omitted.

SEQ ID NO: 32 provides the germline sequence, VH3_21/JH6, used for humanization of the heavy chain of MuTFPI4F36. The signal peptide sequence is omitted.

SEQ ID NO: 33 provides the amino acid sequence of the MuTFPI4F36A1B2 heavy chain Fab. The signal peptide is omitted.

SEQ ID NO: 34 provides the amino acid sequence of the HzTFPI4F36 heavy chain Fab. The signal peptide is omitted.

DETAILED DESCRIPTION OF THE INVENTION

The present invention relates to antibodies that bind to TFPI. The antibodies preferably specifically bind to TFPI, i.e. they bind to TFPI but they do not bind, or bind at a lower affinity, to other molecules. In particular, the invention relates to antibodies that bind to TFPI and that modulate its activity. Antibodies of the invention may thus possess the ability to shorten clotting time. For example, an antibody of the invention may have the ability to shorten clotting time in human FVIII-deficient plasma or to reduce time to clot as measured in a thromboelastography (TEG) analysis of human whole blood. The invention also relates to uses for such antibodies, such as therapeutic and pharmaceutical uses.

The term TFPI as used herein encompasses any naturally occurring form of TFPI which may be derived from any suitable organism. For example, TFPI for use as described herein may be a mammalian TFPI, such as human, mouse, rat, primate, bovine, ovine, or porcine TFPI. Preferably the TFPI is human TFPI. The TFPI may be a mature form of TFPI such as a TFPI protein that has undergone post-translational processing within a suitable cell. Such a mature TFPI protein may, for example, be glycosylated. The TFPI may be a full length TFPI protein. The term TFPI also encompasses variants, isoforms and other homologs of such TFPI molecules. Variant TFPI molecules will generally be characterised by having the same type of activity as naturally occurring TFPI, such as the ability to neutralize the catalytic activity of FXa, or the ability to inhibit a complex of TF-FVIIa/FXa.

An antibody of the invention will have the ability to bind to TFPI. Preferably, an antibody of the invention will bind specifically to TFPI. That is, an antibody of the invention will preferably bind to TFPI with greater binding affinity than that at which it binds to another molecule. An antibody of the invention may have the ability to bind or specifically bind to a TFPI molecule as described herein such as any target molecule as described herein.

The term "binding affinity" is herein used as a measure of the strength of a non-covalent interaction between two molecules, e.g. and antibody, or fragment thereof, and an antigen. The term "binding affinity" is used to describe monovalent interactions (intrinsic activity).

Binding affinity between two molecules, e.g. an antibody, or fragment thereof, and an antigen, through a monovalent interaction may be quantified by determination of the dissociation constant ($K_D$). In turn, $K_D$ can be determined by measurement of the kinetics of complex formation and dissociation, e.g. by the SPR method (Biacore). The rate constants corresponding to the association and the dissociation of a monovalent complex are referred to as the association rate constants $k_a$ (or $k_{on}$) and dissociation rate constant $k_d$ (or $k_{off}$), respectively. $K_D$ is related to $k_a$ and $k_d$ through the equation $K_D = k_d/k_a$.

Following the above definition binding affinities associated with different molecular interactions, e.g. comparison of the binding affinity of different antibodies for a given antigen, may be compared by comparison of the $K_D$ values for the individual antibody/antigen complexes.

Similarly, the specificity of an interaction may be assessed by determination and comparison of the $K_D$ value for the interaction of interest, e.g. a specific interaction between an antibody and an antigen, with the $K_D$ value of an interaction not of interest.

Typically, the $K_D$ for the antibody with respect to the target will be 2-fold, preferably 5-fold, more preferably 10-fold less than $K_D$ with respect to the other, non-target molecule such as unrelated material or accompanying material in the environment. More preferably, the $K_D$ will be 50-fold less, such as 100-fold less, or 200-fold less; even more preferably 500-fold less, such as 1,000-fold less, or 10,000-fold less.

The value of this dissociation constant can be determined directly by well-known methods, and can be computed even for complex mixtures by methods such as those, for example, set forth in Caceci et al. (Byte 9:340-362, 1984). For example, the $K_D$ may be established using a double-filter nitrocellulose filter binding assay such as that disclosed by Wong & Lohman (Proc. Natl. Acad. Sci. USA 90, 5428-5432, 1993). Other standard assays to evaluate the binding ability of ligands such as antibodies towards targets are known in the art, including for example, ELISAs, Western blots, RIAs, and flow cytometry analysis. The binding kinetics and binding affinity of the antibody also can be assessed by standard assays known in the art, such as Surface Plasmon Resonance (SPR), e.g. by using a Biacore™ system.

A competitive binding assay can be conducted in which the binding of the antibody to the target is compared to the binding of the target by another ligand of that target, such as another antibody. The concentration at which 50% inhibition occurs is known as the Ki. Under ideal conditions, the Ki is equivalent to $K_D$. The Ki value will never be less than the $K_D$, so measurement of Ki can conveniently be substituted to provide an upper limit for $K_D$.

An antibody of the invention may have a $K_D$ for its target of $1\times10^{-7}$M or less, $1\times10^{-8}$M or less, or $1\times10^{-9}$M or less, or $1\times10^{-10}$M or less, $1\times10^{-11}$M or $1\times10^{-12}$M or less.

An antibody that specifically binds its target may bind its target with a high affinity, that is, exhibiting a low $K_D$ as discussed above, and may bind to other, non-target molecules with a lower affinity. For example, the antibody may bind to non-target molecules with a $K_D$ of $1\times10^{-6}$M or more, more preferably $1\times10^{-5}$ M or more, more preferably $1\times10^{-4}$ M or more, more preferably $1\times10^{-3}$ M or more, even more preferably $1\times10^{-2}$ M or more. An antibody of the invention is preferably capable of binding to its target with an affinity that is at least two-fold, 10-fold, 50-fold, 100-fold 200-fold, 500-fold, 1,000-fold or 10,000-fold or greater than its affinity for binding to another non-target molecule.

The target molecule may be any TFPI molecule as described herein, such as a naturally occurring TFPI molecule, a fully mature TFPI molecule or a full-length TFPI molecule. Preferred TFPI molecules are fully mature, naturally occurring, full length mammalian TFPI molecules. For example, the TFPI molecule may consist of, or may comprise, the amino acid sequence of SEQ ID NO: 1 or a fragment or other variant thereof as described herein.

The target molecule may be a variant of a TFPI molecule such as a fragment of a TFPI molecule. For example, the target molecule may be a fragment or other variant of TFPI which maintains a suitable epitope for antibody binding. For example, the target molecule may be a fragment or other variant of TFPI which retains an epitope as described herein. The target molecule may comprise such an epitope.

In one embodiment, the target molecule is a full length TFPI molecule. The full length TFPI molecule may comprise a first, second and third Kunitz domain as described herein. The full length TFPI molecule may comprise a first, second and third Kunitz domain as described herein and also a carboxy terminal region as described herein. The full length TFPI molecule may be a naturally occurring TFPI molecule such as a full length TFPI polypeptide as expressed from a TFPI gene, or as secreted by TFPI expressing cells. The full length TFPI molecule may be a naturally occurring TFPI molecule as found circulating in free form in plasma or bound to cells such as endothelial cells. The full length TFPI molecule is not a truncated TFPI molecule such as a naturally-occurring truncated TFPI molecule as described herein.

In one embodiment, the target molecule is a truncated TFPI molecule. For example, the truncated TFPI molecule may comprise a carboxy terminal truncation. For example, a number of naturally-occurring truncated forms of TFPI are known. These may comprise a truncation of part or all of the carboxy terminal part of TFPI. They may further comprise truncation of part or all of one or more of the Kunitz domains. For example, a truncated form of TFPI may comprise the deletion of the carboxy terminal part and part, or all, of the third Kunitz domain.

For example, one naturally occurring truncated form of TFPI comprises only amino acids 1 to 161 of the full length TFPI molecule (referred to herein as TFPI (1-161)). TFPI (1-161) is an active form of TFPI that has reduced activity compared with the full length molecule. TFPI (1-161) differs in structure from full length TFPI and antibodies generated against TFPI (1-161) as a target molecule may therefore differ from antibodies generated against full length TFPI.

A truncated form of TFPI may be an appropriate target molecule where it is desired to target antibodies against the region of full length TFPI that is present in TFPI (1-161). However, truncated TFPI is preferably used as a target molecule when antibodies are desired to be directed against specific truncated forms of TFPI such as naturally occurring truncated TFPI.

In one embodiment the target molecule is a naturally-occurring form of TFPI. This may be used in a form in which it is present in vivo. For example, the target molecule may be a full length naturally-occurring TFPI as discussed above.

The target molecule may be a truncated naturally-occurring TFPI as discussed above. The target molecule may be TFPI in a form in which it is present in plasma in vivo. The target molecule may be TFPI that is bound to lipoprotein in the same way as is present in plasma in vivo. The target molecule may be TFPI that is bound to cells in the same way as occurs in vivo, such as TFPI that is bound to endothelial cells. An antibody of the invention may bind to any one or more of these naturally occurring forms of TFPI. The antibody of the invention may be able to bind to all of these naturally occurring forms of TFPI, or may be able to discriminate between these different forms, binding to some but not others.

In one embodiment, the target molecule is, or comprises, the second Kunitz domain of TFPI. Such a target molecule may comprise amino acids 97 to 147 of SEQ ID NO: 1 or amino acids 91 to 150 of SEQ ID NO: 1 or an equivalent Kunitz domain 2 region from another TFPI polypeptide. Such a target molecule may comprise SEQ ID NO: 2 or amino acids 3 to 58 or 10 to 50 of SEQ ID NO: 2. The target molecule may be, or may comprise, a fragment of the second Kunitz domain of TFPI. For example, the target molecule may comprise five or more, eight or more, ten or more, twelve or more or fifteen or more amino acids from the second Kunitz domain.

The target molecule may comprise five or more, eight or more, ten or more, twelve or more or fifteen or more surface accessible residues of TFPI or of a particular region of TFPI such as a particular Kunitz domain or the C terminal part of TFPI. A surface accessible residue is a residue having more than 40% relative accessibility. For example, for the Kunitz 2 domain of TFPI (SEQ ID NO: 1), the following amino acids have a greater than 40% relative accessibility: 94-95, 98, 100-110, 118-121, 123-124, 131, 134, 138-142 and 144-145 (see FIG. 5). The target molecule may comprise five or more, eight or more, ten or more, twelve or more or fifteen or more of these residues, such as a fragment of TFPI that includes five or more, eight or more, ten or more, twelve or more or fifteen or more of these residues.

The target molecule may comprise a known epitope from TFPI.

The term "epitope", as used herein, is defined in the context of a molecular interaction between an "antigen binding polypeptide" (Ab) and its corresponding "antigen" (Ag). As used herein, the term Ab comprises an antibody or a fragment thereof, which specifically binds the corresponding Ag. Examples of antigen-binding fragments include Fab, Fab', F(ab)2, F(ab')2, F(ab)S, Fv (typically the VL and VH domains of a single arm of an antibody), single-chain Fv (scFv; see e.g., Bird et al., Science 1988; 242:42S-426; and Huston et al. PNAS 1988; 85:5879-5883), dsFv, Fd (typically the VH and CHI domain), and dAb (typically a VH domain) fragments; VH, VL, VhH, and V-NAR domains; monovalent molecules comprising a single VH and a single VL chain; minibodies, diabodies, triabodies, tetrabodies, and kappa bodies (see, e.g., Ill et al. Protein Eng 1997; 10:949-57); camel IgG; IgNAR; as well as one or more isolated CDRs or a functional paratope, where the isolated CDRs or antigen-binding residues or polypeptides can be associated or linked together so as to form a functional antibody fragment. Various types of antibody fragments have been described or reviewed in, e.g., Holliger and Hudson, Nat Biotechnol 2005;2S:1126-1136; WO2005040219, and published U.S. Patent Applications 20050238646 and 20020161201.

Antibody fragments can be obtained using conventional recombinant or protein engineering techniques, and the fragments can be screened for antigen-binding or other function in the same manner as are can be intact antibodies.

The term antigen (Ag) refers to the molecular entity used for immunization of an immunocompetent vertebrate to produce the antibody (Ab) that recognizes the Ag. Herein, Ag is termed more broadly and is generally intended to include target molecules that are specifically recognized by the Ab, thus including fragments or mimics of the molecule used in the immunization process for raising the Ab. Thus, for Ab's binding to the second kunitz domain (K2) of TFPI, both isolated K2, full-length TFPI including truncated and other variants of TFPI are referred to as an Ag.

Generally, the term "epitope" refers to the area or region on an Ag to which an Ab specifically binds, i.e. the area or region in physical contact with the Ab. A protein epitope may comprise amino acid residues in the Ag that are directly involved in binding to a Ab (also called the immunodominant component of the epitope) and other amino acid residues, which are not directly involved in the binding, such as amino acid residues of the Ag which are effectively blocked by the Ab (in other words, the amino acid residue is within the "solvent-excluded surface" and/or the "footprint" of the Ab). The term epitope herein includes both types of binding sites in any particular region of K2 in TFPI that specifically binds to an anti-TFPI antibody, or another K2-specific agent according to the invention, unless otherwise stated (e.g., in some contexts the invention relates to antibodies that bind directly to particular amino acid residues). K2 may comprise a number of different epitopes, which may include, without limitation, (1) linear peptide antigenic determinants, (2) conformational antigenic determinants which consist of one or more non-contiguous amino acids located near each other in the mature K2 conformation; and (3) post-translational antigenic determinants which consist, either in whole or part, of molecular structures covalently attached to K2, such as carbohydrate groups.

The epitope for a given antibody (Ab)/antigen (Ag) pair can be defined and characterized at different levels of detail using a variety of experimental and computational epitope mapping methods. The experimental methods include mutagenesis, X-ray crystallography, Nuclear Magnetic Resonance (NMR) spectroscopy, Hydroged deuterium eXchange Mass Spectrometry (HX-MS) and various competition binding methods. As each method relies on a unique principle the description of an epitope is intimately linked to the method by which it has been determined. Thus, the epitope for a given Ab/Ag pair will be defined differently depending on the epitope mapping method employed.

At its most detailed level, the epitope for the interaction between the Ag and the Ab can be defined by the spatial coordinates defining the atomic contacts present in the Ag-Ab interaction, as well as information about their relative contributions to the binding thermodynamics. At a less detailed level the epitope can be characterized by the spatial coordinates defining the atomic contacts between the Ag and Ab. At a further less detailed level the epitope can be characterized by the amino acid residues that it comprises as defined by a specific criterium, e.g. distance between atoms in the Ab and the Ag. At a further less detailed level the epitope can be characterized through function, e.g. by competition binding with other Abs. The epitope can also be defined more generically as comprising amino acid residues for which substitution by another amino acid will alter the characteristics of the interaction between the Ab and Ag.

In the context of an X-ray derived crystal structure defined by spatial coordinates of a complex between an Ab, e.g. a Fab fragment, and its Ag, the term epitope is herein, unless otherwise specified or contradicted by context, specifically defined as K2 residues characterized by having a heavy atom (i.e. a non-hydrogen atom) within a distance of 4 Å from a heavy atom in the Ab.

From the fact that descriptions and definitions of epitopes, dependant on the epitope mapping method used, are obtained at different levels of detail, it follows that comparison of epitopes for different Abs on the same Ag can similarly be conducted at different levels of detail.

Epitopes described on the amino acid level, e.g. determined from an X-ray structure, are said to be identical if they contain the same set of amino acid residues. Epitopes are said to overlap if at least one amino acid is shared by the epitopes. Epitopes are said to be separate (unique) if no amino acid residue are shared by the epitopes.

Epitopes characterized by competition binding are said to be overlapping if the binding of the corresponding Ab's are mutually exclusive, i.e. binding of one Ab excludes simultaneous binding of the other Ab. The epitopes are said to be separate (unique) if the Ag is able to accommodate binding of both corresponding Ab's simultaneously.

The definition of the term "paratope" is derived from the above definition of "epitope" by reversing the perspective. Thus, the term "paratope" refers to the area or region on the Ab to which an Ag specifically binds, i.e. to which it makes physical contact to the Ag.

In the context of an X-ray derived crystal structure defined by spatial coordinates of a complex between an Ab, e.g. a Fab fragment, and its Ag, the term paratope is herein, unless otherwise specified or contradicted by context, specifically defined as Ag residues characterized by having a heavy atom (i.e. a non-hydrogen atom) within a distance of 4 Å from a heavy atom in K2.

The epitope and paratope for a given antibody (Ab)/antigen (Ag) pair may be identified by routine methods. For example, the general location of an epitope may be determined by assessing the ability of an antibody to bind to different fragments or variant TFPI polypeptides. The specific amino acids within TFPI that make contact with an antibody (epitope) and the specific amino acids in an antibody that make contact with TFPI (paratope) may also be determined using routine methods, such as those described in the examples. For example, the antibody and target molecule may be combined and the Ab/Ag complex may be crystallised. The crystal structure of the complex may be determined and used to identify specific sites of interaction between the antibody and its target.

The present inventors have carried out such an analysis for the interaction between the murine MuTFPI4F36 antibody, as well as the humanised HzTFPI4F36 antibody, described herein, and the Kunitz 2 domain (K2) of TFPI. This analysis is described in more detail in the examples.

The paratope of an antibody according to the current invention may be defined as follows: the light chain of said antibody comprises residues E31, S32, D33, Y37, A96, T97, and F99 of SEQ ID NO: 15 and the heavy chain of said antibody comprises residues N31, S52, R53, S54, Y57, Y59, F60, P61, D62, Q65, Y102, D103 and D106 of SEQ ID NO 18.

The light chain of the antibody according to the current invention may thus comprise amino acid residues:
  E, in the position corresponding to position 31,
  S, in the position corresponding to position 32,
  D, in the position corresponding to position 33,
  Y, in the position corresponding to position 37,
  A, in the position corresponding to position 96,
  T, in the position corresponding to position 97 and
  F, in the position corresponding to position 99 of SEQ ID NO: 15;

and the heavy chain of said antibody may comprise amino acid residues:
  N, in the position corresponding to position 31,
  R, in the position corresponding to position 53,
  S, in the position corresponding to position 54,
  Y, in the position corresponding to position 57,
  Y, in the position corresponding to position 59,
  F, in the position corresponding to position 60,
  P, in the position corresponding to position 61,
  D, in the position corresponding to position 62,
  Q, in the position corresponding to position 65,
  Y, in the position corresponding to position 102,
  D, in the position corresponding to position 103 and
  D, in the position corresponding to position 106 of SEQ ID NO 18.

The heavy chain may further comprise an S in the position corresponding to position 52 of SEQ ID NO: 18.

The light chain of an antibody according to the current invention may further comprise an H in the position corresponding to position 98 of SEQ ID NO: 15 and the heavy chain may further comprise an S, in the position corresponding to position 56 of SEQ ID NO: 18.

For MuTFPI4F36 (Example 4) the epitope was found to be composed of amino acids E100, E101, P103, R107, Y109, T111, Y113, Q118, Q121, E123, R124, F125, K126 and L140 of SEQ ID NO: 1, corresponding to amino acids E10, E11, P13, R17, Y19, T21, Y23, Q28, Q31, E33, R34, F35, K36 and L50 of SEQ ID NO: 2. The paratope was found to be composed of light chain amino acid residues E31, S32, D33, Y37, A96, T97, H98 and F99 of SEQ ID NO: 4 and the heavy chain amino acid residues N31, R53, S54, S56, Y57, Y59, F60, P61, D62, Q65, Y102, D103 and D106 of SEQ ID NO 8.

For HzTFPI4F36 (Example 5) the epitope was found to be composed of amino acids E100, E101, D102, P103, R107, Y109, T111, Y113, F114, N116, Q118, Q121, C122, E123, R124, F125, K126 and L140 of SEQ ID NO: 1, corresponding to amino acids E10, E11, D12, P13, R17, Y19, T21, Y23, F24, N26, Q28, Q31, C32, E33, R34, K36 and L50 of SEQ ID NO: 2. The paratope was found to be composed of light chain amino acid residues E31, S32, D33, Y37, A96, T97 and F99 of SEQ ID NO: 15 and the heavy chain amino acid residues N31, S52, R53, S54, Y57, Y59, F60, P61, D62, Q65, Y102, D103 and D106 of SEQ ID NO 18.

An antibody according to the current invention may bind to the same epitope or domain of TFPI as the antibodies of the invention that are specifically disclosed herein. For example, other yet unidentified antibodies of the invention may be identified by comparing their binding to TFPI with that of the monoclonal antibodies, MuTFPI4F36 and/or HzTFPI4F36; or by comparing the function of yet unidentified antibodies with that of MuTFPI4F36 and/or HzTFPI4F36. Analyses and assays that may be used for the purpose of such identification include TFPI neutralizing assays such as: the FXa inhibition assay described in example 6 and the FVIIa/TF/FXa inhibition assay described in example 7; binding interaction analyses such as the surface plasmon resonance analysis described in example 8; cellular assays such as the neutralization of TFPI on human umbilical vascular endothelial cells (HUVECs), described in example 9, and the neutralization of TFPI inhibition of TF/FVIIa activity on MDA-MB 231 human breast carcinoma cells, described in example 10.

In one embodiment, an antibody of the invention may bind to the same epitope or region as the MuTFPI4F36 or HzTFPI4F36 antibodies described herein. The binding of MuTFPI4F36 and HzTFPI4F36 to TFPI is described in more detail herein. An antibody of the invention may be an antibody that binds to the same epitope in TFPI as the MuTFPI4F36 or HzTFPI4F36 antibodies. This may include it being in contact with the particular amino acids of TFPI as described above. For example, an antibody of the invention may bind to TFPI in such a way that it is in contact with amino acids E10, E11, P13, R17, Y19, T21, Y23, Q28, Q31, E33, R34, F35, K36 and L50 of SEQ ID NO: 2. or in such a way that it is in contact with amino acids E10, E11, D12, P13, R17, Y19, T21, Y23, F24, N26, Q28, Q31, C32, E33, R34, K36 and L50 of SEQ ID NO: 2.

An antibody of the invention may be capable of binding an epitope comprising one or more residues selected from the group consisting of E10, E11, D12, P13, R17, Y19, T21, Y23, F24, N26, Q28, Q31, C32, E33, R34, F35, K36 and L50 of SEQ ID NO: 2.

An antibody of the invention may be capable of binding an epitope comprising residue E10 of SEQ ID NO: 2.

An antibody of the invention may be capable of binding an epitope comprising residue E11 of SEQ ID NO: 2).

An antibody of the invention may be capable of binding an epitope comprising residue D12 of SEQ ID NO: 2.

An antibody of the invention may be capable of binding an epitope comprising residue P13 of SEQ ID NO: 2.

An antibody of the invention may be capable of binding an epitope comprising residue R17 of SEQ ID NO: 2.

An antibody of the invention may be capable of binding an epitope comprising residue Y19 of SEQ ID NO: 2.

An antibody of the invention may be capable of binding an epitope comprising residue T21 of SEQ ID NO: 2.

An antibody of the invention may be capable of binding an epitope comprising residue Y23 of SEQ ID NO: 2.

An antibody of the invention may be capable of binding an epitope comprising residue F24 of SEQ ID NO: 2.

An antibody of the invention may be capable of binding an epitope comprising residue N26 of SEQ ID NO: 2.

An antibody of the invention may be capable of binding an epitope comprising residue Q28 of SEQ ID NO: 2.

An antibody of the invention may be capable of binding an epitope comprising residue Q31 of SEQ ID NO: 2.

An antibody of the invention may be capable of binding an epitope comprising residue C32 of SEQ ID NO: 2.

An antibody of the invention may be capable of binding an epitope comprising residue E33 of SEQ ID NO: 2.

An antibody of the invention may be capable of binding an epitope comprising residue R34 of SEQ ID NO: 2.

An antibody of the invention may be capable of binding an epitope comprising residue F35 of SEQ ID NO: 2.

An antibody of the invention may be capable of binding an epitope comprising residue K36 of SEQ ID NO: 2.

An antibody of the invention may be capable of binding an epitope comprising residue L50 of SEQ ID NO: 2.

An antibody of the invention may be capable of binding an epitope comprising residues E10, E11, D12, P13, R17, Y19, T21, Y23, F24, N26, Q28, Q31, C32, E33, R34, K36 and L50 of SEQ ID NO: 2.

An antibody of the invention may be capable of binding an epitope comprising residues E10, E11, P13, R17, Y19, T21, Y23, Q28, Q31, E33, R34, F35, K36 and L50 of SEQ ID NO: 2.

An antibody of the invention may have the ability to compete with another antibody of the invention for binding to TFPI or another appropriate target as described herein. For example, an antibody of the invention may cross-compete with the MuTFPI4F36 or HzTFPI4F36 antibodies described herein for binding to TFPI, or to a suitable fragment or variant of TFPI that is bound by the MuTFPI4F36 or HzTFPI4F36 antibodies. Such cross-competing antibodies can be identified based on their ability to cross-compete with a known antibody of the invention in standard binding assays. For example, SPR e.g. by using a Biacore™ system, ELISA assays or flow cytometry may be used to demonstrate cross-competition. Such cross-competition may suggest that the two antibodies bind to identical, overlapping or similar epitopes.

Thus, the antibody of the invention may be capable of binding the K2 domain of TFPI with a higher affinity than any one or more of the following commercially available monoclonal antibodies: mAb0281 (Ab systems) and/or mAb4904 (American Diagnostica) and/or mAb2974 (R&D systems) and/or mAb29741 (R&D systems).

An antibody of the invention may therefore be identified by a method that comprises a binding assay which assesses whether or not a test antibody is able to compete with a known antibody of the invention for a binding site on the target molecule. Methods for carrying out competitive binding assays are well known in the art. For example they may involve binding a known antibody of the invention to a target molecule using conditions under which the antibody can bind to the target molecule. The antibody/target complex may then be exposed to a test antibody and the extent to which the test antibody is able to displace the antibody of the invention from antibody/target complexes may be assessed. An alternative method may involve contacting a test antibody with a target molecule under conditions that allow for antibody binding, then adding an antibody of the invention that is capable of binding that target molecule and assessing the extent to which the antibody of the invention is able to displace the test antibody from antibody/target complexes.

The ability of a test antibody to inhibit the binding of an antibody of the invention to the target demonstrates that the test compound can compete with an antibody of the invention for binding to the target and thus that the test antibody binds to the same epitope or region on the TFPI protein as the known antibody of the invention. A test antibody that is identified as competing with a known antibody of the invention in such a method is also a potential antibody according to the present invention. The fact that the test antibody can bind TFPI in the same region as a known antibody of the invention and compete with the known antibody of the invention suggests that the test antibody may act as a ligand at the same binding site as the known antibody and that the test antibody may therefore mimic the action of the known antibody. This can be confirmed by assessing the activity of TFPI in the presence of the test compound as described herein.

The known antibody of the invention may be an antibody as described herein, such as the murine TFPI-4F36A1B2 (also referred to as 4F36 and as MuTFPI4F36) antibody, or any variant or fragment thereof as described herein that retains the ability to bind to TFPI, such as humanized TFPI-4F36A1B2 antibodies, one of which is herein referred to as HzTFPI4F36 (mAbTFPI 2021). An antibody of the invention may bind to the same epitope as the MuTFPI4F36 antibody as described herein or any variant or fragment thereof as described herein that retains the ability to bind to TFPI, such as HzTFPI4F36.

An antibody of the invention may bind an epitope that is identical to, overlaps, or is similar to the MuTFPI4F36 epitope that is further described in the examples. An antibody of the invention may bind to an epitope that is identical to, overlaps or is similar to the HzTFPI4F36 epitope that is further described in the examples. An antibody of the invention may bind, preferably specifically, one or more amino acid residues that belong to the epitopes of MuTFPI4F36 and/or HzTFPI4F36. For example, an antibody of the invention may bind to five or more, six or more, seven or more, eight or more or ten or more of the amino acid residues set out above for binding of MuTFPI4F36 or HzTFPI4F36. For example, when contacted with a polypeptide of SEQ ID NO: 2, an antibody of the invention may bind to the polypeptide and make contact with amino acids E10, E11, D12, P13, R17, Y19, T21, Y23, F24, N26, Q28, Q31, C32, E33, R34, F35, K36 and L50, or a subset of those amino acids, such as at least 2, at least 3, at least 4, at least 5, at least 6, at least 7, at least 8, at least 9, at least 10, at least 11, at least 12, at least 13, at least 14, at least 15, at least 16, at least 17 or at least 18 of those amino acids.

Specific binding may be assessed with reference to binding of the antibody to a molecule that is not the target. This comparison may be made by comparing the ability of an antibody to bind to the target and to another molecule. This comparison may be made as described above in an assessment of $K_D$ or Ki. The other molecule used in such a comparison may be any molecule that is not the target molecule. Preferably the other molecule is not identical to the target molecule. Preferably the target molecule is not a fragment of the target molecule.

The $K_D$ of an antibody of the current invention may be less than 0.8 nM, such as less than 0.7 nM, such as less than 0.6 nM, such as less than 0.5 nM, such as less than 0.4 nM, such as less than 0.3 nM, such as less than 0.2 nM, such as less than 0.1 nM, such as less than 0.05 nM, such as less than 0.025 nM, such as less than 0.015 nM, such as between 0.015 nM and 0 nM.

The other molecule used to determine specific binding may be unrelated in structure or function to the target. For example, the other molecule may be an unrelated material or accompanying material in the environment.

The other molecule used to determine specific binding may be another molecule involved in the same in vivo pathway as the target molecule. For example, where the target is TFPI or a fragment or variant thereof, the other molecule used for comparison may be a protein that forms part of the blood coagulation cascade. By ensuring that the antibody of the invention has specificity for TFPI over another such molecule, unwanted in vivo cross-reactivity may be avoided.

The other molecule used for comparison may be related to the target molecule. For example, where it is desired to identify an antibody that binds only to a specific epitope, the other molecule for comparison may be a TFPI molecule in which that epitope is lacking or disrupted. The other molecule used for comparison may thus be another target molecule that is different to the target molecule bound by the antibody in question.

The antibody of the invention may retain the ability to bind to some molecules that are related to the target molecule. For example, a full-length mature human TFPI may be used as the target, but the antibody may also be able to bind to, e.g. immature forms of human TFPI, fragments or truncated forms of human TFPI, TFPI that is bound to lipoprotein or to a cell or TFPI from other species, such as other mammalian TFPI.

Alternatively, the antibody of the invention may have specificity for a particular target molecule. For example, it may bind to one target molecule as described herein, but may not bind, or may bind with significantly reduced affinity to a different target molecule as described herein. For example, a full length mature human TFPI may be used as the target, but the antibody that binds to that target may be unable to bind to or may bind with lesser affinity to, e.g. immature forms of human TFPI, fragments or truncated forms of human TFPI, TFPI that is bound to lipoprotein or to a cell or TFPI from other species, such as other mammalian TFPI.

An antibody of the invention may bind to TFPI and in doing so may inhibit an activity of TFPI.

As explained above, TFPI downregulates blood coagulation. It does this by inhibiting the activity of FXa and by inhibiting the TF-FVIIa complex in the presence of FXa. The activity of TFPI that is inhibited by an antibody of the invention may be any of these activities or any downstream effect thereof. For example, an antibody of the invention may lead to an increase in blood coagulation, an increase in the presence or levels of FXa or an increased activity of TF-FVIIa. Preferably, an antibody of the invention reduces clotting time when contacted with (a) human FVIII deficient plasma or (b) human whole blood.

The measurement of TFPI activity may comprise assessing the activity of the TFPI in inhibiting coagulation or reducing clotting time in a blood sample. For example, such a method may comprise contacting TFPI with a sample of blood or a blood product such as plasma or serum that comprises blood coagulation factors under conditions in which coagulation should occur, and determining whether coagulation of the blood is inhibited or clotting time is reduced by the presence of the TFPI. The level of blood coagulation or clotting time in such a sample may then be compared to that in an equivalent sample in which a test antibody is also present. If the level of coagulation is increased or clotting time is reduced in the antibody sample, this suggests that the antibody is inhibiting the activity of TFPI in the sample.

Blood coagulation may be detected by looking for coagulation of the blood itself, of plasma, or for one or more characteristics of the coagulation cascade that lie downstream to the point of action of TFPI. For example, the method may assess levels of FXa or activation of TF-FVIIa in the sample.

Various other methods for assessing blood coagulation and clotting time are well known in the art. For example, any effect of an antibody on blood clotting time may be assessed using a dilute prothrombin time analysis (dPT analysis) as described in the examples. Briefly, human plasma is contacted with human thromboplastin. The time taken for the plasma to clot is measured in the presence and absence of the test antibody. A positive control may be used in such an analysis, such as addition of FVIIa (NovoSeven®) which would be expected to reduce clotting time. An antibody of the invention should be capable of reducing clotting time in such a method. Preferably, an antibody of the invention should be capable of reducing clotting time in a dose-dependent manner.

The antibody of the current invention may be capable of inhibiting TFPI in a plasma-based clot assay, such as a dPT analysis, significantly better than any one or more of the following commercially available monoclonal antibodies: mAb0281 (Ab systems) and/or mAb4904 (American Diagnostica) and/or mAb2974 (R&D systems) and/or mAb29741 (R&D systems).

Thromboelastography may be used to assess the kinetics of clot formation and fibrinolysis in samples of whole blood. The ability of an antibody to reduce clotting time or to stimulate blood coagulation may thus be similarly assessed in a whole blood sample by comparing the time taken for clot formation in the presence and absence of the antibody.

Methods to assess the functional effects of an antibody of the invention may thus be carried out in vitro. Such methods are preferably carried out on samples of human blood or plasma. Such samples may be normal human blood or plasma or may be deficient in, or supplemented with, one or more factors involved in blood coagulation. For example, these methods may be carried out using normal human whole blood, normal human plasma or FVIII-deficient plasma or whole blood. FVIII-deficient blood or plasma may be generated by contacting a suitable blood or plasma sample with neutralising anti-FVIII antibody. Such in vitro methods may be binding interaction analyses or TFPI neutralisation analyses, such as those described in examples 6-11.

The antibody of the current invention may be capable of inhibiting platelet-associated TFPI.

The antibody of the current invention may be capable of inhibiting soluble TFPI.

The antibody of the current invention may be capable of inhibiting lipoprotein-bound TFPI.

The antibody of the current invention may be capable of inhibiting cell-bound TFPI, such as TFPI that is bound to endothelial cells.

The antibody of the current invention may be capable of binding TFPI such that FXa retains its activity by at least 91%, such as at least 92%, such as at least 93%, such as at least 94%, such as at least 95%, such as at least 96%, such as at least 97%, such as at least 98%, such as at least 99%, such as 99-100% as measured in a FXa inhibition assay.

The antibody of the current invention may be capable of neutralising the TFPI inhibition of membrane-bound FVIIa/TF/FXa, when TFPI is saturated with said antibody, by at least 55%, such as at least 60%, such as at least 65%, such as at least 70%, such as at least 75%, such as at least 80%, such as at least 85%, such as at least 90%, such as at least 95%, such as up to 100%, such as 100%, as measured in a FVIIa/TF/FXa inhibitor assay.

Preferably, an antibody of the invention is capable of reducing clotting time and/or stimulating blood coagulation in a sample of (a) human whole blood, (b) human plasma, (c) FVIII-deficient human whole blood, (d) FVIII-deficient human plasma, (e) FIX-deficient human whole blood or (f) FIX-deficient human plasma.

Methods to determine the ability of an antibody to stimulate blood coagulation or reduce clotting time may also be carried out in vivo. For example, in vivo studies may be carried out in transient haemophilic rabbits as described in the examples. Briefly, rabbits may be made transient haemophilic by administration of anti-FVIII antibody. The test antibody may then be administered and cuticle bleed time and/or platelet number assessed. A reduction in cuticle bleed time in the presence of a test antibody indicates that the antibody is capable of reducing clotting time and stimulating blood coagulation. An antibody having such an effect may therefore be an antibody of the present invention.

The antibody of the current invention may be capable of binding the K2 domain of TFPI such that the percentage of free TFPI in a subject is reduced to less than 30%, such as less than 29%, such as less than 28%, such as less than 27%, such as less than 26%, such as less than 25%, such as less than 24%, such as less than 23%, such as less than 22%, such as less than 21%, such as less than 20%, such as less than 19%, such as less than 18%, such as less than 17%, such as less than 16%, such as less than 15%, such as less than 14%, such as less than 13%, such as less than 12%, such as less than 11%, such as less than 10%, such as less than 9%, such as less than 8%, such as less than 7%, such as less than 6%, such as less than 5%, such as less than 4%, such as less than 3%, such as less than 2%, such as less than 1%, such as 0%.

Furthermore, the antibody of the current invention may be capable of binding the K2 domain of TFPI such that the amount of free TFPI in a subject is reduced during the first 28 days, such as during the first 27 days, such as during the first 26 days, such as during the first 25 days, such as during the first 24 days, such as during the first 23 days, such as during the first 22 days, such as during the first 21 days, such as during the first 20 days, such as during the first 19 days, such as during the first 18 days, such as during the first 17 days, such as during the first 16 days, such as during the first 15 days, such as during the first 14 days, such as during the first 13 days, such as during the first 12 days, such as during the first 11 days, such as during the first 10 days, such as during the first 9 days, such as during the first 8 days, such as during the first 7 days, such as during the first 6 days, such as during the first 5 days, such as during the first 4 days, such as during the first 3 days, such as during the first 2 days, such as during the first day after administration of said monoclonal antibody to said subject.

An antibody of the present invention may also lead to no significant decrease in platelet numbers. In particular, an antibody of the invention may be capable of reducing clotting time and/or stimulating blood coagulation in a sample of (a) human whole blood, (b) human plasma, (c) FVIII-deficient human whole blood (d) FVIII-deficient human plasma, (e) FIX-deficient human whole blood or (f) FIX-deficient human plasma, or in an animal in vivo, without leading to any significant decrease in platelet numbers. Platelet numbers can be assessed in the same sample or animal as the other effects discussed above, or can be assessed separately. For example, platelet numbers can be assessed in a blood sample such as a sample of blood obtained from a patient or experimental animal. Platelet numbers may be assessed following administration of the antibody to a transient haemophilic rabbit as described above. Antibodies of the invention may be capable of reducing cuticle bleed time without leading to a concurrent decrease in platelet numbers, as exemplified by in vivo studies in transient haemophilic rabbits. A change in platelet numbers may be assessed by comparing platelet numbers before and after administration of the antibody or by comparing platelet numbers between a sample or animal treated with the antibody of interest and a control sample or animal not treated with that antibody. An antibody of the current invention may be capable of binding the K2 domain of TFPI, such that a subject's in vivo clotting time is reduced and said subject's platelet count is not significantly reduced. For example, said subject's platelet count may not fall to approximately 80%, such as approximately 75%, such as approximately 70%, such as approximately 65%, such as approximately 60%, such as approximately 55%, such as approximately 50%, such as approximately 45%, such as approximately 40%, such as approximately 35%, such as approximately 30%, such as approximately 25% of the original platelet count. Preferably, there will be no difference or no statistically significant difference in platelet numbers when making such comparisons. That is, the antibody of the invention will not have caused any decrease in platelet numbers.

The term "antibody" as referred to herein includes whole antibodies and any antigen binding fragment (i.e., "antigen-binding portion") or single chains thereof. An antibody refers to a glycoprotein comprising at least two heavy chains (HC) and two light chains (LC) inter-connected by disulfide bonds, or an antigen binding portion thereof. Each heavy chain is comprised of a heavy chain variable region (abbreviated herein as VH) and a heavy chain constant region (CH). Each light chain is comprised of a light chain variable region (abbreviated herein as VL) and a light chain constant region (CL). The variable regions of the heavy and light chains contain a binding domain that interacts with an antigen. The VH and VL regions can be further subdivided into regions of hypervariability, termed complementarity determining regions (CDR), interspersed with regions that are more conserved, termed framework regions (FR). The constant regions of the antibodies may mediate the binding of the immunoglobulin to host tissues or factors, including various cells of the immune system (e.g., effector cells) and the first component (C1q) of the classical complement system.

The term "complementarity-determining region" or "hypervariable region" when used herein refers to the amino acid residues of an antibody that are responsible for antigen binding. The complementarity-determining regions or "CDRs" are generally comprised of amino acid residues 24-34 (L1), 50-56 (L2) and 89-97 (L3) in the light-chain variable domain and 31-35 (H1), 50-65 (H2) and 95-102 (H3) in the heavy-chain variable domain; (Kabat et al. (1991) Sequences of Proteins of Immunological Interest, Fifth Edition, U.S. Department of Health and Human Services, NIH Publication No. 91-3242) and/or those residues from a "hypervariable loop" (residues 26-32 (L1), 50-52 (L2) and 91-96 (L3) in the light-chain variable domain and 26-32 (H1), 53-55 (H2) and 96-101 (H3) in the heavy-chain variable domain; Chothia and Lesk, J. Mol. Biol 1987; 196:901-917). Typically, the numbering of amino acid residues in this region is performed by the method described in Kabat et al., supra. Phrases such as "Kabat position", "Kabat residue", and "according to Kabat" herein refer to this numbering system for heavy chain variable domains or light chain variable domains. Using the Kabat numbering system, the actual linear amino acid sequence of a peptide may contain fewer or additional amino acids corresponding to a shortening of, or insertion into, a FR or CDR of the variable domain. For example, a heavy chain variable domain may include amino acid insertions (residue 52a, 52b and 52c according to Kabat) after residue 52 of CDR H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The term "framework region" or "FR" residues refer to those VH or VL amino acid residues that are not within the CDRs, as defined herein.

An antibody of the invention may be a monoclonal antibody or a polyclonal antibody. In one embodiment, an antibody of the invention is a monoclonal antibody. An antibody of the invention may be a chimeric antibody, a CDR-grafted antibody, a human or humanised antibody or an antigen binding portion of any thereof. For the production of both monoclonal and polyclonal antibodies, the experimental animal is a suitable a mammal such as, but not restricted to, a goat, rabbit, rat or mouse.

Polyclonal antibodies are antibodies that are derived from different B cell lines. A polyclonal antibody may comprise a mixture of different immunoglobulin molecules that are directed against a specific antigen. The polyclonal antibody may comprise a mixture of different immunoglobulin molecules that bind to one or more different epitopes within an antigen molecule. Polyclonal antibodies may be produced by routine methods such as immunisation of a suitable animal, with the antigen of interest. Blood may be subsequently removed from the animal and the immunoglobulin fraction purified.

Monoclonal antibodies are immunoglobulin molecules that are identical to each other and have a single binding specificity and affinity for a particular epitope. Monoclonal antibodies (mAbs) of the present invention can be produced by a variety of techniques, including conventional monoclonal antibody methodology e.g., the standard somatic cell hybridization technique of Kohler and Milstein (1975) Nature 256: 495, or viral or oncogenic transformation of B lymphocytes. The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

To generate hybridomas producing monoclonal antibodies of the invention, splenocytes and/or lymph node cells from immunized mice can be isolated and fused to an appropriate immortalized cell line, such as a mouse myeloma cell line. The resulting hybridomas can be screened for the production of antigen-specific antibodies. The antibody secreting hybridomas can be replated, screened again, and if still positive for suitable IgG, the monoclonal antibodies can be subcloned at least twice by limiting dilution. The stable subclones can then be cultured in vitro to generate small amounts of antibody in tissue culture medium for characterization.

The term "antigen-binding portion" of an antibody refers to one or more fragments of an antibody that retain the ability to specifically bind to an antigen, such as TFPI or another target protein as described herein. It has been shown that the antigen-binding function of an antibody can be performed by fragments of a full-length antibody. Examples of binding fragments encompassed within the term "antigen-binding portion" of an antibody include a Fab fragment, a $F(ab')_2$ fragment, a Fab' fragment, a Fd fragment, a Fv fragment, a dAb fragment and an isolated complementarity determining region (CDR). Single chain antibodies such as scFv and heavy chain antibodies such as VHH and camel antibodies are also intended to be encompassed within the term "antigen-binding portion" of an antibody. These antibody fragments may be obtained using conventional techniques known to those of skill in the art, and the fragments may be screened for utility in the same manner as intact antibodies.

An antibody of the invention may be prepared, expressed, created or isolated by recombinant means, such as (a) antibodies isolated from an animal (e.g., a mouse) that is transgenic or transchromosomal for the immunoglobulin genes of interest or a hybridoma prepared therefrom, (b) antibodies isolated from a host cell transformed to express the antibody of interest, e.g., from a transfectoma, (c) antibodies isolated from a recombinant, combinatorial antibody library, and (d) antibodies prepared, expressed, created or isolated by any other means that involve splicing of immunoglobulin gene sequences to other DNA sequences.

An antibody of the invention may be a human antibody or a humanised antibody. The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

Such a human antibody may be a human monoclonal antibody. Such a human monoclonal antibody may be produced by a hybridoma which includes a B cell obtained from a transgenic nonhuman animal, e.g., a transgenic mouse, having a genome comprising a human heavy chain transgene and a light chain transgene fused to an immortalized cell.

Human antibodies may be isolated from sequence libraries built on selections of human germline sequences further diversified with natural and synthetic sequence diversity.

Human antibodies may be prepared by in vitro immunisation of human lymphocytes followed by transformation of the lymphocytes with Epstein-Barr virus.

The term "human antibody derivatives" refers to any modified form of the human antibody, e.g., a conjugate of the antibody and another agent or antibody.

The term "humanized antibody" is intended to refer to a human/non-human chimeric antibody that contains a minimal sequence (CDR regions) derived from non-human immunoglobulin. Humanized antibodies are thus human immunoglobulins (recipient antibody) in which residues from a hyper-variable region of the recipient are replaced by residues from a hypervariable region of a non-human species (donor antibody) such as mouse, rat, rabbit, or non-human primate hav-ing the desired specificity, affinity, and capacity. In some instances, FR residues of the human immunoglobulin are replaced by corresponding non-human residues. An example of such a modification is the introduction of one or more so-called back-mutations, such as is described in example 2. Furthermore, humanized antibodies may comprise residues that are not found in the recipient antibody or in the donor antibody. These modifications are made to further refine antibody performance. In general, a humanized antibody will comprise substantially all of at least one, and typically two, variable domains, in which all or substantially all of the hypervariable loops correspond to those of a non-human immunoglobulin and all or substantially all of the FR residues are those of a human immunoglobulin sequence. The humanized antibody can optionally also comprise at least a portion of an immunoglobulin constant region (Fc), typically that of a human immunoglobulin.

Antibodies of the invention can be tested for binding to the target protein by, for example, standard ELISA or Western blotting. An ELISA assay can also be used to screen for hybridomas that show positive reactivity with the target protein. The binding specificity of an antibody may also be determined by monitoring binding of the antibody to cells expressing the target protein, for example by flow cytometry.

The specificity of an antibody of the invention for target protein may be further studied by determining whether or not the antibody binds to other proteins. For example, where it is desired to produce an antibody that specifically binds TFPI or a particular part, e.g. epitope, of TFPI, the specificity of the antibody may be assessed by determining whether or not the antibody also binds to other molecules or modified forms of TFPI that lack the part of interest.

As explained above, antibodies of the invention may modify the activity of TFPI. Antibodies having the required binding properties may thus be further tested to determine their effects on the activity of TFPI. Thus, methods may be used to identify suitable antibodies that are capable of binding to TFPI and that are capable of modifying, and in particular reducing, its activity.

Once a suitable antibody has been identified and selected, the amino acid sequence of the antibody may be identified by methods known in the art. The genes encoding the antibody can be cloned using specific and/or degenerate primers. The antibody may be recombinantly produced by routine methods.

A "polypeptide" is used herein in its broadest sense to refer to a compound of two or more subunit amino acids, amino acid analogs, or other peptidomimetics. The term "polypeptide" thus includes short peptide sequences and also longer polypeptides and proteins. As used herein, the term "amino acid" may refer to natural and/or unnatural or synthetic amino acids, D and/or L optical isomers, and amino acid analogs and peptidomimetics.

The present inventors have identified a murine antibody as described in the examples. This antibody is referred to herein as TFPI-4F36A1B2 (alternatively, 4F36 or MuTFPI4F36). The present invention encompasses this antibody, variants and fragments thereof—including chimeric antibodies and humanised antibodies—which retain one or more activities of the murine antibody and which are also described in the examples. The activities of this antibody include the ability to bind to TFPI, the ability to bind to specific locations in the TFPI molecule and the ability to inhibit the activity of TFPI.

A suitable fragment or variant of this antibody will retain the ability to bind to TFPI. It will preferably retain the ability to specifically bind to TFPI. It will preferably retain the ability to specifically bind to the same or similar epitope or region of the TFPI molecule as the antibody (MuTFPI4F36) from which it is derived. It will preferably retain one or more additional functions of the antibody from which it is derived, such as the ability to inhibit TFPI activity or the ability to reduce clotting time, optionally without leading to a drop in platelet numbers.

Polypeptide or antibody "fragments" according to the invention may be made by truncation, e.g. by removal of one or more amino acids from the N and/or C-terminal ends of a polypeptide. Up to 10, up to 20, up to 30, up to 40 or more amino acids may be removed from the N and/or C terminal in this way. Fragments may also be generated by one or more internal deletions.

An antibody of the invention may be, or may comprise, a fragment of the MuTFPI4F36 antibody or a variant thereof. The antibody of the invention may be or may comprise an antigen binding portion of this antibody or a variant thereof as discussed further above. For example, the antibody of the invention may be a Fab fragment of this antibody or a variant thereof or may be a single chain antibody derived from this antibody or a variant thereof.

The amino acid sequences of the light and heavy chains of the MuTFPI4F36 antibody are given in SEQ ID NOs: 6 and 10 respectively. The amino acid sequences for the VL and VH chains of the MuTFPI4F36 antibody are given in SEQ ID NOs: 4 and 8 respectively. The amino acid sequences of the light and heavy chains of one humanised antibody, HzTFPI4F36, are given in SEQ ID NOs: 21 and 24, respectively. The amino acid sequences for the VL and VH chains of HzTFPI4F36 are given in SEQ ID NOs: 15 and 18, respectively.

An antibody of the invention may comprise the MuTFPI4F36 light chain amino acid sequence shown in SEQ ID NO: 6 or a fragment or variant thereof. An antibody may additionally or alternatively comprise the MuTFPI4F36 heavy chain amino acid sequence shown in SEQ ID NO: 10 or a fragment or variant thereof as described herein.

An antibody of the invention may comprise the VL amino acid sequence of SEQ ID No: 4, or a fragment or variant thereof. An antibody of the invention may comprise the VH amino acid sequence of SEQ ID No: 8, or a fragment or variant thereof. An antibody of the invention may comprise both (a) the VL amino acid sequence of SEQ ID No: 4, or a fragment or variant thereof and (b) the VH amino acid sequence of SEQ ID No: 8, or a fragment or variant thereof.

An antibody of the invention may comprise a fragment of one of the VL or VH amino acid sequences shown in FIG. 2. For example, an antibody of the invention may comprise a fragment of at least 7, at least 8, at least 9, at least 10, at least 12, at least 15, at least 18, at least 20 or at least 25 consecutive amino acids from SEQ ID No: 4 or 8. Such a fragment will preferably retain one or more of the functions discussed above, such as the ability to bind to TFPI.

A suitable fragment or variant of any of these VH or VL sequences will retain the ability to bind to TFPI. It will preferably retain the ability to specifically bind to TFPI. It will preferably retain the ability to specifically bind to the same or similar epitope or region of the TFPI molecule as the antibody (MuTFPI4F36) from which it is derived. It will preferably retain one or more additional functions of the antibody from which it is derived, such as the ability to inhibit TFPI activity or the ability to reduce clotting time, optionally without leading to a drop in platelet numbers.

A suitable fragment or variant VL sequence will preferably retain the amino acids at positions E31, S32, D33, Y37, A96, T97, H98 and F99 in SEQ ID NO: 4. A suitable fragment or variant VH sequence will preferably retain the amino acids at positions N31, R53, S54, S56, Y57, Y59, F60, P61, D62, Q65, Y102, D103 and D106 in SEQ ID NO: 8. A suitable fragment or variant antibody will preferably retain the amino acids at positions E31, S32, D33, Y37, A96, T97, H98 and F99 in SEQ ID NO: 4 and the amino acids at positions N31, R53, S54, S56, Y57, Y59, F60, P61, D62, Q65, Y102, D103 and D106 in SEQ ID NO: 8. As identified in FIG. 3, these are the residues in the MuTFPI4F36 light and heavy chain sequences that have a heavy atom within a distance of 4 Å from a heavy atom when MuTFPI4F36 is bound to the K2 domain of TFPI.

An antibody of the invention may comprise a CDR region from the specific antibody identified herein such as a CDR region from within SEQ ID NO: 4 or 8. Such an antibody will preferably retain the ability to bind to TFPI as described herein. For example, as shown in FIG. 3, using the Kabat definition, the CDR sequences within the light chain of MuTFPI4F36 may be identified at amino acids 24 to 39, 55 to 61 and 94 to 102 of SEQ ID NO: 4 or SEQ ID NO: 6. The CDR sequences within the heavy chain of MuTFPI4F36 may be identified at amino acids 31 to 35, 50 to 66 and 99 to 110 of SEQ IS NO: 8 or SEQ ID NO: 10. An antibody of the invention may comprise one or more of the CDR sequences shown in FIG. 3. For example, an antibody of the invention may comprise one, two or all three of the amino acid sequences shown at residues 24 to 39, 55 to 61 and 94 to 102 of SEQ ID NO: 6. An antibody of the invention may alternatively or additionally comprise one, two or all three of the amino acid sequences shown at residues 31 to 35, 50 to 66 and 99 to 110 of SEQ ID NO: 10. An antibody of the invention may comprise all six amino acid sequences shown at residues 24 to 39, 55 to 61 and 94 to 102 of SEQ ID NO: 6 and 31 to 35, 50 to 66 and 99 to 110 of SEQ ID NO: 10.

An antibody of the invention may be a humanized antibody, such as the antibody herein referred to as HzTFPI4F36 (mAbTFPI 2021). Such an antibody may comprise one or more CDR regions from within SEQ ID NO: 15 or 18.

The heavy chain of an antibody according to the invention may comprise a CDR1 sequence of amino acids 31 to 35 (NYAMS) of SEQ ID NO: 18, wherein one of these amino acids may be substituted by a different amino acid.

The heavy chain of an antibody according to the invention may comprise a CDR2 sequence of amino acids 50 to 66 (TISRSGSYSYFPDSVQG) of SEQ ID NO: 18, wherein one, two or three of these amino acids may be substituted by a different amino acid.

The heavy chain of an antibody according to the invention may comprise a CDR3 sequence of amino acids 99 to 110 (LGGYDEGDAMDS) of SEQ ID NO: 18, wherein one, two or three of these amino acids may be substituted by a different amino acid.

The light chain of an antibody according to the invention may comprise a CDR1 sequence of amino acids 24 to 39 (KSSQSLLESDGKTYLN) of SEQ ID NO: 15, wherein one, two or three of these amino acids may be substituted with a different amino acid.

The light chain of an antibody according to the invention may comprise a CDR2 sequence of amino acids 55 to 61 (LVSILDS) of SEQ ID NO: 15, wherein one or two of these amino acids may be substituted with a different amino acid.

The light chain of an antibody according to the invention may comprise a CDR3 sequence of amino acids 94 to 102 (LQATHFPQT) of SEQ ID NO: 15, wherein one or two of these amino acids may be substituted with a different amino acid.

More particularly, an antibody of the invention may have a heavy chain that comprises:
    a CDR1 sequence which, in turn, comprises amino acids 31 to 35 (NYAMS) of SEQ ID NO:18; and
    a CDR2 sequence which, in turn, comprises amino acids 50 to 66 (TISRSGSYSYFPDSVQG) of SEQ ID NO:18; and
    a CDR3 sequence which, in turn, comprises amino acids 99 to 110 (LGGYDEGDAMDS) of SEQ ID NO:18.

An antibody of the invention may have a light chain that comprises:
    a CDR1 sequence which, in turn, comprises amino acids 24 to 39 (KSSQSLLESDGKTYLN) of SEQ ID NO: 15; and
    a CDR2 sequence which, in turn, comprises amino acids 55 to 61 (LVSILDS) of SEQ ID NO: 15; and
    a CDR3 sequence which, in turn, comprises amino acids 94 to 102 (LQATHFPQT) of SEQ ID NO: 15.

An antibody of the invention may comprise any combination of the above CDR regions.

More particularly, framework region 2 (FR2) of the heavy chain of an antibody of the invention may comprise amino acids:
    T, in the position corresponding to position 40,
    E, in the position corresponding to position 42,
    R, in the position corresponding to position 44 and
    A, in the position corresponding to position 49 of SEQ ID NO: 18.

Alternatively, said FR2 of the heavy chain may comprise amino acids 36 to 49 of SEQ ID NO: 18.

An antibody of the invention may comprise any one of the following:
    the VL amino acid sequence of SEQ ID NO: 15.
    The VH amino acid sequence of SEQ ID NO: 18.
    SEQ ID NOs: 15 and 18.
    The light chain amino acid sequence of SEQ ID NO: 21.
    The heavy chain amino acid sequence of SEQ ID NO: 24.
    SEQ ID NOs: 21 and 24.

An antibody of the invention may alternatively be or may comprise a variant of one of these specific sequences such a variant of the MuTFPI4F36 antibody or a variant of HzTFPI4F36. For example, a variant may be a substitution, deletion or addition variant of any of the above amino acid sequences.

A variant according to the current invention may be an antibody that does not comprise:
    N, in the position corresponding to position 31 of the CDR1 region of SEQ ID NO: 18;
    R, in the position corresponding to position 53;
    S, in the position corresponding to position 54;
    S, in the position corresponding to position 56;
    Y, in the position corresponding to position 57;
    Y, in the position corresponding to position 59;

F, in the position corresponding to position 60;
P, in the position corresponding to position 61;
D, in the position corresponding to position 62; and
Q, in the position corresponding to position 65; of the CDR2 region of SEQ ID NO: 18.
Y, in the position corresponding to position 102;
D, in the position corresponding to position 103; and
D, in the position corresponding to position 106; of the CDR3 region of SEQ ID NO: 18.
E, in the position corresponding to position 31;
S, in the position corresponding to position 32;
D, in the position corresponding to position 33; and
Y, in the position corresponding to position 37; of the CDR1 region of SEQ ID NO: 15.
A, in the position corresponding to position 96;
T, in the position corresponding to position 97;
H, in the position corresponding to position 98; and
F, in the position corresponding to position 99; of the CDR3 region of SEQ ID NO: 15.

A variant antibody may comprise 1, 2, 3, 4, 5, up to 10, up to 20, up to 30 or more amino acid substitutions and/or deletions and/or insertions from the specific sequences and fragments discussed above. "Deletion" variants may comprise the deletion of individual amino acids, deletion of small groups of amino acids such as 2, 3, 4 or 5 amino acids, or deletion of larger amino acid regions, such as the deletion of specific amino acid domains or other features. "Insertion" variants may comprise the insertion of individual amino acids, insertion of small groups of amino acids such as 2, 3, 4 or 5 amino acids, or insertion of larger amino acid regions, such as the insertion of specific amino acid domains or other features. "Substitution" variants preferably involve the replacement of one or more amino acids with the same number of amino acids and making conservative amino acid substitutions. For example, an amino acid may be substituted with an alternative amino acid having similar properties, for example, another basic amino acid, another acidic amino acid, another neutral amino acid, another charged amino acid, another hydrophilic amino acid, another hydrophobic amino acid, another polar amino acid, another aromatic amino acid or another aliphatic amino acid. Some properties of the 20 main amino acids which can be used to select suitable substituents are as follows:

| Ala | aliphatic, hydrophobic, neutral | Met | hydrophobic, neutral |
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged (+) | Trp | aromatic, hydrophobic, neutral |
| Leu | aliphatic, hydrophobic, neutral | Tyr | aromatic, polar, hydrophobic |

Preferred "derivatives" or "variants" include those in which instead of the naturally occurring amino acid the amino acid which appears in the sequence is a structural analog thereof. Amino acids used in the sequences may also be derivatized or modified, e.g. labelled, providing the function of the antibody is not significantly adversely affected.

Substitutions may be, but are not limited to, conservative substitutions.

Derivatives and variants as described above may be prepared during synthesis of the antibody or by post-production modification, or when the antibody is in recombinant form using the known techniques of site-directed mutagenesis, random mutagenesis, or enzymatic cleavage and/or ligation of nucleic acids.

In another aspect, the present invention features multispecific molecules comprising an anti-TFPI antibody, or an antigen-fragment thereof, of the invention. Such multispecific molecules include bispecific molecules comprising at least one first binding specificity for TFPI and a second binding specificity for a second target epitope. One type of bispecific molecules are bispecific antibodies as known in the art. Bispecific antibodies, or indeed multispcific antibodies, may be prepared as full-length antibodies or antibody fragments (e.g. F(ab')2 bispecific antibodies) or any other antigen-binding fragments described herein.

In one aspect, the present invention features antibody derivatives (or immunoconjugates), such as anfi-TFPI antibodies conjugated or covalently bound to a second agent. The second agent can be linked to the antibody directly or indirectiy, using any of a large number of available methods known to the person skilled in the art. For example, an agent can be attached at the hinge region of the reduced antibody component via disulfide bond formafion, using cross-linkers such as N-succinyl S-(2-pyridyldithio)proprionate (SPDP), or via a carbohydrate moiety in the Fc region of the antibody.

In one aspect, antibodies of the invention may be engineered to include modifications within the Fc region, typically to alter one or more functional properties of the antibody, such as serum half-life, complement fixation, Fc receptor binding, protein stability and/or antigen-dependent cellular cytotoxicity, or lack thereof. Furthermore, an antibody of the invention may be chemically modified (e.g., one or more chemical moieties can be attached to the antibody) or be modified to alter its glycosylation, again to alter one or more functional properties of the antibody.

If desired, the class of an antibody may be "switched" by known techniques. For example, an antibody that was originally produced as an IgM molecule may be class switched to an IgG antibody. Class switching techniques also may be used to convert one IgG subclass to another, for example: from IgG1 to IgG2 or IgG4; from IgG2 to IgG1 or IgG4; or from IgG4 to IgG1 or IgG2. Engineering of antibodies to generate constant region chimeric molecules, by combination of regions from different IgG subclasses, can also be performed.

In one embodiment, the hinge region of CHI is modified such that the number of cysteine residues in the hinge region is altered, e.g., increased or decreased. This approach is described further for instance in U.S. Pat. No. 5,677,425 by Bodmer et al.

The constant region may further be modified to stabilize the antibody, e.g., to reduce the risk of a bivalent antibody separating into two monovalent VH-VL fragments. For example, in an IgG4 constant region, residue S241 may be mutated to a proline (P) residue to allow complete disulphide bridge formation at the hinge (see, e.g., Angal et al., Mol Immunol. 199S; 30:105-8).

Variant antibodies according to the invention may have amino acid sequences which are more than 60%, or more than 65%, or more than 70%, or more than 75%, or more than 80%, preferably more than 85%, such as more than 90%, such as more than 95% identical to SEQ ID NOs: 4 or 8, or fragments thereof. Other variant antibodies according to the invention may have amino acid sequences which are more than 60%, or more than 65%, or more than 70%, or more than 75%, or more than 80%, preferably more than 85%, such as more than 90%, such as more than 95% identical to SEQ ID NOs: 15 or 18, or a fragment thereof. This level of amino acid identity may be seen across the full length of the relevant SEQ ID NO sequence or over a part of the sequence, such as across 20, 30, 40, 50, 60, 70, 75, 80, 90, 100, 150, 200 or more amino acids, depending on the size of the full length polypeptide.

In connection with amino acid sequences, "sequence identity" refers to sequences which have the stated value when assessed using ClustalW (Thompson et al., 1994, supra) with the following parameters:

Pairwise alignment parameters—Method: accurate, Matrix: PAM, Gap open penalty: 10.00, Gap extension penalty: 0.10;

Multiple alignment parameters—Matrix: PAM, Gap open penalty: 10.00, % identity for delay: 30, Penalize end gaps: on, Gap separation distance: 0, Negative matrix: no, Gap extension penalty: 0.20, Residue-specific gap penalties: on, Hydrophilic gap penalties: on, Hydrophilic residues: GPSNDQEKR. Sequence identity at a particular residue is intended to include identical residues which have simply been derivatized.

The present invention thus provides antibodies having specific VH and VL amino acid sequences and variants and fragments thereof which maintain the function or activity of these VH and VL domains.

Accordingly, an antibody of the invention may comprise:
(a) a light chain variable region amino acid sequence of SEQ ID NO: 4;
(b) a fragment of at least 7 amino acids of (a) which retains the ability to specifically bind to TFPI; or
(c) a variant of (a) having at least 70% amino acid sequence identity to a sequence of (a) and retaining the ability to specifically bind to TFPI.

An antibody of the invention may comprise:
(a) a heavy chain variable region amino acid sequence of SEQ ID NO: 8;
(b) a fragment of at least 7 amino acids of (a) which retains the ability to specifically bind to TFPI; or
(c) a variant of (a) having at least 70% amino acid sequence identity to a sequence of (a) and retaining the ability to specifically bind to TFPI.

An antibody of the invention may comprise the light chain variable region of SEQ ID NO: 4 and the heavy chain variable region of SEQ ID NO: 8.

An antibody of the invention may comprise:
(a) the light chain variable region of SEQ ID NO: 4 and the heavy chain variable region of SEQ ID NO: 8;
(b) a variant of (a) in which one or both of the heavy chain and light chain sequences is modified such that it comprises a fragment of at least 7 amino acids of the sequence specified in (a); or
(c) a variant of (a) or (b) in which one or both of the heavy and light chain sequences is modified such that it has at least 70% amino acid sequence identity to a sequence of (a) or (b); wherein the antibody retains the ability to specifically bind to TFPI. The antibody may also retain one or more additional functions or activities of an antibody of the invention as described herein such as the ability to inhibit TFPI or the ability to shorten clotting time, optionally without leading to a drop in platelet numbers.

Preferred fragments and variants of SEQ ID NO: 4 will comprise (i) amino acids 24 to 39 of SEQ ID NO: 6; and/or (ii) amino acids 55 to 61 of SEQ ID NO: 6; and/or (iii) amino acids 94 to 102 of SEQ ID NO: 6. Preferred fragments and variants of SEQ ID NO: 8 will comprise (i) amino acids 31 to 35 of SEQ ID NO: 10; and/or (ii) amino acids 50 to 66 of SEQ ID NO: 10; and/or (iii) amino acids 99 to 110 of SEQ ID NO: 10.

Further preferred variants of SEQ ID NO: 4 will comprise amino acids 31 to 33, 37 and 96 to 99 of SEQ ID NO: 6. Further preferred variants of SEQ ID NO: 8 will comprise amino acids 31, 53, 54, 56, 57, 59, 60, 61, 62, 65, 102, 103 and 106 of SEQ ID NO: 10.

An antibody of the invention may comprise:
(a) a light chain variable region amino acid sequence of SEQ ID NO: 15;
(b) a fragment of at least 7 amino acids of (a) which retains the ability to specifically bind to TFPI; or
(c) a variant of (a) having at least 70% amino acid sequence identity to a sequence of (a) and retaining the ability to specifically bind to TFPI.

An antibody of the invention may comprise:
(a) a heavy chain variable region amino acid sequence of SEQ ID NO: 18;
(b) a fragment of at least 7 amino acids of (a) which retains the ability to specifically bind to TFPI; or
(c) a variant of (a) having at least 70% amino acid sequence identity to a sequence of (a) and retaining the ability to specifically bind to TFPI.

An antibody of the invention may comprise the light chain variable region of SEQ ID NO: 15 and the heavy chain variable region of SEQ ID NO: 18.

An antibody of the invention may comprise:
(a) the light chain variable region of SEQ ID NO: 15 and the heavy chain variable region of SEQ ID NO: 18;
(b) a variant of (a) in which one or both of the heavy chain and light chain sequences is modified such that it comprises a fragment of at least 7 amino acids of the sequence specified in (a); or
(c) a variant of (a) or (b) in which one or both of the heavy and light chain sequences is modified such that it has at least 70% amino acid sequence identity to a sequence of (a) or (b); wherein the antibody retains the ability to specifically bind to TFPI. The antibody may also retain one or more additional functions or activities of an antibody of the invention as described herein such as the ability to inhibit TFPI or the ability to shorten clotting time, optionally without leading to a drop in platelet numbers.

As explained above, an antibody of the invention may bind to the same epitope or region as another antibody of the invention. Thus it will be seen that such an antibody may bind to the same epitope or region of TFPI as any of the specific antibodies, fragments and variants described herein.

The invention also relates to polynucleotides that encode antibodies of the invention. Thus, a polynucleotide of the invention may encode any antibody as described herein. The terms "nucleic acid molecule" and "polynucleotide" are used interchangeably herein and refer to a polymeric form of nucleotides of any length, either deoxyribonucleotides or ribonucleotides, or analogs thereof. Non-limiting examples of polynucleotides include a gene, a gene fragment, messenger RNA (mRNA), cDNA, recombinant polynucleotides, plasmids, vectors, isolated DNA of any sequence, isolated RNA of any sequence, nucleic acid probes, and primers. A polynucleotide of the invention may be provided in isolated or purified form.

A nucleic acid sequence which "encodes" a selected polypeptide is a nucleic acid molecule which is transcribed (in the case of DNA) and translated (in the case of mRNA) into a polypeptide in vivo when placed under the control of appropriate regulatory sequences. The boundaries of the coding sequence are determined by a start codon at the 5' (amino)

terminus and a translation stop codon at the 3' (carboxy) terminus. For the purposes of the invention, such nucleic acid sequences can include, but are not limited to, cDNA from viral, prokaryotic or eukaryotic mRNA, genomic sequences from viral or prokaryotic DNA or RNA, and even synthetic DNA sequences. A transcription termination sequence may be located 3' to the coding sequence.

In one embodiment, a polynucleotide of the invention comprises a sequence which encodes a VH or VL amino acid sequence as described above. For example, a polynucleotide of the invention may encode a polypeptide comprising the sequence of SEQ ID NO: 4 or 8, or a variant or fragment thereof as described above. Such a polynucleotide may consist of or comprise a nucleic acid sequence of any one of SEQ ID NOs: 3, 5, 7 and 9. A suitable polynucleotide sequence may alternatively be a variant of one of these specific polynucleotide sequences. For example, a variant may be a substitution, deletion or addition variant of any of the above nucleic acid sequences. A variant polynucleotide may comprise 1, 2, 3, 4, 5, up to 10, up to 20, up to 30, up to 40, up to 50, up to 75 or more nucleic acid substitutions and/or deletions from the sequences given in the sequence listing.

Suitable variants may be at least 70% homologous to a polynucleotide of any one of SEQ ID NOs: 3, 5, 7 and 9 preferably at least 80 or 90% and more preferably at least 95%, 97% or 99% homologous thereto. Methods of measuring homology are well known in the art and it will be understood by those of skill in the art that in the present context, homology is calculated on the basis of nucleic acid identity. Such homology may exist over a region of at least 15, preferably at least 30, for instance at least 40, 60, 100, 200 or more contiguous nucleotides. Such homology may exist over the entire length of the unmodified polynucleotide sequence.

Methods of measuring polynucleotide homology or identity are known in the art. For example, the UWGCG Package provides the BESTFIT program which can be used to calculate homology (e.g. used on its default settings) (Devereux et al (1984) Nucleic Acids Research 12, p 387-395).

The PILEUP and BLAST algorithms can also be used to calculate homology or line up sequences (typically on their default settings), for example as described in Altschul S. F. (1993) J Mol Evol 36:290-300; Altschul, S, F et al (1990) J Mol Biol 215:403-10.

Software for performing BLAST analysis is publicly available through the National Centre for Biotechnology Information (http://www.ncbi.nlm.nih.gov/). This algorithm involves first identifying high scoring sequence pair (HSPS) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPS containing them. The word hits are extended in both directions along each sequence for as far as the cumulative alignment score can be increased. Extensions for the word hits in each direction are halted when: the cumulative alignment score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) Proc. Natl. Acad. Sci. USA 89:10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) Proc. Natl. Acad. Sci. USA 90:5873-5787. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The homologue may differ from a sequence in the relevant polynucleotide by less than 3, 5, 10, 15, 20 or more mutations (each of which may be a substitution, deletion or insertion). These mutations may be measured over a region of at least 30, for instance at least 40, 60 or 100 or more contiguous nucleotides of the homologue.

In one embodiment, a variant sequence may vary from the specific sequences given in the sequence listing by virtue of the redundancy in the genetic code. The DNA code has 4 primary nucleic acid residues (A, T, C and G) and uses these to "spell" three letter codons which represent the amino acids the proteins encoded in an organism's genes. The linear sequence of codons along the DNA molecule is translated into the linear sequence of amino acids in the protein(s) encoded by those genes. The code is highly degenerate, with 61 codons coding for the 20 natural amino acids and 3 codons representing "stop" signals. Thus, most amino acids are coded for by more than one codon—in fact several are coded for by four or more different codons. A variant polynucleotide of the invention may therefore encode the same polypeptide sequence as another polynucleotide of the invention, but may have a different nucleic acid sequence due to the use of different codons to encode the same amino acids.

Polynucleotide "fragments" according to the invention may be made by truncation, e.g. by removal of one or more nucleotides from one or both ends of a polynucleotide. Up to 10, up to 20, up to 30, up to 40, up to 50, up to 75, up to 100, up to 200 or more amino acids may be removed from the 3' and/or 5' end of the polynucleotide in this way. Fragments may also be generated by one or more internal deletions. Such fragments may be derived from a sequence of SEQ ID NOs: 3, 5, 7 and 9 or may be derived from a variant polynucleotide as described herein. Preferably such fragments are between 30 and 300 residues in length, e.g. 30 to 300, 30 to 200, 30 to 100, 100 to 200 or 200 to 300 residues. Alternatively, fragments of the invention may be longer sequences, for example comprising at least 50%, at least 60%, at least 70%, at least 80% or at least 90% of a full length polynucleotide of the invention.

An antibody of the invention may thus be produced from or delivered in the form of a polynucleotide which encodes, and is capable of expressing, it. Where the antibody comprises two or more chains, a polynucleotide of the invention may encode one or more antibody chains. For example, a polynucleotide of the invention may encode an antibody light chain, an antibody heavy chain or both. Two polynucleotides may be provided, one of which encodes an antibody light chain and the other of which encodes the corresponding antibody heavy chain. Such a polynucleotide or pair of polynucleotides may be expressed together such that an antibody of the invention is generated.

Polynucleotides of the invention can be synthesised according to methods well known in the art, as described by way of example in Sambrook et al (1989, Molecular Cloning—a laboratory manual; Cold Spring Harbor Press).

The nucleic acid molecules of the present invention may be provided in the form of an expression cassette which includes control sequences, signal peptide sequences operably linked to the inserted sequence, thus allowing for expression of the antibody of the invention in vivo. These expression cassettes, in turn, are typically provided within vectors (e.g., plasmids or recombinant viral vectors). Such an expression cassette may be administered directly to a host subject. Alternatively, a vector comprising a polynucleotide of the invention may be administered to a host subject. Preferably the polynucleotide is prepared and/or administered using a genetic vector. A suitable vector may be any vector which is capable of carrying a sufficient amount of genetic information, and allowing expression of a polypeptide of the invention.

The present invention thus includes expression vectors that comprise such polynucleotide sequences. Such expression vectors are routinely constructed in the art of molecular biology and may for example involve the use of plasmid DNA and appropriate initiators, promoters, enhancers, signal peptide sequences and other elements, such as for example polyadenylation signals which may be necessary, and which are positioned in the correct orientation, in order to allow for expression of a peptide of the invention. Other suitable vectors would be apparent to persons skilled in the art. By way of further example in this regard we refer to Sambrook et al.

The invention also includes cells that have been modified to express an antibody of the invention. Such cells include transient, or preferably stable higher eukaryotic cell lines, such as mammalian cells or insect cells, lower eukaryotic cells, such as yeast or prokaryotic cells such as bacterial cells. Particular examples of cells which may be modified by insertion of vectors or expression cassettes encoding for an antibody of the invention include mammalian HEK293, CHO, BHK, NSO and human retina cells. Preferably the cell line selected will be one which is not only stable, but also allows for mature glycosylation and cell surface expression of a polypeptide.

Such cell lines of the invention may be cultured using routine methods to produce an antibody of the invention, or may be used therapeutically or prophylactically to deliver antibodies of the invention to a subject. Alternatively, polynucleotides, expression cassettes or vectors of the invention may be administered to a cell from a subject ex vivo and the cell then returned to the body of the subject.

In another aspect, the present invention provides compositions and formulations comprising molecules of the invention, such as the antibodies, polynucleotides, vectors and cells described herein. For example, the invention provides a pharmaceutical composition comprising one or more molecules of the invention, such as one or more antibodies of the invention, formulated together with a pharmaceutically acceptable carrier.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for parenteral, e.g. intravenous, intramuscular or subcutaneous administration (e.g., by injection or infusion). Depending on the route of administration, the antibody may be coated in a material to protect the antibody from the action of acids and other natural conditions that may inactivate or denature the antibody.

Preferred pharmaceutically acceptable carriers comprise aqueous carriers or diluents. Examples of suitable aqueous carriers that may be employed in the pharmaceutical compositions of the invention include water, buffered water and saline. Examples of other carriers include ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. In many cases, it will be preferable to include isotonic agents, for example, sugars, polyalcohols such as mannitol, sorbitol, or sodium chloride in the composition.

A pharmaceutical composition of the invention also may include a pharmaceutically acceptable anti-oxidant. These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Therapeutic compositions typically must be sterile and stable under the conditions of manufacture and storage. The composition can be formulated as a solution, microemulsion, liposome, or other ordered structure suitable to high drug concentration.

Sterile injectable solutions can be prepared by incorporating the active agent (e.g. antibody) in the required amount in an appropriate solvent with one or a combination of ingredients enumerated above, as required, followed by sterilization microfiltration. Generally, dispersions are prepared by incorporating the active agent into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active agent plus any additional desired ingredient from a previously sterile-filtered solution thereof.

Pharmaceutical compositions of the invention may comprise additional active ingredients as well as an antibody of the invention. As mentioned above, compositions of the invention may comprise one or more antibodies of the invention. They may also comprise additional therapeutic or prophylactic agents. For example, where a pharmaceutical composition of the invention is intended for use in the treatment of a bleeding disorder, it may additionally comprise one or more agents intended to reduce the symptoms of the bleeding disorder. For example, the composition may comprise one or more clotting factors. The composition may comprise one or more other components intended to improve the condition of the patient. For example, where the composition is intended for use in the treatment of patients suffering from unwanted bleeding such as patients undergoing surgery or patients suffering from trauma, the composition may comprise one or more analgesic, anaesthetic, immunosuppressant or anti-inflammatory agents. Also falling within the scope of the present invention are kits comprising antibodies or other compositions of the invention and instructions for use. Such a kit may further contain one ore more additional reagents, such as an additional therapeutic or prophylactic agent as discussed above.

The antibodies, other molecules and compositions of the present invention have numerous in vitro and in vivo therapeutic utilities involving the treatment and prevention of clotting related disorders. For example, these antibodies and compositions can be administered to cells in culture, in vitro or ex vivo, or to human subjects, e.g., in vivo, to prevent or treat a variety of disorders.

In particular, the present invention provides methods for the treatment of bleeding disorders or for the enhancement of blood clotting comprising administering to a patient in need thereof an effective amount of an antibody or other molecule or composition of the invention. For example, such methods may be for the treatment of clotting factor deficiencies such as haemophilia A, haemophilia B, Factor XI deficiency, Factor VII deficiency, thrombocytopenia or von Willebrand's disease. Such methods may be for the treatment of conditions accompanied by the presence of a clotting factor inhibitor. Such methods may be for the treatment of excessive bleeding. The antibodies and compositions of the invention may be used to treat patients before, during, or after surgery or anticoagulant therapy or after trauma. The antibodies and compositions described herein may be used in any such treatment or may be used in the manufacture of a medicament for use in any such treatment.

The antibodies and compositions of the present invention may be administered for prophylactic/preventitive and/or therapeutic treatments.

In therapeutic applications, antibodies or compositions are administered to a subject already suffering from a disorder or condition as described above, in an amount sufficient to cure, alleviate or partially arrest the condition or one or more of its symptoms. Such therapeutic treatment may result in a decrease in severity of disease symptoms, or an increase in frequency or duration of symptom-free periods. An amount adequate to accomplish this is defined as "therapeutically effective amount". For example, where the treatment is for unwanted bleeding, therapy may be defined as a decrease in the amount of bleeding or suitable coagulation to stop the bleeding altogether.

In prophylactic or preventitive applications, antibodies or compositions are administered to a subject at risk of a disorder or condition as described above, in an amount sufficient to prevent or reduce the subsequent effects of the condition or one or more of its symptoms. An amount adequate to accomplish this is defined as a "prophylactically effective amount". For example, where the treatment is to prevent unwanted bleeding, a prophylactic effect may be defined as the prevention of bleeding or a reduced period or quantity of bleeding compared to that that would be seen in the absence of the modulator.

Effective amounts for each purpose will depend on the severity of the disease or injury as well as the weight and general state of the subject.

As used herein, the term "subject" includes any human or non-human animal. The term "non-human animal" includes all vertebrates, e.g., mammals and non-mammals, such as non-human primates, sheep, dogs, cats, horses, cows, chickens, amphibians, reptiles, etc.

An antibody or composition of the present invention may be administered via one or more routes of administration using one or more of a variety of methods known in the art. As will be appreciated by the skilled artisan, the route and/or mode of administration will vary depending upon the desired results. Preferred routes of administration for antibodies or compositions of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection. Alternatively, an antibody or composition of the invention can be administered via a non-parenteral route, such as a topical, epidermal or mucosal route of administration.

Similarly, an antibody of the invention may be used for the manufacture of a medicament suitable for parenteral administration.

An antibody of the invention may be used for the manufacture of a medicament suitable for intravenous administration.

An antibody of the invention may be used for the manufacture of a medicament suitable for intramuscular administration.

An antibody of the invention may be used for the manufacture of a medicament suitable for subcutaneous administration.

A suitable dosage of an antibody of the invention may be determined by a skilled medical practitioner. Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular antibody employed, the route of administration, the time of administration, the rate of excretion of the antibody, the duration of the treatment, other drugs, compounds and/or materials used in combination with the particular compositions employed, the age, sex, weight, condition, general health and prior medical history of the patient being treated, and like factors well known in the medical arts.

A suitable dose of an antibody of the invention may be, for example, in the range of from about 0.1 µg/kg to about 100 mg/kg body weight of the patient to be treated. For example, a suitable dosage may be from about 1 µg/kg to about 10 mg/kg body weight per day or from about 1 mg/kg to about 5 mg/kg body weight per day. A suitable dose of an antibody of the invention may be in the range of from 2 to 200 mg/kg, such as about 150-200 mg/kg, such as about 150-170 mg/kg, such as about 100-150 mg/kg, such as about 50-100 mg/kg, such as about 70-90 mg/kg, such as about 10-50 mg/kg, such as about 10-30 mg/kg.

Other suitable dosages may be approximately 0.1-10 mg/kg, such as approximately 0.1-1 mg/kg, such as approximately 1-2 mg/kg or approximately 2-3 mg/kg or approximately 4-5 mg/kg or approximately 5-6 mg/kg or approximately 6-7 mg/kg or approximately 7-8 mg/kg or approximately 8-9 mg/kg or approximately 9-10 mg/kg; or approximately 10-21 mg/kg, such as approximately 10-11 mg/kg, or approximately 11-12 mg/kg, or approximately 12-13 mg/kg, or approximately 13-14 mg/kg, or approximately 14-15 mg/kg, or approximately 15-16 mg/kg, or approximately 16-17 mg/kg, or approximately 17-18 mg/kg, or approximately 18-19 mg/kg, or approximately 19-20 mg/kg or approximately 20-21 mg/kg.

The amount of monoclonal antibody administered to a subject may be such that its administration results in a subject plasma concentration of about 10 µg/ml to about 40 µg/ml, such as about 15-35 µg/ml, such as about 10-15 µg/ml, such as about 15-20 µg/ml, such as about 20-25 µg/ml, such as about 25-30 µg/ml, such as about 30-35 µg/ml, such as about 35-40 µg/ml, of said monoclonal antibody. Dosage regimens may be adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Antibodies may be administered in a single dose or in multiple doses. The multiple doses may be administered via the same or different routes and to the same or different locations. Alternatively, antibodies can be administered as a sustained release formulation, in which case less frequent administration is required. Dosage and frequency may vary depending on the half-life of the antibody in the patient and the duration of treatment that is desired. The dosage and frequency of administration can also vary depending on whether the treatment is prophylactic or therapeutic. In prophylactic applications, a relatively low dosage may be administered at relatively infrequent intervals over a long period of time. In therapeutic applications, a relatively high dosage may be administered, for example until the patient shows partial or complete amelioration of symptoms of disease.

Thus, an antibody of the invention may be administered: approximately daily, approximately every other day, approximately every third day, approximately every fourth day, approximately every fifth day, approximately every sixth day; approximately every week, such as every 5, 6, 7, 8, 9 or 10 days; approximately every other week, such as every 11, 12, 13, 14, 15, 16 or 17 days; approximately every third week, such as every 18, 19, 20, 21, 22, 23 or 24 days; approximately every fourth week, such as every 25, 26, 27, 28, 29, 30 or 31 days. An antibody of the invention may also be administered on-demand.

As mentioned above, antibodies of the invention may be co-administered with one or other more other therapeutic agents. The other agent may be an agent that will enhance the effects of the modulator. The other agent may be an agent that acts to enhance blood coagulation, such as a blood coagulation factor. In particular, the modulators of the invention may be co-administered with Factor VII(a) or FVIII(a). The other agent may be intended to treat other symptoms or conditions of the patient. For example, the other agent may be an analgesic, anaesthetic, immunosuppressant or anti-inflammatory agent.

Combined administration of two or more agents may be achieved in a number of different ways. In one embodiment, the antibody and the other agent may be administered together in a single composition. In another embodiment, the antibody and the other agent may be administered in separate compositions as part of a combined therapy. For example, the modulator may be administered before, after or concurrently with the other agent.

The term "treatment", as used herein, refers to the medical therapy of any human or other animal subject in need thereof. Said subject is expected to have undergone physical examination by a medical practitioner or a veterinary medical practitioner, who has given a tentative or definitive diagnosis which would indicate that the use of said specific treatment is beneficial to the health of said human or other animal subject. The timing and purpose of said treatment may vary from one individual to another, according to the status quo of the subject's health. Thus, said treatment may be prophylactic, palliative, symptomatic and/or curative. In terms of the present invention, prophylactic, palliative, symptomatic and/or curative treatments may represent separate aspects of the invention.

Thus, an antibody of the invention may be administered parenterally.

An antibody of the invention may be administered intravenously.

An antibody of the invention may be administered intramuscularly.

An antibody of the invention may be administered subcutaneously.

An antibody of the invention may be administered prophylactically,

An antibody of the invention may be administered therapeutically (on demand).

An antibody of the invention may be capable of significantly reducing blood loss.

An antibody of the invention may be capable of significantly reducing bleeding time.

Thus, the invention is also a method of treating a subject in need thereof with a monoclonal antibody that is capable of binding the K2 domain of TFPI, wherein the amount of monoclonal antibody administered is such as to saturate its target. The amount of monoclonal antibody administered may be such as to saturate soluble TFPI. The amount of monoclonal antibody administered may be such as to saturate endothelium-bound TFPI.

The term "coagulopathy", as used herein, refers to an increased haemorrhagic tendency which may be caused by any qualitative or quantitative deficiency of any pro-coagulative component of the normal coagulation cascade, or any upregulation of fibrinolysis. Such coagulopathies may be congenital and/or acquired and/or iatrogenic and are identified by a person skilled in the art.

Non-limiting examples of congenital hypocoagulopathies are haemophilia A, haemophilia B, Factor VII deficiency, Factor XI deficiency, von Willebrand's disease and thrombocytopenias such as Glanzmann's thombasthenia and Bernard-Soulier syndrome.

A non-limiting example of an acquired coagulopathy is serine protease deficiency caused by vitamin K deficiency; such vitamin K-deficiency may be caused by administration of a vitamin K antagonist, such as warfarin. Acquired coagulopathy may also occur following extensive trauma. In this case otherwise known as the "bloody vicious cycle", it is characterised by haemodilution (dilutional thrombocytopaenia and dilution of clotting factors), hypothermia, consumption of clotting factors and metabolic derangements (acidosis). Fluid therapy and increased fibrinolysis may exaserbate this situation. Said haemorrhage may be from any part of the body.

Haemophilia A with "inhibitors" (that is, allo-antibodies against factor VIII) and haemophilia B with "inhibitors" (that is, allo-antibodies against factor IX) are non-limiting examples of coagulopathies that are partly congenital and partly acquired.

A non-limiting example of an iatrogenic coagulopathy is an overdosage of anticoagulant medication—such as heparin, aspirin, warfarin and other platelet aggregation inhibitors—that may be prescribed to treat thromboembolic disease. A second, non-limiting example of iatrogenic coagulopathy is that which is induced by excessive and/or inappropriate fluid therapy, such as that which may be induced by a blood transfusion.

In one embodiment of the current invention, haemorrhage is associated with haemophilia A or B. In another embodiment, haemorrhage is associated with haemophilia A or B with acquired inhibitors. In another embodiment, haemorrhage is associated with thrombocytopenia. In another embodiment, haemorrhage is associated with von Willebrand's disease. In another embodiment, haemorrhage is associated with severe tissue damage. In another embodiment, haemorrhage is associated with severe trauma. In another embodiment, haemorrhage is associated with surgery. In another embodiment, haemorrhage is associated with haemorrhagic gastritis and/or enteritis. In another embodiment, the haemorrhage is profuse uterine bleeding, such as in placental abruption. In another embodiment, haemorrhage occurs in organs with a limited possibility for mechanical haemostasis, such as intracranially, intraaurally or intraocularly. In another embodiment, haemorrhage is associated with anticoagulant therapy.

An antibody of the current invention may be used to treat a subject with a coagulopathy. Thus, the invention is also the use of a monoclonal antibody, that is capable of binding the K2 domain of TFPI, for the treatment of a subject in need thereof; as well as use of said antibody for the manufacture of a medicament for the treatment of a subject in need thereof. Furthermore, the invention is a method of treating a subject in need thereof with a monoclonal antibody that is capable of binding to the K2 domain of TFPI.

Use of said monoclonal antibody of the invention may significantly reduce blood loss.

Use of said monoclonal antibody of the invention may significantly reduce bleeding time.

Furthermore, use of said monoclonal antibody of the invention may reduce in vivo clotting time without causing transient thrombocytopaenia.

EMBODIMENTS

The following is a non-limiting list of embodiments of the present invention:

Embodiment 1: A monoclonal antibody that is capable of specifically binding the K2 domain of TFPI, wherein said antibody is capable of binding an epitope comprising one or more residues selected from the group consisting of E10, E11, D12, P13, R17, Y19, T21, Y23, F24, N26, Q28, Q31, C32, E33, R34, F35, K36 and L50 of SEQ ID NO: 2.

Embodiment 2: The monoclonal antibody according to embodiment 1, wherein said antibody is capable of specifically binding an epitope comprising an epitope comprising residue E10 of SEQ ID NO: 2.

Embodiment 3: The monoclonal antibody according to any one of the above embodiments, wherein said antibody is capable of specifically binding an epitope comprising an epitope comprising residue E11 of SEQ ID NO: 2.

Embodiment 4: The monoclonal antibody according to any one of the above embodiments, wherein said antibody is capable of specifically binding an epitope comprising residue D12 of SEQ ID NO: 2.

Embodiment 5: The monoclonal antibody according to any one of the above embodiments, wherein said antibody is capable of specifically binding an epitope comprising residue P13 of SEQ ID NO: 2.

Embodiment 6: The monoclonal antibody according to any one of the above embodiments, wherein said antibody is capable of specifically binding an epitope comprising residue R17 of SEQ ID NO: 2.

Embodiment 7: The monoclonal antibody according to any one of the above embodiments, wherein said antibody is capable of specifically binding an epitope comprising residue Y19 of SEQ ID NO: 2.

Embodiment 8: The monoclonal antibody according to any one of the above embodiments, wherein said antibody is capable of specifically binding an epitope comprising residue T21 of SEQ ID NO: 2.

Embodiment 9: The monoclonal antibody according to any one of the above embodiments, wherein said antibody is capable of specifically binding an epitope comprising residue Y23 of SEQ ID NO: 2.

Embodiment 10: The monoclonal antibody according to any one of the above embodiments, wherein said antibody is capable of specifically binding an epitope comprising residue F24 of SEQ ID NO: 2.

Embodiment 11: The monoclonal antibody according to any one of the above embodiments, wherein said antibody is capable of specifically binding an epitope comprising residue N26 of SEQ ID NO: 2.

Embodiment 12: The monoclonal antibody according to any one of the above embodiments, wherein said antibody is capable of specifically binding an epitope comprising residue Q28 of SEQ ID NO: 2.

Embodiment 13: The monoclonal antibody according to any one of the above embodiments, wherein said antibody is capable of specifically binding an epitope comprising residue Q31 of SEQ ID NO: 2.

Embodiment 14: The monoclonal antibody according to any one of the above embodiments, wherein said antibody is capable of specifically binding an epitope comprising residue C32 of SEQ ID NO: 2.

Embodiment 15: The monoclonal antibody according to any one of the above embodiments, wherein said antibody is capable of specifically binding an epitope comprising residue E33 of SEQ ID NO: 2.

Embodiment 16: The monoclonal antibody according to any one of the above embodiments, wherein said antibody is capable of specifically binding an epitope comprising residue R34 of SEQ ID NO: 2.

Embodiment 17: The monoclonal antibody according to any one of the above embodiments, wherein said antibody is capable of specifically binding an epitope comprising residue F35 of SEQ ID NO: 2.

Embodiment 18: The monoclonal antibody according to any one of the above embodiments, wherein said antibody is capable of specifically binding an epitope comprising residue K36 of SEQ ID NO: 2.

Embodiment 19: The monoclonal antibody according to any one of the above embodiments, wherein said antibody is capable of specifically binding an epitope comprising residue L50 of SEQ ID NO: 2.

Embodiment 20: The monoclonal antibody according to any one of embodiments 1-16 and 18-19, wherein said antibody is capable of specifically binding an epitope comprising residues E10, E11, D12, P13, R17, Y19, T21, Y23, F24, N26, Q28, Q31, C32, E33, R34, K36 and L50 of SEQ ID NO: 2.

Embodiment 21: The monoclonal antibody according to any one of embodiments 1-3, 5-9, 12-13 and 15-19, wherein said antibody is capable of specifically binding an epitope comprising residues E10, E11, P13, R17, Y19, T21, Y23, Q28, Q31, E33, R34, F35, K36 and L50 of SEQ ID NO: 2.

Embodiment 22: A monoclonal antibody that is capable of binding the K2 domain of TFPI, wherein the light chain of said antibody comprises amino acid residues:

E, in the position corresponding to position 31,
S, in the position corresponding to position 32,
D, in the position corresponding to position 33,
Y, in the position corresponding to position 37,
A, in the position corresponding to position 96,
T, in the position corresponding to position 97 and
F, in the position corresponding to position 99 of SEQ ID NO: 15;

and wherein the heavy chain of said antibody comprises amino acid residues:
- N, in the position corresponding to position 31,
- R, in the position corresponding to position 53,
- S, in the position corresponding to position 54,
- Y, in the position corresponding to position 57,
- Y, in the position corresponding to position 59,
- F, in the position corresponding to position 60,
- P, in the position corresponding to position 61,
- D, in the position corresponding to position 62,
- Q, in the position corresponding to position 65,
- Y, in the position corresponding to position 102,
- D, in the position corresponding to position 103 and
- D, in the position corresponding to position 106 of SEQ ID NO: 18.

Embodiment 23: A monoclonal antibody according to any of embodiments 1-21, wherein the light chain of said antibody comprises amino acid residues:
- E, in the position corresponding to position 31,
- S, in the position corresponding to position 32,
- D, in the position corresponding to position 33,
- Y, in the position corresponding to position 37,
- A, in the position corresponding to position 96,
- T, in the position corresponding to position 97 and
- F, in the position corresponding to position 99 of SEQ ID NO: 15;

and wherein the heavy chain of said antibody comprises amino acid residues:
- N, in the position corresponding to position 31,
- R, in the position corresponding to position 53,
- S, in the position corresponding to position 54,
- Y, in the position corresponding to position 57,
- Y, in the position corresponding to position 59,
- F, in the position corresponding to position 60,
- P, in the position corresponding to position 61,
- D, in the position corresponding to position 62,
- Q, in the position corresponding to position 65,
- Y, in the position corresponding to position 102,
- D, in the position corresponding to position 103 and
- D, in the position corresponding to position 106 of SEQ ID NO: 18.

Embodiment 24: The monoclonal antibody according to embodiment 22 or embodiment 23, wherein said heavy chain further comprises an S in the position corresponding to position 52 of SEQ ID NO: 18.

Embodiment 25: The monoclonal antibody according to any one of embodiments 22-23, wherein said light chain further comprises an H in the position corresponding to position 98 of SEQ ID NO: 15 and said heavy chain further comprises an S in the position corresponding to position 56 of SEQ ID NO: 18.

Embodiment 26: A monoclonal antibody that is capable of binding the Kunitz 2 (K2) domain of tissue factor pathway inhibitor (TFPI), wherein the heavy chain of said antibody comprises a CDR1 sequence of amino acids 31 to 35 (NYAMS) of SEQ ID NO:18, wherein one of these amino acids may be substituted by a different amino acid.

Embodiment 27: A monoclonal antibody according to any of embodiments 1 to 21 that is capable of binding the Kunitz 2 (K2) domain of tissue factor pathway inhibitor (TFPI), wherein the heavy chain of said antibody comprises a CDR1 sequence of amino acids 31 to 35 (NYAMS) of SEQ ID NO:18, wherein one of these amino acids may be substituted by a different amino acid.

Embodiment 28: A monoclonal antibody that is capable of binding the Kunitz 2 (K2) domain of tissue factor pathway inhibitor (TFPI), wherein the heavy chain of said antibody comprises a CDR2 sequence of amino acids 50 to 66 (TISRSGSYSYFPDSVQG) of SEQ ID NO: 18, wherein one, two or three of these amino acids may be substituted by a different amino acid.

Embodiment 29: A monoclonal antibody according to any of embodiments 1 to 21 that is capable of binding the Kunitz 2 (K2) domain of tissue factor pathway inhibitor (TFPI), wherein the heavy chain of said antibody comprises a CDR2 sequence of amino acids 50 to 66 (TISRSGSYSYFPDSVQG) of SEQ ID NO: 18, wherein one, two or three of these amino acids may be substituted by a different amino acid.

Embodiment 30: A monoclonal antibody that is capable of binding the Kunitz 2 (K2) domain of tissue factor pathway inhibitor (TFPI), wherein the heavy chain of said antibody comprises a CDR3 sequence of amino acids 99 to 110 (LGGYDEGDAMDS) of SEQ ID NO: 18, wherein one, two or three of these amino acids may be substituted by a different amino acid.

Embodiment 31: A monoclonal antibody according to any of embodiments 1 to 21 that is capable of binding the Kunitz 2 (K2) domain of tissue factor pathway inhibitor (TFPI), wherein the heavy chain of said antibody comprises a CDR3 sequence of amino acids 99 to 110 (LGGYDEGDAMDS) of SEQ ID NO: 18, wherein one, two or three of these amino acids may be substituted by a different amino acid.

Embodiment 32: A monoclonal antibody that is capable of binding the Kunitz 2 (K2) domain of tissue factor pathway inhibitor (TFPI), wherein the light chain of said antibody comprises a CDR1 sequence of amino acids 24 to 39 (KSSQSLLESDGKTYLN) of SEQ ID NO: 15, wherein one, two or three of these amino acids may be substituted with a different amino acid.

Embodiment 33: A monoclonal antibody according to any of embodiments 1 to 21 that is capable of binding the Kunitz 2 (K2) domain of tissue factor pathway inhibitor (TFPI), wherein the light chain of said antibody comprises a CDR1 sequence of amino acids 24 to 39 (KSSQSLLESDGKTYLN) of SEQ ID NO: 15, wherein one, two or three of these amino acids may be substituted with a different amino acid.

Embodiment 34: A monoclonal antibody that is capable of binding the Kunitz 2 (K2) domain of tissue factor pathway inhibitor (TFPI), wherein the light chain of said antibody comprises a CDR2 sequence of amino acids 55 to 61 (LVSILDS) of SEQ ID NO: 15, wherein one or two of these amino acids may be substituted with a different amino acid.

Embodiment 35: A monoclonal antibody according to any of embodiments 1 to 21 that is capable of binding the Kunitz 2 (K2) domain of tissue factor pathway inhibitor (TFPI), wherein the light chain of said antibody comprises a CDR2 sequence of amino acids 55 to 61 (LVSILDS) of SEQ ID NO: 15, wherein one or two of these amino acids may be substituted with a different amino acid.

Embodiment 36: A monoclonal antibody that is capable of binding the Kunitz 2 (K2) domain of tissue factor pathway inhibitor (TFPI), wherein the light chain of said antibody comprises a CDR3 sequence of amino acids 94 to 102 (LQATHFPQT) of SEQ ID NO: 15, wherein one or two of these amino acids may be substituted with a different amino acid.

Embodiment 37: A monoclonal antibody according to any of embodiments 1 to 21 that is capable of binding the Kunitz 2 (K2) domain of tissue factor pathway inhibitor (TFPI), wherein the light chain of said antibody comprises a CDR3 sequence of amino acids 94 to 102 (LQATHFPQT) of SEQ ID NO: 15, wherein one or two of these amino acids may be substituted with a different amino acid.

Embodiment 38: A monoclonal antibody that is capable of binding the Kunitz 2 (K2) domain of tissue factor pathway inhibitor (TFPI), wherein the heavy chain of said antibody comprises:
- a CDR1 sequence of amino acids 31 to 35 (NYAMS) of SEQ ID NO:18, wherein one of these amino acids may be substituted by a different amino acid; and/or
- a CDR2 sequence of amino acids 50 to 66 (TISRSGSYSYFPDSVQG) of SEQ ID NO:18, wherein one, two or three of these amino acids may be substituted by a different amino acid; and/or
- a CDR3 sequence of amino acids 99 to 110 (LGGYDEGDAMDS) of SEQ ID NO:18, wherein one, two or three of these amino acids may be substituted by a different amino acid.

Embodiment 39: A monoclonal antibody according to any of embodiments 1 to 21, wherein the heavy chain of said antibody comprises:
- a CDR1 sequence of amino acids 31 to 35 (NYAMS) of SEQ ID NO:18, wherein one of these amino acids may be substituted by a different amino acid; and/or
- a CDR2 sequence of amino acids 50 to 66 (TISRSGSYSYFPDSVQG) of SEQ ID NO:18, wherein one, two or three of these amino acids may be substituted by a different amino acid; and/or
- a CDR3 sequence of amino acids 99 to 110 (LGGYDEGDAMDS) of SEQ ID NO:18, wherein one, two or three of these amino acids may be substituted by a different amino acid.

Embodiment 40: A monoclonal antibody that is capable of binding the Kunitz 2 (K2) domain of tissue factor pathway inhibitor (TFPI), wherein the light chain of said antibody comprises:
- a CDR1 sequence of amino acids 24 to 39 (KSSQSLLESDGKTYLN) of SEQ ID NO: 15, wherein one, two or three of these amino acids may be substituted with a different amino acid; and/or
- a CDR2 sequence of amino acids 55 to 61 (LVSILDS) of SEQ ID NO: 15, wherein one or two of these amino acids may be substituted with a different amino acid; and/or
- a CDR3 sequence of amino acids 94 to 102 (LQATHFPQT) of SEQ ID NO: 15, wherein one or two of these amino acids may be substituted with a different amino acid.

Embodiment 41: A monoclonal antibody according to any of embodiments 1 to 21, wherein the light chain of said antibody comprises:
- a CDR1 sequence of amino acids 24 to 39 (KSSQSLLESDGKTYLN) of SEQ ID NO: 15, wherein one, two or three of these amino acids may be substituted with a different amino acid; and/or
- a CDR2 sequence of amino acids 55 to 61 (LVSILDS) of SEQ ID NO: 15, wherein one or two of these amino acids may be substituted with a different amino acid; and/or
- a CDR3 sequence of amino acids 94 to 102 (LQATHFPQT) of SEQ ID NO: 15, wherein one or two of these amino acids may be substituted with a different amino acid.

Embodiment 42: A monoclonal antibody that is capable of binding the Kunitz 2 (K2) domain of tissue factor pathway inhibitor (TFPI), wherein the heavy chain of said antibody comprises:
- a CDR1 sequence of amino acids 31 to 35 (NYAMS) of SEQ ID NO:18, wherein one of these amino acids may be substituted by a different amino acid; and/or
- a CDR2 sequence of amino acids 50 to 66 (TISRSGSYSYFPDSVQG) of SEQ ID NO:18, wherein one, two or three of these amino acids may be substituted by a different amino acid; and/or
- a CDR3 sequence of amino acids 99 to 110 (LGGYDEGDAMDS) of SEQ ID NO:18, wherein one, two or three of these amino acids may be substituted by a different amino acid;

and wherein the light chain of said antibody comprises:
- a CDR1 sequence of amino acids 24 to 39 (KSSQSLLESDGKTYLN) of SEQ ID NO: 15, wherein one, two or three of these amino acids may be substituted with a different amino acid; and/or
- a CDR2 sequence of amino acids 55 to 61 (LVSILDS) of SEQ ID NO: 15, wherein one or two of these amino acids may be substituted with a different amino acid; and/or
- a CDR3 sequence of amino acids 94 to 102 (LQATHFPQT) of SEQ ID NO: 15, wherein one or two of these amino acids may be substituted with a different amino acid.

Embodiment 43: A monoclonal antibody according to any of embodiments 1 to 21, wherein the heavy chain of said antibody comprises:
- a CDR1 sequence of amino acids 31 to 35 (NYAMS) of SEQ ID NO:18, wherein one of these amino acids may be substituted by a different amino acid; and/or
- a CDR2 sequence of amino acids 50 to 66 (TISRSGSYSYFPDSVQG) of SEQ ID NO:18, wherein one, two or three of these amino acids may be substituted by a different amino acid; and/or
- a CDR3 sequence of amino acids 99 to 110 (LGGYDEGDAMDS) of SEQ ID NO:18, wherein one, two or three of these amino acids may be substituted by a different amino acid;

and wherein the light chain of said antibody comprises:
- a CDR1 sequence of amino acids 24 to 39 (KSSQSLLESDGKTYLN) of SEQ ID NO: 15, wherein one, two or three of these amino acids may be substituted with a different amino acid; and/or
- a CDR2 sequence of amino acids 55 to 61 (LVSILDS) of SEQ ID NO: 15, wherein one or two of these amino acids may be substituted with a different amino acid; and/or
- a CDR3 sequence of amino acids 94 to 102 (LQATHFPQT) of SEQ ID NO: 15, wherein one or two of these amino acids may be substituted with a different amino acid.

Embodiment 44: A monoclonal antibody according to any one of embodiments 26-43, wherein said amino acid substitutions do not comprise amino acids:
- N, in the position corresponding to position 31 of the CDR1 region of SEQ ID NO: 18;
- R, in the position corresponding to position 53;
- S, in the position corresponding to position 54;
- S, in the position corresponding to position 56;
- Y, in the position corresponding to position 57;
- Y, in the position corresponding to position 59;
- F, in the position corresponding to position 60;
- P, in the position corresponding to position 61;
- D, in the position corresponding to position 62; and
- Q, in the position corresponding to position 65; of the CDR2 region of SEQ ID NO: 18.
- Y, in the position corresponding to position 102;
- D, in the position corresponding to position 103; and
- D, in the position corresponding to position 106; of the CDR3 region of SEQ ID NO: 18.
- E, in the position corresponding to position 31;
- S, in the position corresponding to position 32;

D, in the position corresponding to position 33; and
Y, in the position corresponding to position 37; of the CDR1 region of SEQ ID NO: 15.
A, in the position corresponding to position 96;
T, in the position corresponding to position 97;
H, in the position corresponding to position 98; and
F, in the position corresponding to position 99; of the CDR3 region of SEQ ID NO: 15.

Embodiment 45: The monoclonal antibody according to any one of embodiments 26-44, wherein said amino acid substitution is a conservative substitution.

Embodiment 46: The monoclonal antibody according to any one of embodiments 26-45, wherein the heavy chain of said antibody comprises:
a CDR1 sequence that comprises amino acids 31 to 35 (NYAMS) of SEQ ID NO:18; and
a CDR2 sequence that comprises amino acids 50 to 66 (TISRSGSYSYFPDSVQG) of SEQ ID NO:18; and
a CDR3 sequence that comprises amino acids 99 to 110 (LGGYDEGDAMDS) of SEQ ID NO:18.

Embodiment 47: The monoclonal antibody according to any one of embodiments 26-46, wherein the light chain of said antibody comprises:
a CDR1 sequence that comprises amino acids 24 to 39 (KSSQSLLESDGKTYLN) of SEQ ID NO: 15; and
a CDR2 sequence that comprises amino acids 55 to 61 (LVSILDS) of SEQ ID NO: 15; and
a CDR3 sequence that comprises amino acids 94 to 102 (LQATHFPQT) of SEQ ID NO: 15.

Embodiment 48: The monoclonal antibody according to any one of embodiments 46-47, wherein the heavy chain comprises:
a CDR1 sequence that comprises amino acids 31 to 35 (NYAMS) of SEQ ID NO:18; and
a CDR2 sequence that comprises amino acids 50 to 66 (TISRSGSYSYFPDSVQG) of SEQ ID NO:18; and
a CDR3 sequence that comprises amino acids 99 to 110 (LGGYDEGDAMDS) of SEQ ID NO:18;
and wherein the light chain comprises:
a CDR1 sequence that comprises amino acids 24 to 39 (KSSQSLLESDGKTYLN) of SEQ ID NO: 15; and
a CDR2 sequence that comprises amino acids 55 to 61 (LVSILDS) of SEQ ID NO: 15; and
a CDR3 sequence that comprises amino acids 94 to 102 (LQATHFPQT) of SEQ ID NO: 15.

Embodiment 49: The monoclonal antibody according to any one of the preceding embodiments, wherein the light chain of said antibody comprises SEQ ID NO: 15.

Embodiment 50: The monoclonal antibody according to any one of the preceding embodiments, wherein the heavy chain of said antibody comprises SEQ ID NO: 18.

Embodiment 51: The monoclonal antibody according to any one of the preceeding embodiments, wherein said antibody comprises SEQ ID NO: 15 and SEQ ID NO: 18.

Embodiment 52: The monoclonal antibody according to any one of the preceeding embodiments, wherein said antibody comprises the light chain of SEQ ID NO: 21.

Embodiment 53: The monoclonal antibody according to any one of the preceeding embodiments, wherein said antibody comprises the heavy chain of SEQ ID NO: 24.

Embodiment 54: The monoclonal antibody according to any one of embodiments 52-53, wherein said antibody comprises SEQ ID NO: 21 and SEQ ID NO: 24.

Embodiment 55: The monoclonal antibody according to any one of the preceding embodiments, which is a humanized antibody.

Embodiment 56: The monoclonal antibody according to embodiment 55, in which framework region 2 of the heavy chain comprises the amino acids:
T, in the position corresponding to position 40,
E, in the position corresponding to position 42,
R, in the position corresponding to position 44 and
A, in the position corresponding to position 49 of SEQ ID NO: 18.

Embodiment 57: The monoclonal antibody according to embodiment 55, in which framework region 2 of the heavy chain comprises the amino acids corresponding to positions 36 to 49 (WVRQTPEKRLEWVA) of SEQ ID NO: 18.

Embodiment 58: The monoclonal antibody according to any one of embodiments 1-54, which is a human antibody.

Embodiment 59: The monoclonal antibody according to any one of embodiments 1-54, which is a chimeric antibody Embodiment 60: The monoclonal antibody according to any one of the preceeding embodiments, wherein the isotype of said antibody is IgG.

Embodiment 61: The monoclonal antibody according to embodiment 60, wherein said isotype is IgG1, IgG2 or IgG4.

Embodiment 62: The monoclonal antibody according to embodiment 61, wherein the isotype of said antibody is IgG4.

Embodiment 63: The monoclonal antibody according to any one of embodiments 60-62, wherein at least one amino acid of the Fc region of said antibody has been substituted with another amino acid.

Embodiment 64: The monoclonal antibody according to any one of the preceding embodiments wherein the Fc region of said antibody is at least 80%, such as at least 85%, such as at least 90%, such as at least 95%, such as 95-100% identical amino acids 122-448 of SEQ ID NO: 24.

Embodiment 65: A monoclonal antibody, that is capable of binding the K2 domain of TFPI with a higher affinity than mAb0281.

Embodiment 66: The monoclonal antibody, according to any one of embodiments 1-64, that is capable of binding the K2 domain of TFPI with a higher affinity than mAb0281.

Embodiment 67: A monoclonal antibody, that is capable of binding the K2 domain of TFPI with a higher affinity than mAb4904.

Embodiment 68: A monoclonal antibody, according to any one of embodiments 1-66, that is capable of binding the K2 domain of TFPI with a higher affinity than mAb4904.

Embodiment 69: A monoclonal antibody, that is capable of binding the K2 domain of TFPI with a higher affinity than mAb2974.

Embodiment 70: A monoclonal antibody, according to according to any one of embodiments 1-68, that is capable of binding the K2 domain of TFPI with a higher affinity than mAb2974.

Embodiment 71: A monoclonal antibody, that is capable of binding the K2 domain of TFPI with a higher affinity than mAb29741.

Embodiment 72: A monoclonal antibody, according to according to any one of embodiments 1-70, that is capable of binding the K2 domain of TFPI with a higher affinity than mAb29741.

Embodiment 73: A monoclonal antibody, that is capable of binding the K2 domain of TFPI, wherein the $K_D$ of said antibody is less than 0.8 nM, such as less than 0.7 nM, such as less than 0.6 nM, such as less than 0.5 nM, such as less than 0.4 nM, such as less than 0.3 nM, such as less than 0.2 nM, such as less than 0.1 nM, such as less than 0.05 nM, such as less than 0.025 nM.

Embodiment 74: The monoclonal antibody, according to any one of embodiments 1-73, wherein the $K_D$ of said antibody is less than 0.8 nM, such as less than 0.7 nM, such as less than 0.6 nM, such as less than 0.5 nM, such as less than 0.4 nM, such as less than 0.3 nM, such as less than 0.2 nM, such as less than 0.1 nM, such as less than 0.05 nM, such as less than 0.025 nM.

Embodiment 75: The monoclonal antibody, according to any one of the above embodiments that is capable of binding the K2 domain of platelet-associated TFPI.

Embodiment 76: The monoclonal antibody, according to any of the above embodiments that is capable of inhibiting soluble TFPI.

Embodiment 77: The monoclonal antibody according to embodiment 76, wherein said soluble TFPI may be completely inhibited.

Embodiment 78: The monoclonal antibody, according to any of the above embodiments that is capable of inhibiting lipoprotein-bound TFPI.

Embodiment 79: The monoclonal antibody, according to any of the above embodiments that is capable of inhibiting endothelial cell-bound TFPI.

Embodiment 80: A monoclonal antibody, that is capable of binding the K2 domain of TFPI such that FXa retains its activity by at least 91%, such as at least 92%, such as at least 93%, such as at least 94%, such as at least 95%, such as at least 96%, such as at least 97%, such as at least 98%, such as at least 99%, such as 99-100%, as measured in a FXa inhibition assay.

Embodiment 81: The monoclonal antibody, according to any one of embodiments 1-79, that is capable of binding TFPI such that FXa retains its activity by at least 91%, such as at least 92%, such as at least 93%, such as at least 94%, such as at least 95%, such as at least 96%, such as at least 97%, such as at least 98%, such as at least 99%, such as 99-100% as measured in a FXa inhibition assay.

Embodiment 82: A monoclonal antibody, that is capable of binding the K2 domain of TFPI such that the percentage of free TFPI in a subject is reduced to less than 30%, such as less than 29%, such as less than 28%, such as less than 27%, such as less than 26%, such as less than 25%, such as less than 24%, such as less than 23%, such as less than 22%, such as less than 21%, such as less than 20%, such as less than 19%, such as less than 18%, such as less than 17%, such as less than 16%, such as less than 15%, such as less than 14%, such as less than 13%, such as less than 12%, such as less than 11%, such as less than 10%, such as less than 9%, such as less than 8%, such as less than 7%, such as less than 6%, such as less than 5%, such as less than 4%, such as less than 3%, such as less than 2%, such as less than 1%, such as between 1% and 0%.

Embodiment 83: A monoclonal antibody according to any one of embodiments 1-81, that is capable of binding the K2 domain of TFPI such that the percentage of free TFPI in a subject is reduced to less than 30%, such as less than 29%, such as less than 28%, such as less than 27%, such as less than 26%, such as less than 25%, such as less than 24%, such as less than 23%, such as less than 22%, such as less than 21%, such as less than 20%, such as less than 19%, such as less than 18%, such as less than 17%, such as less than 16%, such as less than 15%, such as less than 14%, such as less than 13%, such as less than 12%, such as less than 11%, such as less than 10%, such as less than 9%, such as less than 8%, such as less than 7%, such as less than 6%, such as less than 5%, such as less than 4%, such as less than 3%, such as less than 2%, such as less than 1%, such as between 1% and 0%.

Embodiment 84: The monoclonal antibody according to embodiment 83, wherein the amount of free TFPI in a subject is reduced to said percentage during the first 28 days, such as during the first 27 days, such as during the first 26 days, such as during the first 25 days, such as during the first 24 days, such as during the first 23 days, such as during the first 22 days, such as during the first 21 days, such as during the first 20 days, such as during the first 19 days, such as during the first 18 days, such as during the first 17 days, such as during the first 16 days, such as during the first 15 days, such as during the first 14 days, such as during the first 13 days, such as during the first 12 days, such as during the first 11 days, such as during the first 10 days, such as during the first 9 days, such as during the first 8 days, such as during the first 7 days, such as during the first 6 days, such as during the first 5 days, such as during the first 4 days, such as during the first 3 days, such as during the first 2 days, such as during the first day after administration of said monoclonal antibody to said individual.

Embodiment 85: A monoclonal antibody, that is capable of binding the K2 domain of TFPI and that is capable of neutralising the TFPI inhibition of membrane-bound FVIIa/TF/FXa by at least 55%, such as at least 60%, such as at least 65%, such as at least 70%, such as at least 75%, such as at least 80%, such as at least 85%, such as at least 90%, such as at least 95%, such as up to 100%, such as 100%, as measured in an FVIIa/TF/FXa inhibitor assay, when TFPI is saturated with said antibody.

Embodiment 86: The monoclonal antibody, according to any of embodiments 1-84, wherein said antibody is capable of neutralising the TFPI inhibition of membrane-bound FVIIa/TF/FXa by at least 55%, such as at least 60%, such as at least 65%, such as at least 70%, such as at least 75%, such as at least 80%, such as at least 85%, such as at least 90%, such as at least 95%, such as up to 100%, such as 100%, as measured in an FVIIa/TF/FXa inhibitor assay, when TFPI is saturated with said antibody.

Embodiment 87: A monoclonal antibody that is capable of binding the K2 domain of TFPI and that reduces in vivo clotting time without significantly reducing the platelet count.

Embodiment 88: The monoclonal antibody, according to any one of embodiments 1-86, wherein said antibody reduces in vivo clotting time without significantly reducing the platelet count.

Embodiment 89: The monoclonal antibody, according to embodiments 88, wherein said platelet count does not fall to approximately 80%, such as approximately 75%, such as approximately 70%, such as approximately 65%, such as approximately 60%, such as approximately 55%, such as approximately 50%, such as approximately 45%, such as approximately 40%, such as approximately 35%, such as approximately 30%, such as approximately 25% of the original platelet count.

Embodiment 90: A monoclonal antibody that is capable of binding the K2 domain of TFPI and that reduces in vivo clotting time without causing transient thrombocytopaenia.

Embodiment 91: The monoclonal antibody, according to any one of embodiments 1-89, wherein said antibody reduces in vivo clotting time without causing transient thrombocytopaenia.

Embodiment 92: A fragment of the monoclonal antibody according to any one of the preceding embodiments.

Embodiment 93: The fragment according to embodiment 92, which is a Fab fragment, a F(ab')₂ fragment, a Fab' fragment, a Fd fragment, a Fv fragment or a dAb fragment.

Embodiment 94: A variant of the monoclonal antibody according to any one of embodiments, which is a deletion variant or an insertion variant.

Embodiment 95: A pharmaceutical formulation comprising the monoclonal antibody according to any one of embodiments 1-94.

Embodiment 96: A pharmaceutical formulation comprising the monoclonal antibody according to any one of embodiments 1-94, wherein said formulation is suitable for parenteral use.

Embodiment 97: A pharmaceutical formulation comprising the monoclonal antibody according to any one of embodiments 1-94, wherein said antibody is suitable for intravenous use.

Embodiment 98: A pharmaceutical formulation comprising the monoclonal antibody according to any one of embodiments 1-94, wherein said antibody is suitable for intramuscular use.

Embodiment 99: A pharmaceutical formulation comprising the monoclonal antibody according to any one of embodiments 1-94, wherein said antibody is suitable for subcutaneous use.

Embodiment 100: Use of the monoclonal antibody according to any one of embodiments 1-94 for the manufacture of a medicament suitable for parenteral administration.

Embodiment 101: Use of the monoclonal antibody according to any one of embodiments 1-94 for the manufacture of a medicament suitable for intravenous administration.

Embodiment 102: Use of the monoclonal antibody according to any one of embodiments 1-94 for the manufacture of a medicament suitable for intramuscular administration.

Embodiment 103: Use of the monoclonal antibody according to any one of embodiments 1-94 for the manufacture of a medicament suitable for subcutaneous administration.

Embodiment 104: Use of a monoclonal antibody according to any one of embodiments 1-94, for the treatment of a subject with a coagulopathy.

Embodiment 105: Use according to embodiment 104, wherein said subject has any congenital, acquired and/or iatrogenic coagulopathy, such as may be selected from the group consisting of haemophilia A, with or without inhibitors, and haemophilia B, with or without inhibitors.

Embodiment 106: Use according to any one of embodiments 95-105, wherein said monoclonal antibody significantly reduces blood loss.

Embodiment 107: Use according to any one of embodiments 95-106, wherein said monoclonal antibody significantly reduces bleeding time.

Embodiment 108: Use according to any one of embodiments 95-107, wherein the amount of monoclonal antibody administered results in a plasma concentration of about 10 µg/ml to about 40 µg/ml, such as about 15-35 µg/ml, such as about 10-15 µg/ml, such as about 15-20 µg/ml, such as about 20-25 µg/ml, such as about 25-30 µg/ml, such as about 30-35 µg/ml, such as about 35-40 µg/ml, of said monoclonal antibody.

Embodiment 109: A method of treating a subject with a coagulopathy, comprising administering to said subject the monoclonal antibody according to any one of embodiments 1-94.

Embodiment 110: The method according to embodiment 109, wherein said coagulopathy is any congenital, acquired and/or iatrogenic coagulopathy, such as may be selected from the group consisting of haemophilia A, with or without inhibitors, and haemophilia B, with or without inhibitors.

Embodiment 111: The method according to any one of embodiments 109-110, wherein said monoclonal antibody is capable of significantly reducing blood loss.

Embodiment 112: The method according to any one of embodiments 109-111, wherein said monoclonal antibody is capable of significantly reducing bleeding time.

Embodiment 113: The method according to any one of embodiments 109-112, wherein the amount of monoclonal antibody administered is such as to saturate its target.

Embodiment 114: The method according to any one of embodiments 109-113, wherein the amount of monoclonal antibody administered is such as to saturate soluble TFPI.

Embodiment 115: The method according to any one of embodiments 109-114, wherein said administered antibody is capable of completely inhibiting soluble TFPI.

Embodiment 116: The method according to any one of embodiments 109-115, wherein said monoclonal antibody is administered in an amount sufficient to saturate endothelium-bound TFPI.

Embodiment 117: The method according to any one of embodiments 109-116, wherein the amount of monoclonal antibody administered results in a plasma concentration of about 10 µg/ml to about 40 µg/ml, such as about 15-35 µg/ml, such as about 10-15 µg/ml, such as about 15-20 µg/ml, such as about 20-25 µg/ml, such as about 25-30 µg/ml, such as about 30-35 µg/ml, such as about 35-40 µg/ml, of said monoclonal antibody.

Embodiment 118: The method according to any one of embodiments 109-117, wherein a single dose may be administered.

Embodiment 119: The method according to any one of embodiments 109-118, wherein multiple doses may be administered.

Embodiment 120: The method according to any one of embodiments 109-119, wherein said antibody may be administered daily.

Embodiment 121: The method according to any one of embodiments 109-120, wherein said antibody may be administered every other day.

Embodiment 122: The method according to any one of embodiments 109-121, wherein said antibody may be administered every third day.

Embodiment 123: The method according to any one of embodiments 109-122, wherein said antibody may be administered every fourth day.

Embodiment 124: The method according to any one of embodiments 109-123, wherein said antibody may be administered every fifth day.

Embodiment 125: The method according to any one of embodiments 109-124, wherein said antibody may be administered every sixth day.

Embodiment 126: The method according to any one of embodiments 109-125, wherein said monoclonal antibody may be administered approximately every week, such as every 5, 6, 7, 8, 9 or 10 days.

Embodiment 127: The method according to any one of embodiments 109-126, wherein said monoclonal antibody may be administered approximately every other week, such as every 11, 12, 13, 14, 15, 16 or 17 days.

Embodiment 128: The method according to any one of embodiments 109-127, wherein said monoclonal antibody may be administered approximately every third week, such as every 18, 19, 20, 21, 22, 23 or 24 days.

Embodiment 129: The method according to any one of embodiments 109-128, wherein said monoclonal antibody may be administered approximately every fourth week, such as every 25, 26, 27, 28, 29, 30 or 31 days.

Embodiment 130: The method according to any one of embodiments 109-129, wherein the dosage may be approximately 0.1-10 mg/kg, such as approximately 0.1-1 mg/kg, such as approximately 1-2 mg/kg or approximately 2-3 mg/kg or approximately 4-5 mg/kg or approximately 5-6 mg/kg or approximately 6-7 mg/kg or approximately 7-8 mg/kg or approximately 8-9 mg/kg or approximately 9-10 mg/kg; or approximately 10-21 mg/kg, such as approximately 10-11 mg/kg, or approximately 11-12 mg/kg, or approximately 12-13 mg/kg, or approximately 13-14 mg/kg, or approximately 14-15 mg/kg, or approximately 15-16 mg/kg, or approximately 16-17 mg/kg, or approximately 17-18 mg/kg, or approximately 18-19 mg/kg, or approximately 19-20 mg/kg or approximately 20-21 mg/kg.

Embodiment 131: The method according to any one of embodiments 109-130, wherein the dosage may be approximately 2 to 200 mg/kg, such as about 150-200 mg/kg, such as about 150-170 mg/kg, such as about 100-150 mg/kg, such as about 50-100 mg/kg, such as about 70-90 mg/kg, such as about 10-50 mg/kg, such as about 10-30 mg/kg.

Embodiment 132: The method according to any one of embodiments 109-131, wherein said monoclonal antibody may be administered parenterally.

Embodiment 133: The method according to embodiment 132, wherein said monoclonal antibody may be administered intravenously.

Embodiment 134: The method according to embodiment 133, wherein the dosage of said monoclonal antibody may be approximately 10-20 mg/kg.

Embodiment 135: The method according to any one of embodiments 133-134, wherein the monoclonal antibody may be administered every other week.

Embodiment 136: The method according to any one of embodiments 133-135, wherein the monoclonal antibody may be administered every third week.

Embodiment 137: The method according to any one of embodiments 133-136, wherein the monoclonal antibody may be administered every fourth week.

Embodiment 138: The method according to embodiment 133, wherein the dosage of said monoclonal antibody may be approximately 10-20 mg/kg and said monoclonal antibody may be administered every other week.

Embodiment 139: The method according to embodiment 133, wherein the dosage of said monoclonal antibody may be approximately 10-20 mg/kg and said monoclonal antibody may be administered every third week.

Embodiment 140: The method according to embodiment 133, wherein the dosage of said monoclonal antibody may be approximately 10-20 mg/kg and said monoclonal antibody may be administered every fourth week.

Embodiment 141: The method according to embodiment 132, wherein said monoclonal antibody may be administered intramuscularly.

Embodiment 142: The method according to embodiment 132, wherein said monoclonal antibody may be administered subcutaneously.

Embodiment 143: The method according to embodiment 132, wherein the dosage of said monoclonal antibody may be approximately 1 mg/kg Embodiment 144: The method according to any one of embodiments 141-143, wherein the monoclonal antibody may be administered daily.

Embodiment 145: The method according to any one of embodiments 141-144, wherein the monoclonal antibody may be administered every other day.

Embodiment 146: The method according to any one of embodiments 141-145, wherein the dosage of said monoclonal antibody may be approximately 1 mg/kg and wherein said monoclonal antibody may be administered daily.

Embodiment 147: The method according to embodiment any one of embodiments 141-146, wherein the dosage of said monoclonal antibody may be approximately 1 mg/kg and wherein said monoclonal antibody may be administered every other day.

Embodiment 148: The method according to any one of embodiments 109-147, wherein said antibody may be administered prophylactically.

Embodiment 149: The method according to any one of embodiments 109-148, wherein said antibody may be administered therapeutically (on demand).

Embodiment 150: The method according to any one of embodiments 109-149, wherein said administered antibody is capable of completely (100%) inhibiting soluble TFPI.

Embodiment 151: A polynucleotide encoding the monoclonal antibody according to any one of embodiments 1-94.

Embodiment 152: A polynucleotide according to embodiment 151, which comprises at least one sequence selected from the group consisting of SEQ ID NOs: 13, 16, 19 and 22.

Embodiment 153: A polynucleotide according to embodiment 152, which comprises SEQ ID NO: 19.

Embodiment 154: A polynucleotide according to embodiment 152, which comprises SEQ ID NO. 22.

Embodiment 155: A polynucleotide according to embodiment 152, which comprises SEQ ID NOs: 19 and 22.

Embodiment 156: A eukaryotic cell which comprises the polynucleotide according to any one of embodiments 151-155.

Embodiment 157: A eukaryotic cell which expresses the monoclonal antibody, or fragment thereof, according to any one of embodiments 1-94.

Embodiment 158: The eukaryotic cell according to embodiment 157, which is a mammalian cell.

Embodiment 159: The eukaryotic cell according to embodiment 157, which is a yeast cell.

Embodiment 160: The mammalian cell according to embodiment 158, which is selected from the group consisting of HEK293, CHO, BHK, NSO and human retina cells.

EXAMPLES

The present invention is further illustrated by the following examples which should not be construed as further limiting. The contents of all figures and all references, patents and published patent applications cited throughout this application are expressly incorporated herein by reference.

Example 1

Production and Characterisation of Monoclonal Antibodies Directed Against TFPI

Monoclonal antibodies were generated against tissue factor pathway inhibitor (TFPI). A monoclonal antibody having the desired binding specificity was identified, cloned and sequenced. This antibody was found to significantly reduce cuticle bleeding time in vivo and to lead to no significant drop in platelet number.

Methods and Results

All kits were used according to the manufacturers' instructions. Abbreviations: HC: heavy chain; LC: light chain; VH: variable domain—heavy chain; VL: variable domain—light chain; PCR: polymerase chain reaction.

Immunisation and Fusion

Mice were immunized with both full length TFPI and the short version TFPIB161B which contains only the first two Kunitz domains. RBF mice were used for immunizations and production of mouse monoclonal antibodies. Injections were made subcutaneously in the back of the mice. 20 µg protein was mixed with complete Freund's adjuvant for the first injection. In the subsequent immunizations, incomplete Freund's adjuvant was used with same concentration of the antigen. Ten days after the last immunization, eye-blood from mice was screened by ELISA for TFPI specific antibodies. Mice with positive serum titres were boosted with 10 µg of TFPI by intravenous injection, and sacrificed after three days. The spleens were removed aseptically and dispersed to a single cell suspension. Fusion of spleen cells and myeloma cells was done by the PEG-method or by electrofusion.

Binding Assay: ELISA

Immunoplates were coated with anti-mouse IgG. Culture supernatants from the hybridoma cells were added to the plates and, after washing, soluble biotinylated human TFPI or TFPIB161B was added to test for specific binding.

Neutralizing Assays: FXa Assay and TF/FVIIa/FXa Assay

FXa inhibition assay: a fixed concentration of TFPI giving rise to 90% inhibition of FXa was pre-incubated with culture supernatants from hybridoma cells containing anti TFPI monoclonal antibodies and added to FXa plus FXa-specific chromogenic substrate. This assay addresses TFPI binding to FXa (described in greater detail in example 6).

FVIIa/TF/FXa inhibition assay: 1) Incubation of culture supernatants from hybridoma cells containing anti TFPI monoclonal antibodies anti and fixed TFPI (90% inhibition of FVIIa/TF); 2) Incubation of TFPI+FVIIa+TF+FXa; 3) Addition of FX (FX>>FXa) followed by incubation with FXa chromogenic substrate (described in greater detail in example 7).

Dilute Prothrombin Time (dPT)

A dilute Prothrombin (PT) analysis: human plasma in combination with diluted human thromboplastin (TF source). Clot time in the plasma was measured upon addition of increasing protein A purified TFPI monoclonal antibody concentrations to look for dose dependent reduction of clotting time. FVIIa (25 nM) was the positive control and must shorten this clot time.

Binding Interaction Analysis

Binding interaction analysis was obtained by Surface Plasmon Resonance in a Biacore 3000. Capture of the relevant monoclonal antibody at a fixed concentration was obtained with immobilised mouse anti-IgG. Different concentrations of TFPI were tested. Determination of binding constants ($k_{on}$, $k_{off}$, $K_D$) was obtained assuming a 1:1 interaction of TFPI and the antibody of interest (described in greater detail in example 8).

Thrombelastography

This records the kinetic of clot formation and fibrinolysis in whole blood. Haemophilia A-like condition is induced by pre-incubating the blood with neutralizing anti-FVIII IgG.

Antibody Cloning and Sequencing

Murine heavy chain and light chain sequences for an anti-TFPI antibody were cloned from a hybridoma: TFPI-4F36A1B2 (abbreviated herein to 4F36). Total RNA, extracted from hybridoma cells using the RNeasy-Mini Kit from Qiagen, was used as templates for cDNA synthesis. cDNA was synthesized in a 5'-RACE reaction using the SMART™ RACE cDNA amplification kit from Clontech. Subsequent target amplification of HC and LC sequences was performed by PCR using Phusion Hot Star polymerase (Finnzymes) and the universal primer mix (UPM) included in the SMART™ RACE kit as a for-ward primer. A reverse primer with the following sequence was used for HC (VH domain) amplification: 5'-CCCTTGACCAGGCATCCCAG-3' (primer #129). A reverse primer with the following sequence was used for LC amplification: 5'-GCTCTAGAC-TAACACTCATTCCTGTTGAAGCTCTTG-3' (primer #69).

PCR products were separated by gel electrophoresis, extracted using the GFX PCR DNA and Gel Band Purification Kit from GE Healthcare Bio-Sciences and cloned for sequencing using a Zero Blunt TOPO PCR Cloning Kit and chemically competent TOP10 *E. coli* from Invitrogen. Colony PCR was performed on selected colonies using an AmpliTaq Gold Mas-ter Mix from Applied Biosystems and M13uni/M13rev primers. Colony PCR clean-up was performed using the ExoSAP-IT enzyme mix (usb). Sequencing was performed at MWG Biotech, Martinsried Germany using either M13uni(-21)/M13rev(-29) or T3/T7 sequenc-ing primers. Sequences were analyzed and annotated using the VectorNTl program.

From hybridoma TFPI-4F36A1B2 a single unique murine kappa type LC was identified and a single unique murine HC, subclass IgG1. LC sequence is given in SEQ ID NO: 6 and HC sequence is given in SEQ ID NO: 10. VH & VL Sequences are shown in FIG. 2, leader peptide sequences are not included.

Epitopes

TFPI1 includes three Kunitz domains (see FIG. 4). Surface accessible residues of the Kunitz domains of TFPI1 were identified from existing structures of TFPI1-2. In particular, residues with a relative accessibility larger than 40% are considered to be surface accessible. For TFPI1-2 this comprises (see FIG. 5): amino acids 94-95, 98, 100-110, 118-121, 123-124, 131, 134, 138-142 and 144-145.

Example 2

Cloning and Sequencing of Mouse TFPI4F36A1B2 mAb

This example describes cloning and sequencing of the murine heavy chain and light chain sequences of anti-TFPI antibody: TFPI4F36A1B2.

Total RNA was extracted from hybridoma cells using the RNeasy-Mini Kit from Qiagen and used as template for cDNA synthesis. cDNA was synthesized in a 5'-RACE reaction using the SMART™ RACE cDNA amplification kit from Clontech. Subsequent target amplification of HC and LC sequences was performed by PCR using Phusion Hot Start polymerase (Finnzymes) and the universal primer mix (UPM) included in the SMART™ RACE kit as forward primer. The reverse primer identified as SEQ ID NO: 11 was used for HC (VH domain) amplification and the reverse primer identified as SEQ ID NO: 12 was used for LC amplification. PCR products were separated by gel electrophoresis, extracted using the GFX PCR DNA & Gel Band Purification Kit from GE Healthcare Bio-Sciences and cloned for sequencing using a Zero Blunt TOPO PCR Cloning Kit and chemically competent TOP10 E. coli (Invitrogen). Colony PCR was performed on selected colonies using an AmpliTaq Gold Master Mix from Applied Biosystems and M13uni/ M13rev primers. Colony PCR clean-up was performed using the ExoSAP-IT enzyme mix (USB). Sequencing was performed at MWG Biotech, Martinsried Germany using either M13uni(-21)/M13rev(-29) or T3/T7 sequencing primers. Sequences were analyzed and annotated using the VectorNT1 program. All kits and reagents were used according to the manufacturer's instructions. A single unique murine kappa type LC and a single unique murine HC, subclass IgG1 was identified. The nucleic acid and amino acid sequences for the variable light chain are shown in SEQ ID NOs: 3 and 5, respectively. The nucleic acid and amino acid sequences for the variable heavy chain are shown in SEQ ID NOs: 7 and 9, respectively. Leader peptide sequences are not included in these sequences.

BLAST Searches

The translated anti-TFPI4F36A1B2 VL and VH amino acid sequences were used as query sequences. BLAST searches were performed against sequences in the Uniprot database using the BLASTp translations program. The output for the anti-TFPI4F36A1B2 VH produces alignments of which >20 of the 50 highest identity scores were murine Ig heavy chain sequences. The highest identity scores were 81% (99/121) against a mouse Ig heavy chain. The output for the anti-TFPI4F36A1B2 VL produces alignments of which >30 of the 50 highest identity scores were murine Ig kappa light chain sequences. The highest identity score was 92% (105/113) against a mouse Ig kappa light chain. In conclusion, the VH and VL sequences for anti-TFPI4F36A1B2 represent new unique sequences.

Generation of Mouse anti-TFPI4F36A1B2 Expression Vectors

A series of CMV promotor-based based expression vectors (pTT vectors) were generated for transient expression of the mouse TFPI4F36 antibody in the HEK293-6E EBNA-based expression system developed by Yves Durocher (Durocher et al. Nucleic Acid Research, 2002). In addition to the CMV promotor, the vectors contain a pMB1 origin, an EBV origin and the Amp resistance gene.

The region corresponding to the full length anti-TFPI4F36A1B2 LC (including the original signal peptide sequence) was PCR amplified from the original TOPO sequencing clones using primers specific for the N and C-terminal sequences. The sense primer contained a terminal HindIII restriction site sequences for cloning purposes and a Kozak sequence (5'-GCCGCCACC-3') immediately upstream of the ATG start codon. The anti-sense primer contained a stop codon followed by an XbaI restriction site sequence, immediately downstream of the coding sequence. The generated PCR fragment was restriction digested, cloned into the multiple cloning site (MCS) of a linearized pTT-based vector and transformed into E. coli for selection. The sequence of the final construct was verified by DNA sequencing.

The region corresponding to the VH domain (including the original signal peptide sequence) was PCR amplified from the original TOPO sequencing clones using primers specific for the N-terminal sequence and VH/CH transition sequence. The sense primer contained a terminal NotI restriction site sequences for cloning purposes and a Kozak sequence (5'-GCCGCCACC-3') immediately upstream of the ATG start codon. The anti-sense primer contained an in-frame NheI restriction site downstream of the VH/CH transition. The generated VH domain PCR fragment was restriction digested, cloned into a linearized vector containing the CH domain sequence for a murine IgG1 and transformed into E. coli for selection. The sequence of the final construct was verified by DNA sequencing.

The cloned and recombinantly expressed anti-TFPI4F36A1B2 antibody had the same profile and affinity in all assay used, as the original hybridoma derived antibody. Procedures used for transient expression in HEK293-6E cells are described in example 3.

Example 3

Design and Construction of a Humanized TFPI4F36 mAb

The mouse anti-TFPI4F36A1B2 CDR sequences were annotated according to the Kabat definition and found to be as follows:

```
                    (amino acids 31-35 of SEQ ID NO: 8)
CDR-H1: NYAMS.

(amino acids 50-66 of SEQ ID NO: 8)
CDR-H2: TISRSGSYSYFPDSVQG.

(amino acids 99-110 of SEQ ID NO: 8)
CDR-H3: LGGYDEGDAMDS.

(amino acids 24-39 of SEQ ID NO: 4)
CDR-L1: KSSQSLLESDGKTYLN.

(amino acids 55-61 of SEQ ID NO: 4)
CDR-L2: LVSILDS.

(amino acids 94-102 of SEQ ID NO: 4)
CDR-L3: LQATHFPQT.
```

A 3D model of anti-TFPI4F36A1B2 was built in Modeller (www.salilab.org/modeller/) based on the structural templates 2GJJ (mAB against Her2erbb2) and 1X9Q (hAB against flourescein).

A BLASTp search in a human germline V database with the anti-TFPI4F36A1B2 VL and VH returned the following four potential germline sequences:

Heavy chain: VH3_21 or VH7183.9 (E-values<1e-45)
Light chain: VKII_A18 or VKII_A1 (E-values<3e-45)

After manual inspection of hits and alignments, the VH3_21 and VKII_A18 germline sequences were selected as HC and LC humanization frameworks, respectively. The corresponding germline J-segments were selected based on sequence alignment as JH6 and JK4. The alignment between anti-TFPI4F36A1B2 and the selected germline sequences are shown in combination with the first CDR grafted version of the humanized TFPI4F36. The sequence identity between anti-TFPI4F36A1B2 and the human scaffolds (HC: VH3_21/JH6 and LC: VKII_A18/JK4) is very high as illustrated by asterisks below the sequence. Each asterisk marks a position of sequence identity. The initial humanized VH construct was designed according to a minimal CDR grafting strategy, in which CDR-H2 is grafted in a shorter version (residue 50-58) than the Kabat definition (residue 50-66). The remaining 5 CDRs were grafted according to the Kabat definition. The CDRs (Kabat definition) are listed as grafted below; the residues shown in bold for CDR-H2 are human germline residues.

```
                    (amino acids 31-35 of SEQ ID NO: 18)
CDR-H1: NYAMS.

(amino acids 50-66 of SEQ ID NO: 28)
CDR-H2: TISRSGSYSYYADSVKG.
```

```
               (amino acids 99-110 of SEQ ID NO: 18)
    CDR-H3:  LGGYDEGDAMDS.

(amino acids 24-39 of SEQ ID NO: 15)
    CDR-L1:  KSSQSLLESDGKTYLN.

(amino acids 55-61 of SEQ ID NO: 15)
    CDR-L2:  LVSILDS.

(amino acids 94-102 of SEQ ID NO: 15)
    CDR-L3:  LQATHFPQT.
```

The composition of CDR-H2 in the final humanized variant HzTFPI4F36 is listed below and matched the CDR-H2 listed for the mouse antibody anti-TFPI4F36A1B2.

```
               (amino acids 50-66 of SEQ ID NO: 18)
    CDR-H2:  TISRSGSYSYFPDSVQG.
```

FIG. 1 shows the sequences of VH (A) and VL (B) domains of mouse anti-TFPI4F36A1B2 (SEQ ID NOs: 8 and 4, respectively) aligned with human germline sequences (SEQ ID NOs: 32 and 31, respectively) and the CDR grafted humanized TFPI4F36 sequences (SEQ ID NOs: 28 and 26, respectively). The Kabat numbering scheme is used, as shown above the sequences in the figure, and CDRs according to the Kabat definition are shown in bold. Differences in the framework regions between the mouse anti-TFPI4F36A1B2 and the germline sequences are highlighted in grey in the anti-TFPI4F36A1B2 sequence. Asterisks indicate positions of sequence identity between the mouse TFPI4F36 and human germline sequences. Potential back mutations are highlighted in gray in the HzTFPI4F36-CDRgrafted sequence (listed as hz4F36CDRgraft).

Potential back mutations for the HzTFPI4F36-CDRgrafted constructs were identified based on the positional differences found in the frameworks regions of mouse TFPI4F36 and the germline sequence. A 3D FIG. 1 shows the sequences model of the TFPI4F36 Fab fragment was also used to identify and prioritize potential back mutations. The lists of generated back mutations in the humanized TFPI4F36 LC and HC are shown in tables 2 and 3, respectively.

Generation of Expression Vectors for Humanized TFPI4F36

DNA sequences for humanized TFPI4F36 VH and VL regions were synthesized (GENEART AG) according to the humanization design of the antibody described above. The sequences were obtained with the basic minimal CDR grafting and no additional back mutations. The respective LC and HC germline leader peptide sequences were include in the constructs as well as a Kozak sequence (5'-GCCGCCACC-3') immediately upstream of the ATG start codon.

pTT-based expression vectors were generated for transient expression of the humanized TFPI4F36 antibody as a human kappa/IgG4(S241P) isotype. The proline mutation at position 241 (numbering according to Kabat, corresponding to residue 228 per the EU numbering system (Edelman G. M. et AL., Proc. Natl. Acad. USA 63, 78-85 (1969)) was introduced in the IgG4 hinge region to eliminated formation of monomeric antibody fragments, i.e. "half-antibodies" comprising of one LC and one HC.

The VH fragment was excised from the GENEART cloning vector and cloned into a linearized pTT-based vector containing the sequence for a human IgG4(S241P) CH domain subsequently transformed into E. coli for selection. The sequence of the final construct was verified by DNA sequencing. The VL fragment was excised from the GENEART cloning vector and cloned into a linearized pTT-based vector containing the sequence for a human kappa CL domain and subsequently transformed into E. coli for selection. The sequence of the final construct was verified by DNA sequencing.

Nucleic acid and amino acid sequences for the VL, VH, LC and HC of the CDR-grafted HzTFPI4F36 monoclonal antibody (signal peptide sequence omitted) are provided in the sequence listing (SEQ ID NOs: 26-30).

Generation of Expression Vectors for Mouse/Human Chimeric TFPI4F36

To enable the best possible evaluation of the humanized TFPI4F36 variants, a mouse/human chimera version of the anti-TFPI4F36 antibody (ChimTFPI4F36) was constructed in order to eliminate any differences related to constant region origin and isotype. pTT-based expression vectors were generated for transient expression of chimeric anti-TFPI4F36 antibody with murine variable domains on the human kappa/IgG4(S241P) isotype scaffolds.

The region corresponding to the VH domain was PCR amplified from a anti-TFPI4F36A1B2 HC expression plasmid using a generic pTT specific primer and a primer specific for the VH domain C-terminus. The sense primer is specific for at sequence stretch upstream of the HindIII restriction site and the ATG start codon. The anti-sense primer contained an in-frame NheI restriction site in the VH/CH transition sequence. The generated PCR fragment was restriction digested, cloned into a linearized pTT-based vector containing the sequence for a human IgG4(S241P) CH domain and subsequently transformed into E. coli for selection. The sequence of the final construct was verified by DNA sequencing.

The region corresponding to the VL domain was PCR amplified from a TFPI4F36A1B2 LC expression plasmid using a generic pTT specific primer and a primer specific for the VL domain C-terminus. The sense primer is specific for at sequence stretch upstream of the HindIII restriction site and the ATG start codon. The anti-sense primer contained an in-frame BsiWI restriction site in the VL/CL transition sequence. The generated PCR fragment was restriction digested, cloned into a linearized pTT-based vector containing the sequence for a human kappa CL domain and subsequently transformed into E. coli for selection. The sequence of the final construct was verified by DNA sequencing.

Recombinant Expression of mAb Variants

The murine anti-TFPI4F36A1B2, chimeric anti-TFPI4F36 and humanized TFPI4F36 antibody variants were expressed transiently in HEK293-6E cells following a generic antibody expression protocol. The following procedure describes the generic transfection protocol used for suspension adapted HEK293-6E cells.

Cell Maintenance

HEK293-6E cells were grown in suspension in FreeStyle™ 293 expression medium (Gibco) supplemented with 25 µg/ml Geneticin (Gibco), 0.1% v/v of the surfactant Pluronic F-68 (Gibco) & 1% v/v Penicillin-Streptomycin (Gibco). Cells were cultured in Erlenmeyer shaker flasks in shaker incubators at 37° C., 8% $CO_2$ and 125 rpm and maintained at cell densities between $0.1$-$1.5 \times 10^6$ cells/ml.

DNA Transfection

The cell density of cultures used for transfection was $0.9$-$2.0 \times 10^6$ cells/ml.

A mix of 0.5 µg LC vector DNA+0.5 µg HC vector DNA was used per ml cell culture.

The DNA was diluted in Opti-MEM media (Gibco) 30 µl media/µg DNA, mixed and incubated at room temperature (23-25° C.) for 5 min.

293Fectin™ (Invitrogen) was used as transfection reagent at a concentration of 1 µl per pg DNA.

The 293Fectin™ was diluted 30× in Opti-MEM media (Gibco), mixed and incubated at room temperature (23-25° C.) for 5 min.

The DNA and 293Fectin solutions were mixed and left to incubate at room temperature (23-25° C.) for 25 min.

The DNA-293Fectin mix was then added directly to the cell culture.

The transfected cell culture was transferred to a shaker incubator at 37° C., 8% $CO_2$ and 125 rpm.

3-6 days post transfection, cell culture supernatants were harvested by centrifugation, followed by filtration through a 0.22 μm PES filter (Corning).

Quantitative analysis of antibody production was performed by Biolayer Interferometry directly on clarified cell culture supernatants using the FortéBio Octet system and protein A biosensors or quantitative protein A HPLC.

Activity Analyses of the CDR Grafted Variant of Humanized anti-TFPI4F36

Humanization by minimal CDR grafting resulted in a dramatic loss of affinity caused by effect on both on- and off-rate. The TFPI binding affinity of the initially grafted version of the humanized TFPI4F36 antibody (HzTFPI4F36-CDRgrafted, in table 1 listed as Humanized TFPI4F36) was at least 100-fold lower than the ~30 pM affinity of the original mouse TFPI4F36 antibody (see table 1). Retention of affinity in the chimeric antibody confirmed that the human kappa/IgG4 (S241P) FC had no effect on antibody affinity. The affinity analyses were done using SRP as described below.

TABLE 1

| mAb | ka (1/Ms) | kd (1/M) | KD (M) |
|---|---|---|---|
| Murine TFPI4F36 | 4.70E+06 | 1.33E−04 | 2.82E−11 |
| Chimeric TFPI4F36 | 8.88E+06 | 1.44E−04 | 1.62E−11 |
| Humanized TFPI4F36 | 1.07E+06 | 2.21E−03 | 2.06E−09 |

Surface Plasmon Resonance (Biacore) Analysis of hzTFPI4F36-TFPI Interaction

The kinetic parameters for the interaction of recombinant human TFPI to the original murine anti-TFPI4F36A1B2, chimeric anti-TFPI4F36, and various variants of the humanized TFPI4F36 antibody were determined by SPR analysis in Biacore, using two different approaches. Initial kinetics ranking studies were based on a capture procedure of purified mAbs as described in example 1. These were followed by a direct binding kinetic procedure on selected mAb constructs, with the monoclonal antibody covalently coupled via free amine groups to the carboxymethylated dextrane membrane (CM5) on the sensor chip surface. Recombinant human TFPI was injected in various concentrations, followed by a dissociation period with constant buffer flow over the sensor chip surface as described in example 8.

Site-Directed Mutagenesis to Introduce Back Mutations in Humanized mAb

Based on the low affinity of the CDR grafted version of humanized anti-TFPI4F36, a series of 27 human-to-mouse reverse mutations (referred to as back mutations) was generated in the light chain (LC) and heavy chain (HC) of HzTFPI4F36-CDRgrafted. These mutants were expressed, purified and analyzed by Biacore, either as separate mutants or as LC/HC combination mutants. The lists of generated mutations are shown in tables 2 and 3, respectively.

Site-directed mutagenesis was performed to introduce human-to-mouse reverse mutations (henceforth referred to as back mutations) at the specific residues in the HzTFPI4F36-CDRgrafted LC/HC constructs as highlighted in the humanization design. Mutations were introduced by two different methods:

1) QuickChange® Site-Directed or Multi Site-Directed Mutagenesis kits from Stratagene were used to introduce point mutations and combination mutations. The kits were used according to the manufacturer's protocol.
2) Standard 2-step overlapping PCR methods were also used to introduce point mutations and to generate combination mutations.

The LC and HC expression plasmids for HzTFPI4F36-CDRgrafted were used as templates for the first rounds of mutagenesis. In subsequent rounds, mutations were also introduces using previously mutated plasmids as template. The sequences of all final constructs were verified by DNA sequencing.

TABLE 2

Mutated variants of the HzTFPI4F36-CDRgrafted light chain

| LC mutants | Mutations | $K_D$ (M) |
|---|---|---|
| HzTFPI4F36 LC-S63T | S63T | 7.8E−9 |
| HzTFPI4F36 LC-P15I | P15I | 17.0E−9 |
| HzTFPI4F36 LC-FR2 | Y36L, K39R, Q42E, Q45K | 6.3E−10 |
| HzTFPI4F36 LC-P15I, FR2 | P15I, Y36L, K39R, Q42E, Q45K | 6.4E−10 |
| HzTFPI4F36 LC-Y36L | Y36L | >3E−11 |
| HzTFPI4F36 LC-K39R, Q42E, Q45K | K39R, Q42E, Q45K | >3E−11 |

TABLE 3

Mutated variants of the HzTFPI4F36-CDRgrafted heavy chain

| HC mutants | Mutations | $K_D$ (M) |
|---|---|---|
| HzTFPI4F36 HC-Q3E | Q3E | 5.8E−9 |
| HzTFPI4F36 HC-G44R | G44R | 2.3E−9 |
| HzTFPI4F36 HC-S49A | S49A | 3.0E−9 |
| HzTFPI4F36 HC-Y59F | Y59F | 5.5E−9 |
| HzTFPI4F36 HC-A60P | A60P | 2.2E−9 |
| HzTFPI4F36 HC-K64Q | K64Q | 2.5E−9 |
| HzTFPI4F36 HC-S77T | S77T | 1.5E−9 |
| HzTFPI4F36 HC-A93T | A93T | 2.7E−9 |
| HzTFPI4F36 HC-Y59F, A60P | Y59F, A60P | 2.3E−9 |
| HzTFPI4F36 HC-KABAT CDR2 | Y59F, A60P, K64Q | 9.0E−10 |
| HzTFPI4F36 HC-FR2, S49A | A40T, G42E, G44R, S49A | 1.3E−9 |
| HzTFPI4F36 HC-FR3 | N82aS, A84S, V89M | 5.3E−9 |
| HzTFPI4F36 HC-FR3, S77T | S77T, N82aS, A84S, V89M | 7.7E−9 |
| HzTFPI4F36 HC-FR3, A93T | N82aS, A84S, V89M, A93T | 4.1E−9 |
| HzTFPI4F36 HC-FR2 | A40T, G42E, G44R | 8.8E−10 |
| HzTFPI4F36 HC-FR2, S49A, CDR2 | A40T, G42E, G44R, S49A, Y59F, A60P, K64Q | 2.6E−11 |
| HzTFPI4F36 HC-G42E, G44R, CDR2 | G42E, G44R, Y59F, A60P, K64Q | 3.9E−11 |
| HzTFPI4F36 HC-FR2, CDR2 | A40T, G42E, G44R, Y59F, A60P, K64Q | >3E−11 |
| HzTFPI4F36 HC-G42E, G44R, S49A CDR2 | G42E, G44R, S49A, Y59F, A60P, K64Q | >3E−11 |
| HzTFPI4F36 HC-G42E, G44R, A60P, K64Q | G42E, G44R, A60P, K64Q | 9.3E−11 |
| HzTFPI4F36 HC-G44R, A60P, K64Q | G44R, A60P, K64Q | 3.0E−11 |

The mutations in both LC and HC as listed in tables 2 and 3 are consistently numbered according to the Kabat numbering scheme as shown in FIG. 1.

The LC mutants listed in table 2 were expressed as LC mutants only together with wild type HC HzTFPI4F36 CDRgrafted. The HC mutants listed in table 3 were expressed as HC mutants only together with wild type LC HzTFPI4F36 CDRgrafted. LC-HC combination mutants were also expressed by combining different LC and HC mutants. Mutants are consistently named after the mutated chain, i.e. the final humanized mAb variant is expressed with wild type HzTFPI4F36-CDRgrafted LC and the mutated HzTFPI4F36 FR2, S49A, CDR2 HC. Transient HEK293-6E expression was performed as described above.

The initial set of 9 point mutants (HzTFPI4F36 LC-S63T & HzTFPI4F36 HC-Q3E; G44R; S49A; Y59F; A60P; K64Q; S77T; A93T) were based on a primary set of back mutations highlighted in the humanization design. None of the point mutants rescued the affinity of the antibody, however mutations in the second human heavy chain framework region (FR2, between CDR H1 and CDR H2) and in the C-terminal region of CDR H2 (omitted in the minimal CDR grafting scheme) were highlighted as being important for TFPI binding. Affinity measurements by Biacore analyses were performed as described above.

The subsequent rounds of mutagenesis included a number of patch mutants in which all residues in individual regions were mutated collectively. The mutant HzTFPI4F36 HC-Kabat CDR2, has 3 mutations Y59F, A60P, K64Q in the C-terminal region of CDR H2, which corresponds to grafting CDR H2 according to the Kabat definition and not according to the minimal CDR grafting scheme used for the initial HzTFPI4F36-CDRgrafted variant. This patched mutant along with patch mutants in LC FR2 and HC FR2 improved the affinity of the humanized TFPI4F36 antibody significantly, but neither of the three patch mutants individually restored the high TFPI4F36 affinity.

The HC mutant with combined mutations in HC FR2, and CDR2 (A40T, G42E, G44R, S49A, Y59F, A60P, K64Q) did restore affinity completely. This mutant introduced 7 additional murine residues into the antibody sequence. Combination of LC FR2 mutants (both FR2 mutations and Y36L) and HC FR2 and/or CDR2 mutants also resulted in high affinity mutants. However the combination of these LC/HC mutants consistently resulted in lower expression yields compared to the HC mutants alone. These results indicated that inclusion of the LC mutants had a negative impact on the stability of these antibody variants, hence suggesting that a delicate interaction pattern between the humanized TFPI4F36 LC and HC exist.

In the last series of mutants, the 7 mutations in HC FR2, and CDR2 (A40T, G42E, G44R, S49A, Y59F, A60P, K64Q) were dissected in order to eliminate potentially non-contributing back mutations. A series of 5 mutants were generated to address this point.

In 3 mutants, back mutations were excluded in FR2:
HzTFPI4F36 HC-G42E, G44R, CDR2
HzTFPI4F36 HC-FR2, CDR2
HzTFPI4F36 HC-G42E, G44R, S49A CDR2

In 2 mutants additional mutations in CDR2 were also eliminated:
HzTFPI4F36 HC-G44R, A60P, K64Q
HzTFPI4F36 HC-G42E, G44R, A60P, K64Q None of the mutants however, were on par with the combined HC FR2 CDR2 mutant. Either affinity or expression levels (or both) were impacted by any reduction in the HC FR2 CDR2 mutant subset. The two mutants HzTFPI4F36 HC G42E, G44R, Y59F, A60P, K64Q with 5 remaining back mutations and HzTFPI4F36 HC G42E, G44R, A60P, K64Q with 4 residual back mutations were picked for thorough comparison with HzTFPI4F36 HC-FR2, S49A, CDR2.

HzTFPI4F36 HC-G42E, G44R, A60P, K64Q and HzTFPI4F36 HC-FR2, S49A, CDR2 expressed at comparable levels, while HzTFPI4F36 HC-G42E, G44R, CDR2 had a slightly lower expression level. Accelerated biophysical stability studies did not show any differences in stability in the three variants.

The affinities measured by Biacore are listed below.

In vivo efficacy measured in the dPT assay (as described below) were comparable for all three variants.

TABLE 4

Kinetic parameters for the interaction between TFPI and humanized TFPI4F36 variants.

| Mutant | $K_D$ (pM) | Expression yield (mg/L) | No of back mutations |
|---|---|---|---|
| HzTFPI4F36 A40T, G42E, G44R, S49A, Y59F, A60P, K64Q | 26 | 54 | 7 |
| HzTFPI4F36 G42E, G44R, Y59F, A60P, K64Q | 39 | 24 | 5 |
| HzTFPI4F36 G42E, G44R, A60P, K64Q | 93 | 53 | 4 |

Based on the data described above, the original HC FR2, and CDR2 mutant with 7 HC back mutations (A40T, G42E, G44R, S49A, Y59F, A60P, K64Q) tested superior to other variants; this variant is herein referred to as HzTFPI4F36 or as mAbTFPI2021.

It is likely that the CDR2 mutations Y59F, A60P, K64Q affect antibody affinity by directly interacting with antigen. Mutations A40T, G42E, G44R reside in a FR2 turn connecting CDRH1 and CDR H2, remote from the antigen binding face and could be poised for stabilizing LC-HC interactions. The mutation S49A is buried in the middle of a highly hydrophobic cluster of side chains which could explain why alanine is preferred over serine at this position Interestingly therefore, the high affinity of HzTFPI4F36 is obtained as a combination of mutations which improve the direct antigen interaction and mutations remote from the antigen binding region which stabilize the antibody.

In conclusion, HzTFPI4F36 has an affinity ($K_D$) of ~25 pM and contains 35 amino acid residues derived from the mouse antibody sequence, corresponding to 5.2% of the total number of residues in the antibody.

The amino acid sequences for the variable light (VL) region, variable heavy (VH) region, light chain and heavy chain of a selected humanized construct, HzTFPI4F36 (mAbTFPI 2021), are shown in SEQ ID NOs: 15, 18, 21 and 24, respectively.

In-vitro Efficacy Assays

The anti-TFPI4F36 antibody is capable of neutralizing TFPI-mediated inhibition of coagulation factor Xa (FXa) and the complex of tissue factor (TF) and factor VIIa (FVIIa). The activities of murine and humanized TFPI4F36 antibody variants were measured in a dilute prothrombin time (dPT) test. The dPT assay was used for measuring the procoagulant activity of anti-TFPI antibodies. Increasing plasma concentrations of anti-TFPI antibody shortens the dPT clotting time.

Example 4

Purification, Crystallization and Structure of the Fab-Fragment of MuTFPI4F36 (Fab) and the Second Kunitz Domain (K2) of Human Tissue Factor Pathway Inhibitor (TFPI)

A fragment of TFPI including its second Kunitz domain (K2) and a C-terminal $His_6$-tag (SEQ ID NO: 2) was co-crystallized with the MuTFPI4F36 Fab fragment (Fab). The structure of the complex was solved by X-ray crystallography. The K2 binding epitope was found to be composed of residues E10, E11, P13, R17, Y19, T21, Y23, Q28, Q31, E33, R34, F35, K36 and L50. The paratope in the Fab was found to comprise residues E31, S32, D33, Y37, A96, T97, H98 and F99 of the MuTFPI4F36 light chain (SEQ ID NO: 4) and residues N31, R53, S54, S56, Y57, Y59, F60, P61, D62, Q65, Y102, D103 and D106 of the MuTFPI4F36 heavy chain (SEQ ID NO: 8).

Materials and Methods
Analytical Size Exclusion Chromatography.

Analytical size exclusion chromatography (SEC) was performed using a Biosep S-3000 (300×7.80 mm) column (Phenomenex) eluted with PBS-buffer (10 mM phosphate, 150 mM NaCl, 3 mM KCl, pH 7.5) at a flow rate of 0.8 ml/min.

Preparation and Purification of the Fab/K2 Complex.

The Fab/K2 complex was prepared by mixing Fab (0.27 mg/ml in PBS buffer, pH 7.4) and K2 (0.29 mg/ml in PBS, pH 7.4) in a molar ratio of 1:1.5 (5.4 mg Fab and 1.4 mg K2). The complex was concentrated on a centrifugal filter device (Amicon, 10 kD mw cut-off) to a concentration of ~6.7 mg/ml. To remove excess K2, the concentrated sample was applied to a Superdex 75 (CV300) gel filtration column eluted with PBS-buffer, pH 7.4 at a flow rate of 1 ml/min. Fractions containing the Fab/K2 complex were pooled and concentrated to a protein concentration of 9.2 mg/ml. This solution was used for crystallization.

Crystallization of the Fab/K2 Complex.

The Fab/K2 complex was crystallized as rods by the hanging drop method using a precipitant solution containing 0.2 M tribasic potassium citrate (pH 8.0) and 20% w/v PEG 3,350.

Crystal Structure Determination.

The structure of the Fab/K2 complex was solved by the molecular replacement method using PDB structures 1F8T and 1TFX as templates for the Fab and K2 molecules, respectively.

Results

Figure 6:
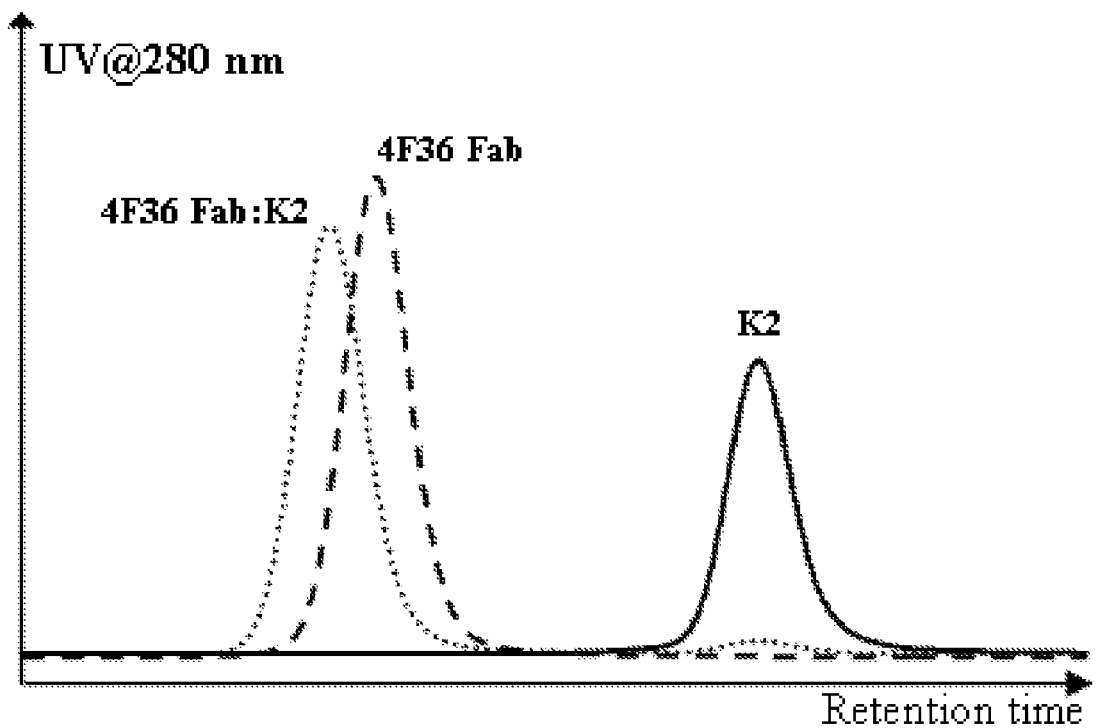
FIG. 6 shows an SEC HPLC analysis of a complex between the TFPI Kunitz domain 2 (K2) and the MuTFPI4F36 Fab fragment (Fab). SEC-HPLC chromatograms detected at UV 280 nm of free K2 (solid line, $r_t$ 13.1 min, peak shown at 13.134), free Fab (dashed line, $r_t$ 11.7 min, peak shown at 11.676) and complex (dotted line, $r_t$ 11.5 min, peak shown at 11.496). The sample of the complex contained ~20% excess K2.

The complex between Fab and K2 was prepared by adding excess of K2 to a solution of Fab. FIG. 6 shows the complex formation monitored by analytical size exclusion chromatography (SEC). This method separates molecules according to their molecular size with the larger species eluting earlier than smaller. The peaks corresponding to K2 and Fab were well separated due to the large difference in molecular weight (mw ~8 kDa and 48 kDa, respectively). Addition of K2 to the Fab solution resulted in the expected minor shift in the peak position towards shorter retention times. The complex was easily separated and obtained in pure form by separating excess K2 using preparative SEC.

Figure 7:
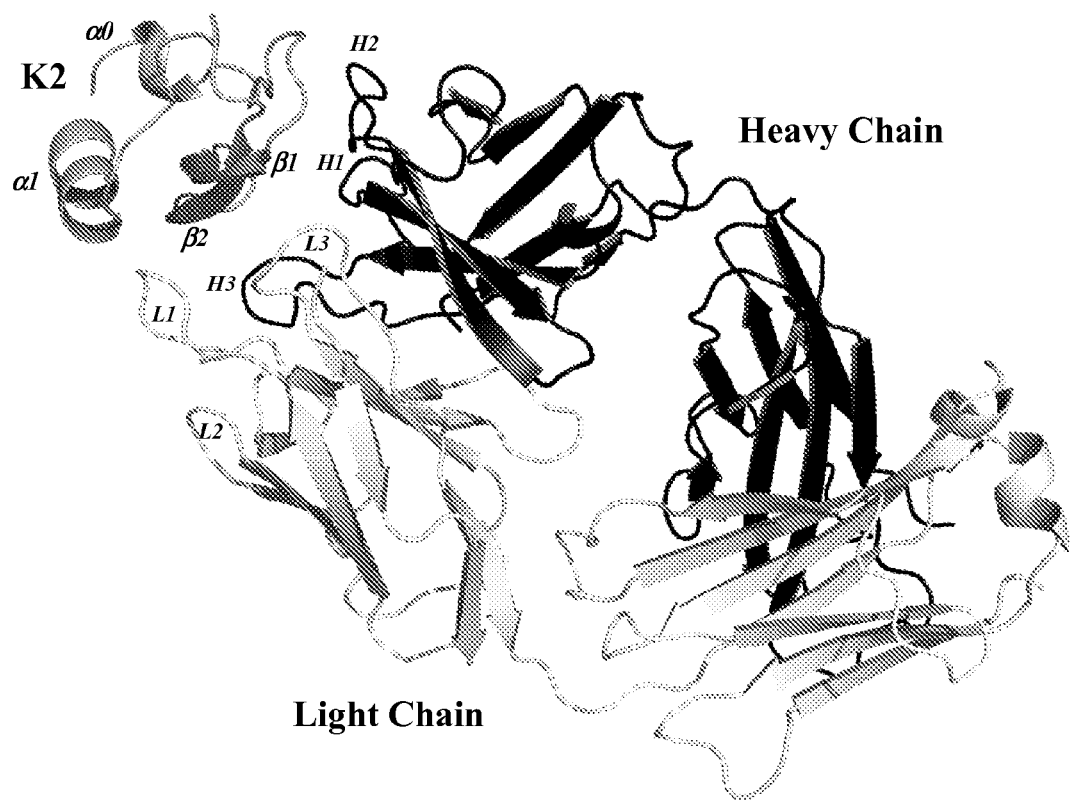
FIG. 7 shows the overall structure of the MuTFPI4F36 Fab:K2 complex. Light chains are shown in pale grey and heavy chains are shown in dark grey. The CDR loops as defined according to the Kabat scheme are labeled as L1 to L3 and H1 to H3.

Conditions for crystallization of the Fab/K2 complex were screened using several commercial crystallization screens. The hanging drop method afforded rod-shaped crystals suitable for single crystal X-ray analysis and the structure was solved by the molecular replacement method using structures deposited in the PDB as templates. FIG. 7 shows the overall structure of the Fab/K2 complex. Displayed are the light and heavy chains, constituting the Fab molecule, and exhibiting the expected immunoglobulin β-sandwich fold characteristic for antibody molecules. Also shown are the CDR loops making contact with the antigen and defining the specificity and affinity of the antibody.

Figure 8:
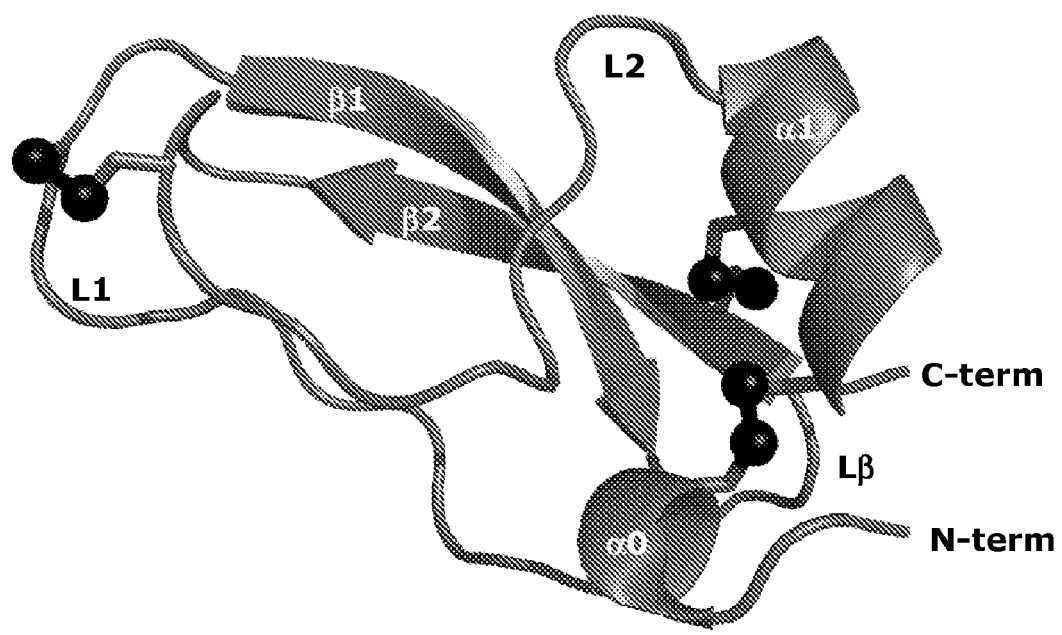
FIG. 8 shows the structure of the K2 domain of TFPI when in a complex with MuTFPI4F36 Fab (Fab molecule not shown). The N- and C-termini and secondary structural elements are labeled.

The antigen, K2, exhibits the characteristic single anti-parallel β-sheet (β1 (I20-N26) and β2 (Q31-Y37)) and the N-terminal α-helix (α1, L50-156) that defines the Kunitz-fold (FIG. 8). Present is also the optional $3_{10}$-helix near the N-terminus (α0, D5-F8) followed by loop 1 (L1, L9-Y19) leading to β1, which is connected to β2 via a short loop (Lβ, N27-K30). In the C-terminal segment, loop 2 (L2, G38-T49) connects β2 with α1. Finally, the characteristic three disulfide bonds (C7-057, C16-C40 and C33-053) connect α0 with α1, L1 with L2 and β2 with α1, respectively.

Figure 9:
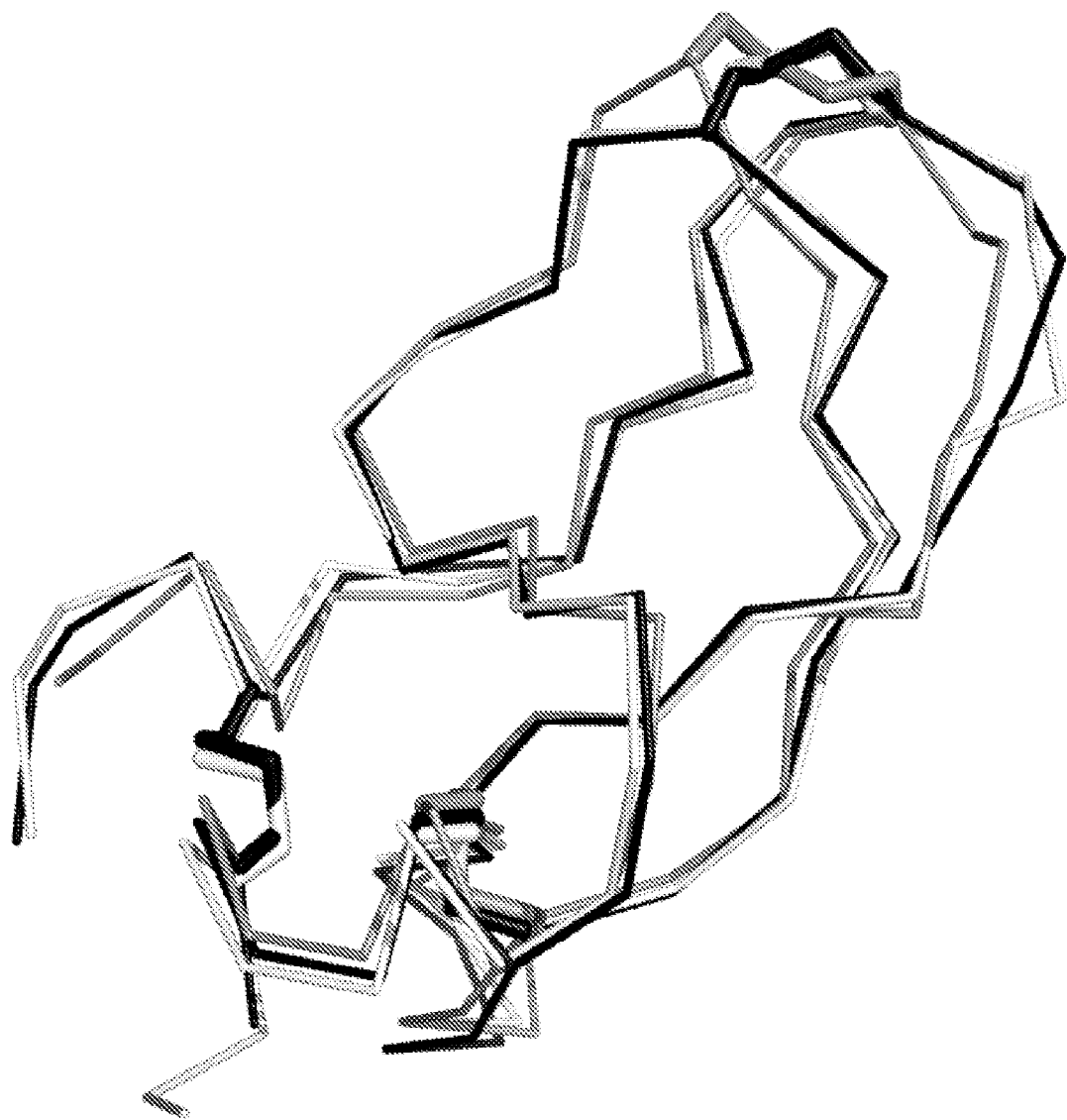
FIG. 9 shows a back-bone superposition of K2 structures. Shows differences in structure between K2 solution, K2 is in complex with MuTFPI4F36 Fab and K2 in complex with porcine trypsin.

Two structures of K2 have been deposited in the Worldwide Protein DataBank (PDB). One structure, 1ADZ, is determined by NMR spectroscopy and represents the free solution structure, whereas the other, 1TFX, is determined by X-ray crystallography and represents K2 complexed with porcine trypsin. FIG. 9 shows the structural superposition of K2 represented by 1ADZ, 1TFX and the K2 molecule in complex with Fab. The back-bone traces appear very similar among all three structures, suggesting that the Kunitz-fold with its three stabilizing disulfide bonds is rather rigid.

Description of the MuTFPI4F36 K2 Binding Epitope

Figure 10:
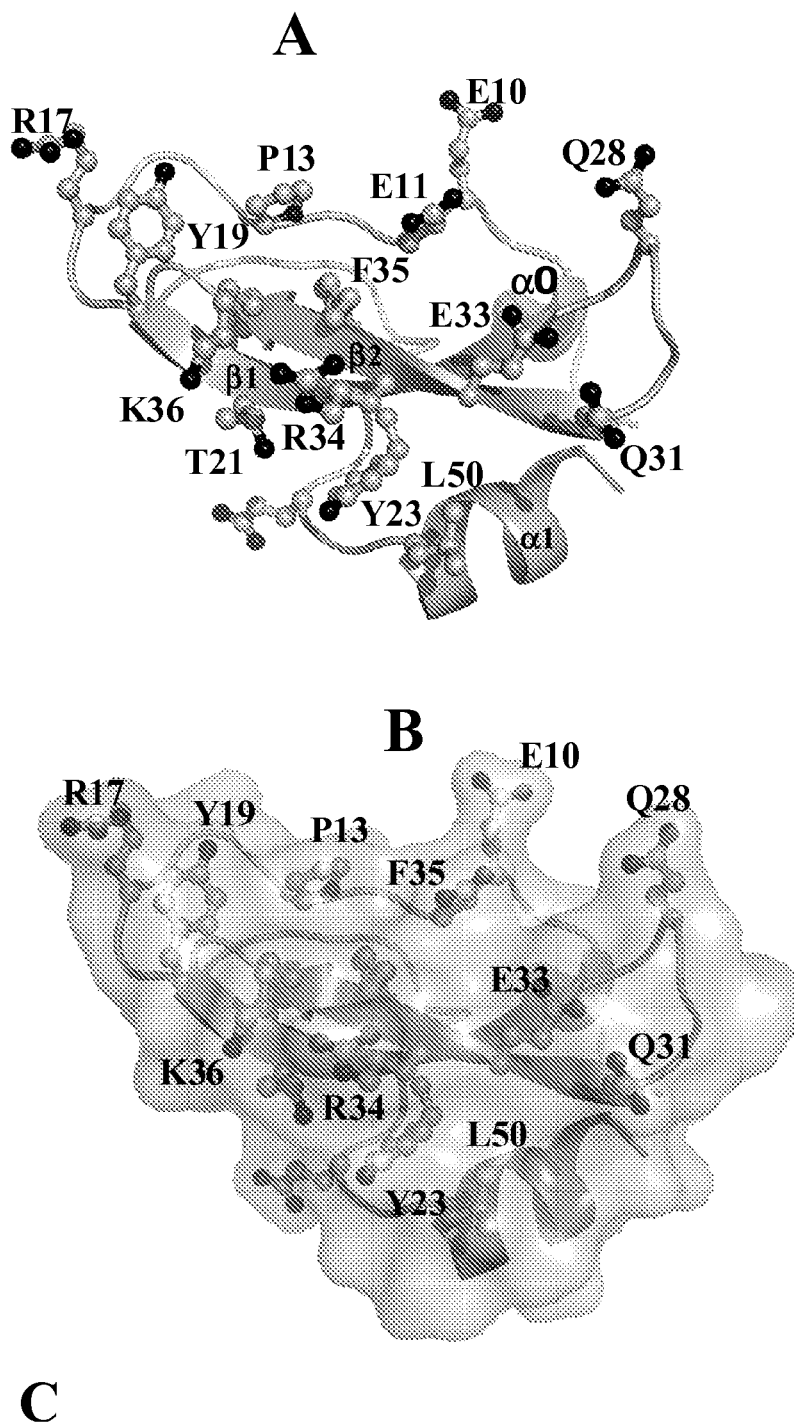
FIG. 10 shows the MuTFPI4F36 binding epitope on K2. (A) Cartoon representation of the K2 domain of TFPI with side chains of residues included in the binding epitope represented by balls and sticks. (B) is as A, but with surface added. (C) Binding epitope mapped on to primary sequence. Capital bold, italic and underlined letters corresponds to residues in the K2-binding epitope making contacts with the MuTFPI4F36 Fab heavy chain only (positions 10, 11, 13, 28, 31, 33 and 35), light chain only (positions 21, 23 and 50), and with both heavy and light chain (17, 19, 34 and 36), respectively. Secondary structural elements (h=helix, s=sheet) are indicated (helices at positions 5-8 and 50-56 and sheets at positions 20-26 and 31-37). Residues highlighted grey (positions 1-2 and 59-66) are present in the expressed protein, but are not observed in the crystal structure due to the N- and C-termini being flexible.

The binding epitope on the antigen K2, defined as residues in K2 containing at least one side-chain heavy atom situated within a distance of 4 Å or less from a heavy atom in Fab, comprises residues E10, E11, P13, R17, Y19, T21, Y23, Q28, Q31, E33, R34, F35, K36 and L50 (FIG. 10). The contact residues in K2 are located in L1 (E10, E11, P13, R17, Y19), in the β-sheet structure (T21, Y23, Q31, E33, R34, F35, K36) and the connecting loop, Lβ (Q28) and, finally, a single one in α1 (L50). FIG. 10 depicts the binding epitope mapped on to both the 3D-structure of K2 and the primary amino acid sequence.

Description of the MuTFPI4F36 Paratope

The paratope in the MuTFPI4F36 Fab fragment was determined from the same X-ray structure of the complex between the MuTFPI4F36 Fab and the TFPI K2 domain. The paratope was defined as those residues in the MuTFPI4F36 Fab having a heavy atom within a distance of less than 4 Å from a heavy atom in the K2 domain. The contact residues in the light chain are located at residues E31, S32, D33, Y37, A96, T97, H98 and F99 of SEQ ID NO: 4. The contact residues in the heavy chain are located at residues N31, R53, S54, S56, Y57, Y59, F60, P61, D62, Q65, Y102, D103 and D106 of SEQ ID NO: 8. The location of the paratope is illustrated in FIG. 3.

Example 5

Structure of the K2/HzTFPI4F36 Fab Complex

Figure 11:
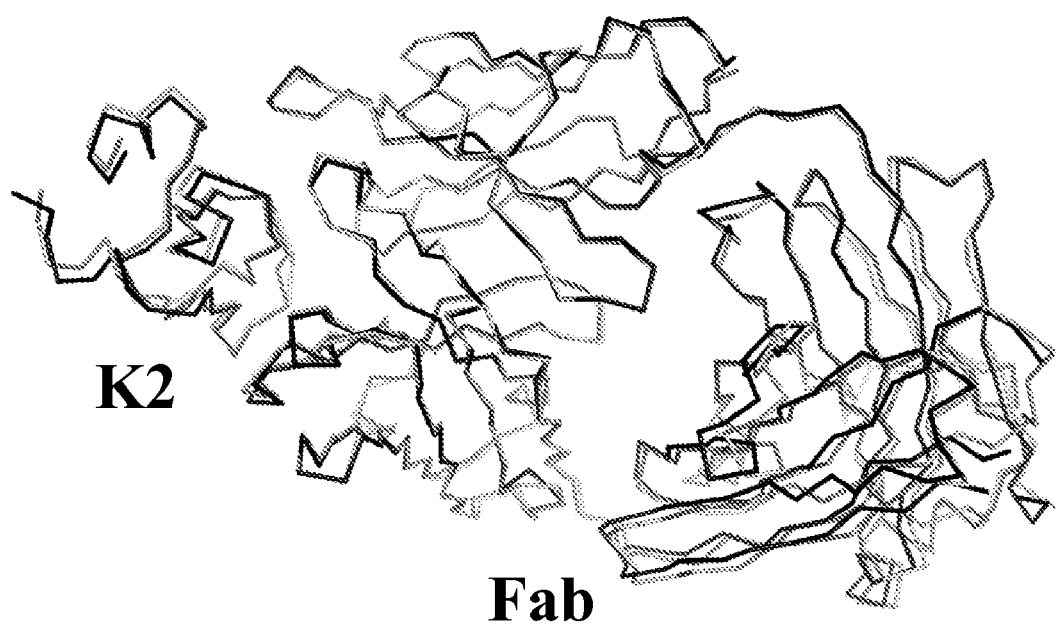
FIG. 11 shows a comparison of the back-bone traces of K2:MuTFPI4F36 Fab and K2:HzTFPI4F36 Fab complexes, demonstrating the identical binding modes for the murine MuTFPI4F36 and humanized HzTFPI4F36 Fab fragments. K2:MuTFPI4F36 Fab is shown in grey and K2:HzTFPI4F36 Fab in black. Structures are superpositioned to optimize the match between the variable region of the Fab fragments.

Using methodology similar to that described for determination of the three-dimensional structure of MuTFPI4F36 Fab bound to K2, the structure of the complex between the Fab fragment from the humanized antibody, HzTFPI4F36, and K2 was determined. The Fab of HzTFPI4F36 was expectedly found to bind to the same region on K2 as the murine Fab from which it is derived. The overall similarity between the structures of the two complexes is evident in FIG. 11, where back bone ribbon traces are overlaid for the K2/TFPI4F36 Fab and K2/HzTFPI4F36 Fab complexes. The epitope (defined using a 4 Å cut-off) on K2 was, for HzTFPI4F36, found to comprise residues E10, E11, D12, P13, R17, Y19, T21, Y23, F24, N26, Q28, Q31, C32, E33, R34, K36 and L50. In comparison with the structure of K2/MuTFPI4F36 Fab of murine origin, D12, F24, N26 and C32 are in the humanized K2/HzTFPI4F36 complex within the 4 Å cut-off, whereas F35 is outside. This reflects minor differences in side chain orientations within the binding interfaces of the K2/MuTFPI4F36 Fab and K2/HzTFPI4F36 Fab complexes, in spite of the fact that the CDR regions in MuTFPI4F36 and HzTFPI4F36 are identical.

Examples 6 to 8

The function of HzTFPI4F36 (mAbTFPI 2021) was compared to the function of all (four) commercially available monoclonal antibodies, some of which are said to bind to the K2 domain of TFPI; some of which have not been described with respect to binding.

Example 6

TFPI Neutralizing Assay: FXa Inhibition

Materials used were BSA buffer in assay (50 mM Hepes; 0.1 M NaCl, 5 mM CaCl2, 0.1 mg/ml BSA, pH 7.4) and the reagents shown in table 5.

min in a Spectramax. 100% activity represents the activity of FXa without addition of TFPI.

TABLE 6

Neutralization of TFPI inhibition of FXa

| Company | mAb ID | IC$_{50}$ nM | % neutralization of TFPI at 150 nM |
|---|---|---|---|
| Current invention | HzTFPI4F36 (mAbTFPI2021) | 12.6 | 100% |
| AbNova | mAb0281 | nd | <10% |
| American Diagnotica | mAb4904 | nd | <10% |
| R&Dsystems | mAb2974 | 29.4 | 90% |
| R&Dsystems | mAb29741 | nd | <10% |

Conclusion:

At 150 nM, HzTFPI4F36 (mAbTFPI 2021) fully neutralized TFPI inhibition of FXa. Almost no activity was detected for mAb0281, mAb4904 and mAb29741.

TABLE 5

Materials used

| Reagent | Company/Reference | Stock conc | Final concentration (dilution in BSA buffer) |
|---|---|---|---|
| Human FXa | Enzyme Research Laboratory | 21.7 µM | 5 nM |
| Human TFPI | Reference: Pedersen et al., 1990, J. Biol. Chem. 265, p. 16786-16793 | Freeze-dried in 10 mM glycylglycine, 100 mM NaCl; 165 mM mannitol buffer pH 7.0. Reconstitute in water. | 6 nM |
| mAbTFPI4F36 | Current invention | | 5-150 nM |
| mAb0281 | Ab systems | | |
| mAb4904 | AD | | |
| mAb2974 | R&D systems | | |
| mAb29741 | R&D systems | | |
| S2765 | Chromogenix | 20 mM | 1 mM |

Method:

Recombinant full length human TFPI (final concentration 6 nM)) was mixed in BSA buffer with increasing concentrations of the mAb of interest (final concentration: 5-150 nM) for 30 min. FXa was added and incubated 30 min with the mixture for another 30 min. Chromogenic substrate S2765 was added and the absorption at 405 nm was measured for 15

Example 7

TFPI Neutralizing Assay: FVIIa/TF/FXa Inhibition

Materials used were BSA buffer (50 mM Hepes; 0.1 M NaCl, 5 mM CaCl$_2$, 0.1 mg/ml BSA, pH 7.4) EDTA: 50 mM and the reagents listed in table 7.

TABLE 7

| Reagent | Company/Reference | Stock Conc | Final concentration (dilute in BSA buffer) |
|---|---|---|---|
| MAB2974 | R&D systems | 3330 nM | Varying (5-150 nM) |
| mAbTFPI4F36 | Current invention | 75300 nM | |
| NovoSeven | Novo Nordisk | 27 µM | 1 pM |
| vesicles | HTI Phospholipids vesicles cat#PCPS-02 #W1115- 75% PC - 25% PS | 2.0 mM | 10 µM |
| S-2765 | Chromogenix | 35 mM | 0.5 mM |
| FX | American Diagnostica inc. Bovine factor X Product no 510 Lot No. 050920 dissolved 50% glycerol/water | 165 µM | 160 nM |
| TFPI | Reference: Pedersen et al., 1990, J. Biol. Chem. 265, p. 16786-16793 | 18.6 µM | 1 nM |
| TF (Innovin) | Dade Behring#2010-01-11#536975 vial diss. in 10 ml H2O | 2.8 nM (6 nM) | 1 pM |

Method:

Add all the components in the final concentrations indicated in the table. Add 25 µl FX, 25 µl TFPI mAb in varying concentrations, 25 µl human TFPI, 25 µl FVIIa-TF (innovin) in microtiter wells. Incubation for 40 min at room temperature. Add 50 µl EDTA followed by 50 µl S-2765. Mix and read the plate for 15 min at 405 nm in Spectra max. 100% activity is the activity of FVIIa/TF/FX obtained with no TFPI present.

TABLE 8

Neutralization of TFPI inhibition of FVIIa/TF/FX

| Company | mAb ID | $IC_{50}$ | % neutralization of TFPI at 150 nM |
|---|---|---|---|
| Current invention | HzTFPI4F36 (mAbTFPI2021) | 3.8 nM | 100% |
| AbNova | mAb0281 | nd | Nd |
| American Diagnotica | mAb4904 | nd | Nd |
| R&Dsystems | mAb2974 | 45.6 nM | 53% |
| R&Dsystems | mAb29741 | nd | Nd |

Conclusion:

At a mAb concentration of 150 nM TFPI is fully neutralised by mAbTFPI2021. mAb2974 also reaches saturation but does not fully neutralize TFPI (53% neutralisation).

Example 8

Binding Interaction Analysis

Materials used were as listed in table 9.

TABLE 9

| Reagent | Company |
|---|---|
| TFPI | Freeze-dried in 10 mM glycylglycine, 100 mM NaCl; 165 mM mannitol buffer pH 7.0. Reconstitute in water. |
| mAbTFPI2021 | Current invention |
| mAb0281 | Ab systems |
| mAb4904 | AD |
| mAb2974 | R&D systems |
| mAb29741 | R&D systems |
| All other reagents | Biacore |

Method:

Binding interaction analysis was obtained by Surface Plasmon Resonance in a Biacore T-100 instrument. Capture of the relevant monoclonal antibody at a fixed concentration was obtained by direct immobilization to a CM5 chip of the mAb to a level of 500-1000 RU in 10 mM sodium acetate pH 4.5-5.0. Four-fold dilutions of recombinant human full length TFPI or human TFPI short form (1-161 amino acid residues) from 200 nM to 0.2 nM were tested for binding to the immobilized mAb. Running and dilution buffer: 10 mM HEPES, 150 mM, 0.005% p20, pH 7.4. Regeneration was obtained by 10 mM Glycine, pH 1.7. Determination of kinetic and binding constants ($k_{on}$, $k_{off}$, $K_D$) was obtained assuming a 1:1 interaction of TFPI and the antibody of interest using the Biacore T100 evaluation software. Results are shown in table 10. Competition of the different mAbs for binding to TFPI when bound to mAbTFPI2021 ("mAb2021", HzTFPI4F36) was obtained by immobilisation of mAbTFPI2021 to 5000 RU at a CM5 chip followed by binding of 50 nM TFPI followed by varying concentrations the mAbs (2974, 0281, 4904, 29741) to be tested for competition. Results are shown in table 11. Regeneration of the chip was obtained by 10 mM Glycine, pH 1.7.

TABLE 10

Surface Plasmon Resonance (SPR) analysis. Binding to full length human TFPI. Kinetic and binding constants.

| Producer | mAb ID | ka (1/Ms) | kd (1/s) | $K_D$ (M) | $K_D$ nM |
|---|---|---|---|---|---|
| Current invention | mAb2021 | 2.39E+06 | 3.58E−05 | 1.50E−11 | 0.015 |
| AbNova | mAb0281 | 3.99E+05 | 0.001436 | 3.60E−09 | 3.60 |
| American Diagnotica | mAb4904 | 1.42E+05 | 00.1294 | 9.14E−09 | 9.14 |
| R&Dsystems | mAb2974 | 1.39E+06 | 0.001202 | 8.64E−10 | 0.864 |
| R&Dsystems | mAb29741 | 9.51E+05 | 0.003165 | 3.33E−09 | 3.33 |

TABLE 11

SPR analysis. Binding constant for binding to full length human TFPI and $TFPI_{161}$(K1 and K2 domains). Competition with mABTFPI 2021.

| Producer | mAb ID | $K_D$ (M) TFPI | $K_D$ (M) $TFPI_{161}$ | Competition with mAB 4F36 |
|---|---|---|---|---|
| Current invention | mAbTFPI2021 | 1.50E−11 | 4.55E−11 | Yes |
| AbNova | mAb0281 | 3.60E−09 | 7.28E−09 | No |
| American Diagnotica | mAb4904 | 9.14E−09 | No binding | No |
| R&Dsystems | mAb2974 | 8.64E−10 | 3.12E−09 | Yes |
| R&Dsystems | mAb29741 | 3.33E−09 | No binding | No |

Conclusion mAbTFPI2021 binds to TFPI with a higher affinity than any of the other mAbs tested ($K_D$ 15 pM). Only mAb2974 competes for binding to same site as mAb TFPI4F36.

Example 9

Neutralization of TFPI on Human Umbilical Vascular Endothelial Cells (HUVECs)

Endothelial cells constitutively express TFPI in a form which is attached to the cell surface via a glycosylphosphatidylinositol (GPI) anchor. GPI-anchored TFPI specifically inhibits TF-mediated activity when TF is expressed on the same cell as TFPI. To demonstrate that HzTFPI4F36 (mAbTFPI2021) neutralizes the inhibition by cell bound TFPI much more efficiently than mAb 2974 we applied human umbilical vascular endothelial cells HUVECs; and in order to induce TF expression, these cells were stimulated with TNFa (Sigma RBI) and IL1β (Roche) prior to testing of FVIIa/TF catalyzed activation of FX.

HUVEC cells were cultivated to confluence in 96 well plates in EBM-2 medium (Clonetics) and stimulated with 20 ng/ml TNFα and 20 ng/ml IL1β for 2 hours prior to testing. Testing was performed in 25 mM HEPES, 137 mM NaCl, 3.5 mM KCl, 5 mM CaCl, 1 mg/ml BSA (0.1%) ph 7.4, and FX activation was followed in the presence of antibody (0-20 nM) and with addition of 50 pM FVIIa and 50 nM FX. Generation of FXa was measured with 0.6 mM of a chromogenic substrate, S-2765 (Chromogenix) and calibrated towards a FXa standard curve.

Figure 12:
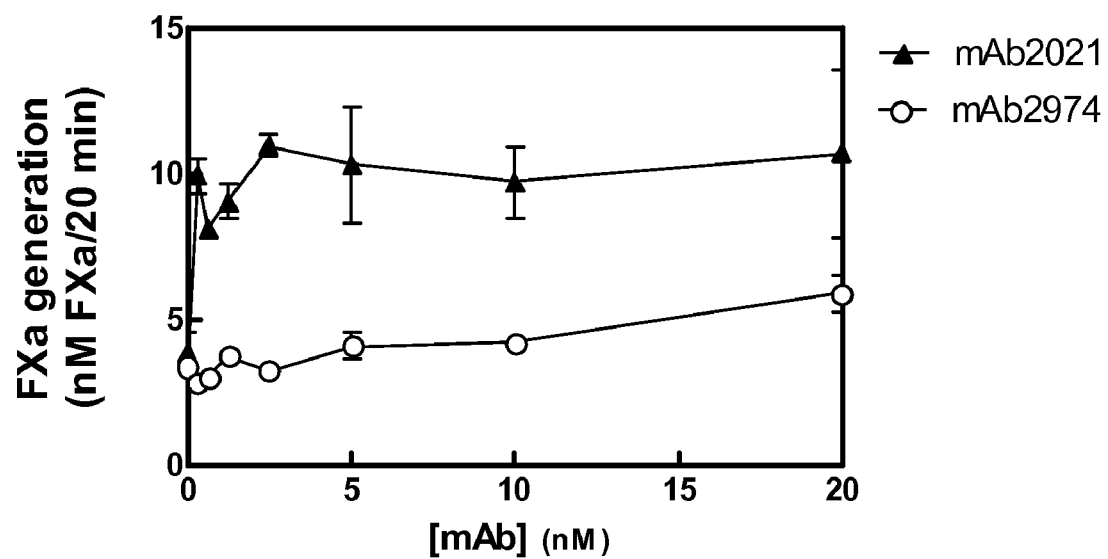
FIG. 12 shows the effect of anti-TFPI monoclonal antibodies (mAbs) on TF/FVIIa-induced activation of FX on the surface of HUVECs stimulated with TNFα/IL1β. Activation of FX was measured in the presence of 0-20 nM mAB (mAbTFPI 2021 or mAb 2974), 50 pM FVIIa (NovoSeven®) and 50 nM FX in buffer with 25 mM HEPES, 137 mM NaCl, 3.5 mM KCl, 5 mM $CaCl_2$, 1 mg/ml BSA (0.1%) pH 7.4 which was overlaid a monolayer of HUVECs. Generated FXa activity was determined in an amidolytic assay with S-2765 measured by the increase in absorbance at 405 nM.

FIG. 12 shows the results when the inhibition by cell bound TFPI was abolished by 0-20 nM of HzTFPI4F36 or mAb 2974. TF/FVIIa-mediated activation of FX was stimulated by HzTFPI4F36 with a half maximal effect concentration, (EC50~nM) whereas hardly any stimulation of FXa generation was observed with the 2974 mAb at 20 nM.

Thus, this example illustrates that HzTFPI4F36, contrary to mAb 2974, efficiently neutralizes inhibition of TF/FVIIa-mediated FX activation by cell bound TFPI.

Example 10

Neutralization of TFPI Inhibition of TF/FVIIa Activity om MDA-MB 231 Human Breast Carcinoma Cells MDA-MB 231 cells constitutively express high levels of TF and insignificant amounts of TFPI on the surface. Cell surface TF/FVIIa mediated activation of FX can be inhibited by exogenous added TFPI. To demonstrate that HzTFPI4F36 neutralizes this type of TFPI inhibition much more efficiently than mAb 2974 we applied MDA-MB 231 cells and tested the ability of various concentrations of antibody to abolish the TFPI inhibition of FVIIa/TF catalyzed activation of FX.

MDA-MB 231 cells were cultivated to confluence in 96 well plates in DMEM Gibco cat #31966-021 supplied with 10% FCS and 1% P/S. Testing was performed in 25 mM HEPES, 137 mM NaCl, 3.5 mM KCl, 5 mM CaCl, 1 mg/ml BSA (0.1%) ph 7.4, and FX activation was followed in the presence of antibody (0-20 nM) and with addition of 2.5 nM full length human recombinant TFPI, 100 pM FVIIa and 50 nM FX. Generation of FXa was measured with 0.6 mM of a chromogenic substrate, S-2765 (Chromogenix). The absorbance at 405 nm was measured continuously and the FXa activity was determined by measuring the slope of the progress curve at 15 min after initiation of the reaction.

Figure 13:
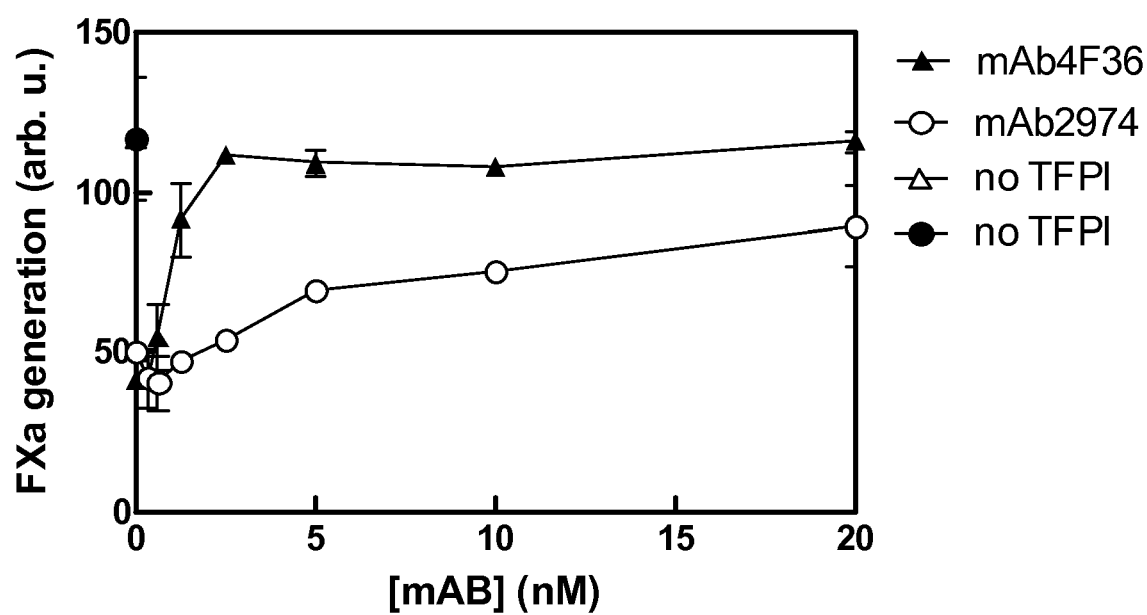
FIG. 13 shows the effect of anti-TFPI mAbs on TFPI inhibition of TF/FVIIa-induced activation of FX on the surface of MDA-MB 231 cells. Activation of FX was measured in the presence of 0-20 nM mAb (Hz mAbTFPI 2021 or mAb 2974), 2.5 nM fl-TFPI, 100 pM FVIIa and 50 nM FX in buffer with 25 mM HEPES, 137 mM NaCl, 3.5 mM KCl, 5 mM CaCl, 1 mg/ml BSA (0.1%) pH 7.4 which was overlaid a monolayer of MDA-MB 231 cells. Generated FXa activity was determined in an amidolytic assay with S-2765 measured by the increase in absorbance at 405 nM.
Figure 14:
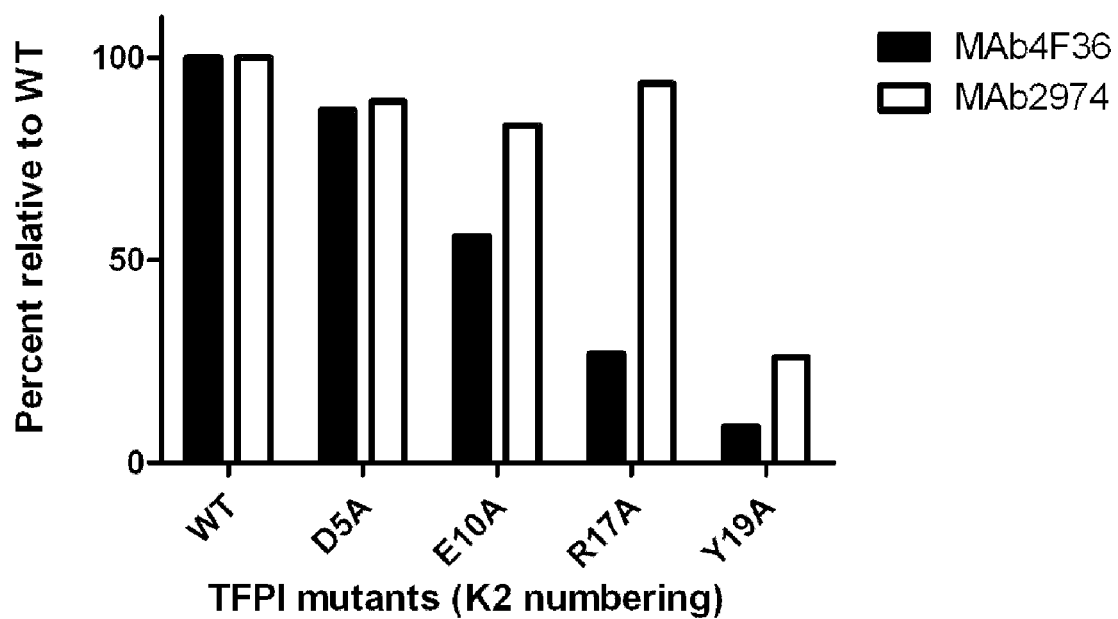
FIG. 14 shows the effect of single amino acid alanine substitutions of select residues within the TFPI Kunitz 2 domain on binding to mAbTFPI 2021 ("mAb4F36") and mAb2974 (n=2). The selected residues are part of the mABTor 10 days before induction of bleeding. The bleeding was observed for 1 hour (3600 sec).
Figure 15:
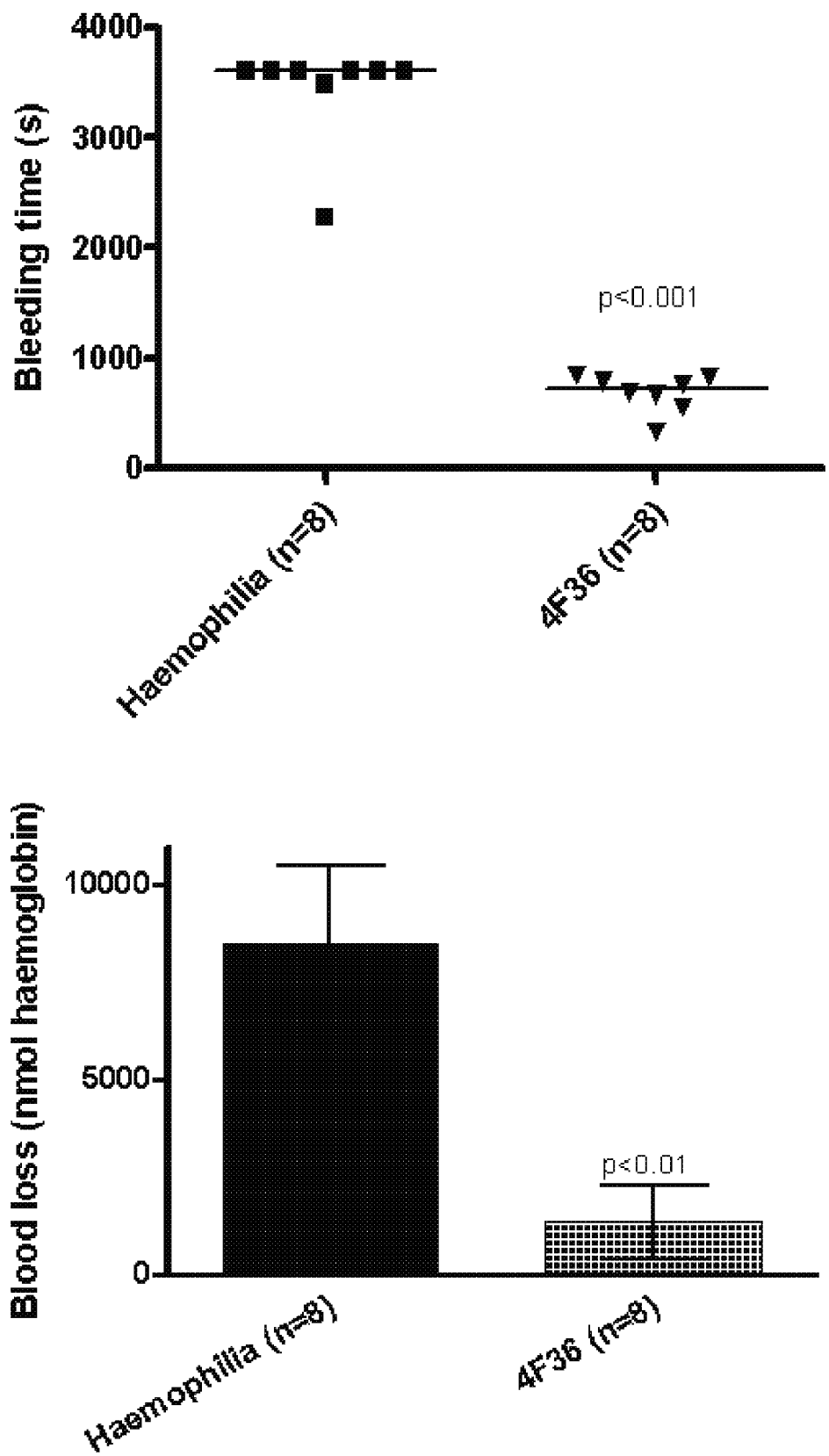
Figure 16:
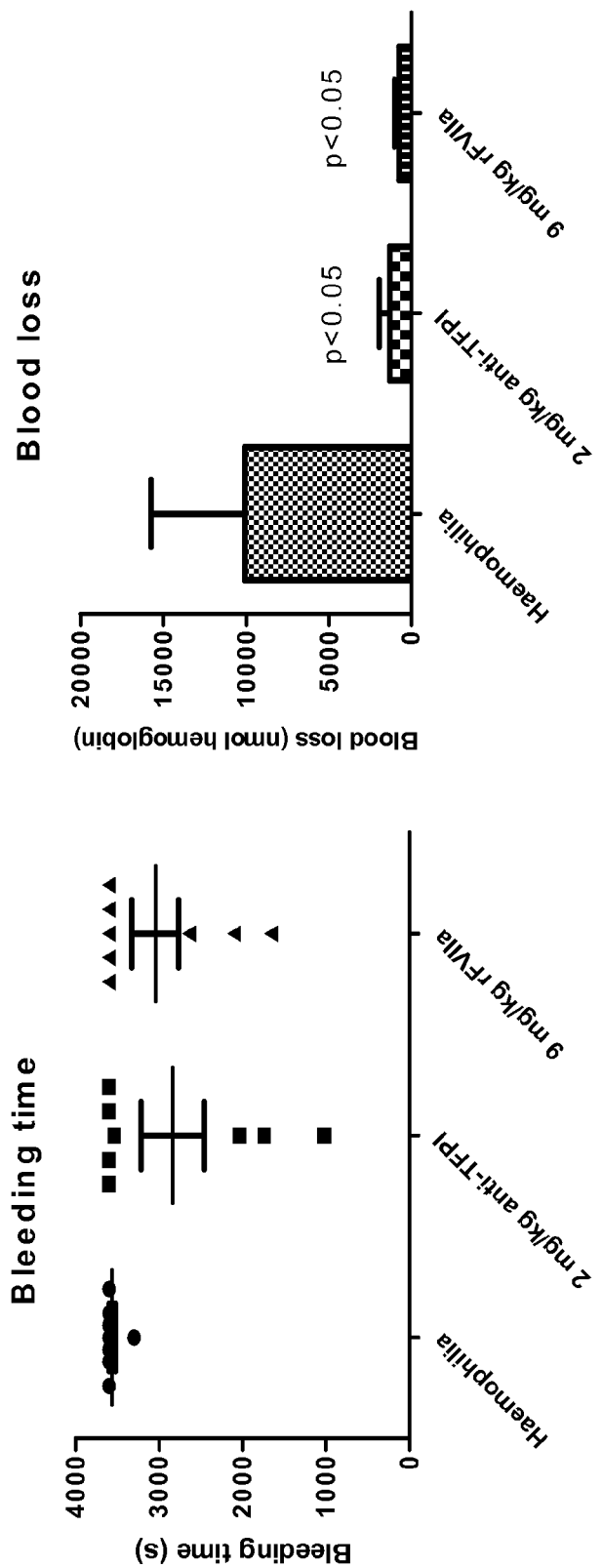
Figure 17:
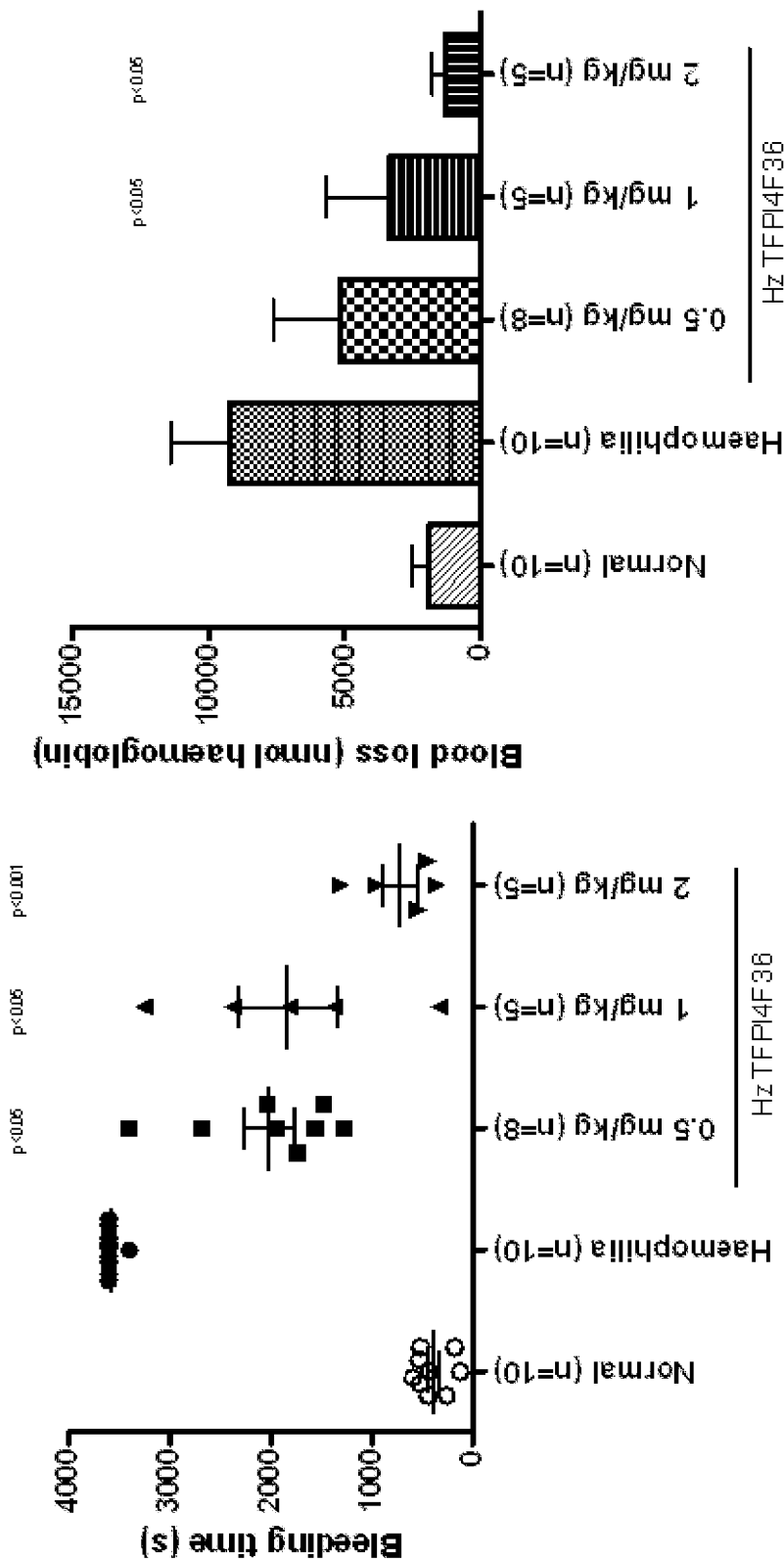
Figure 18:
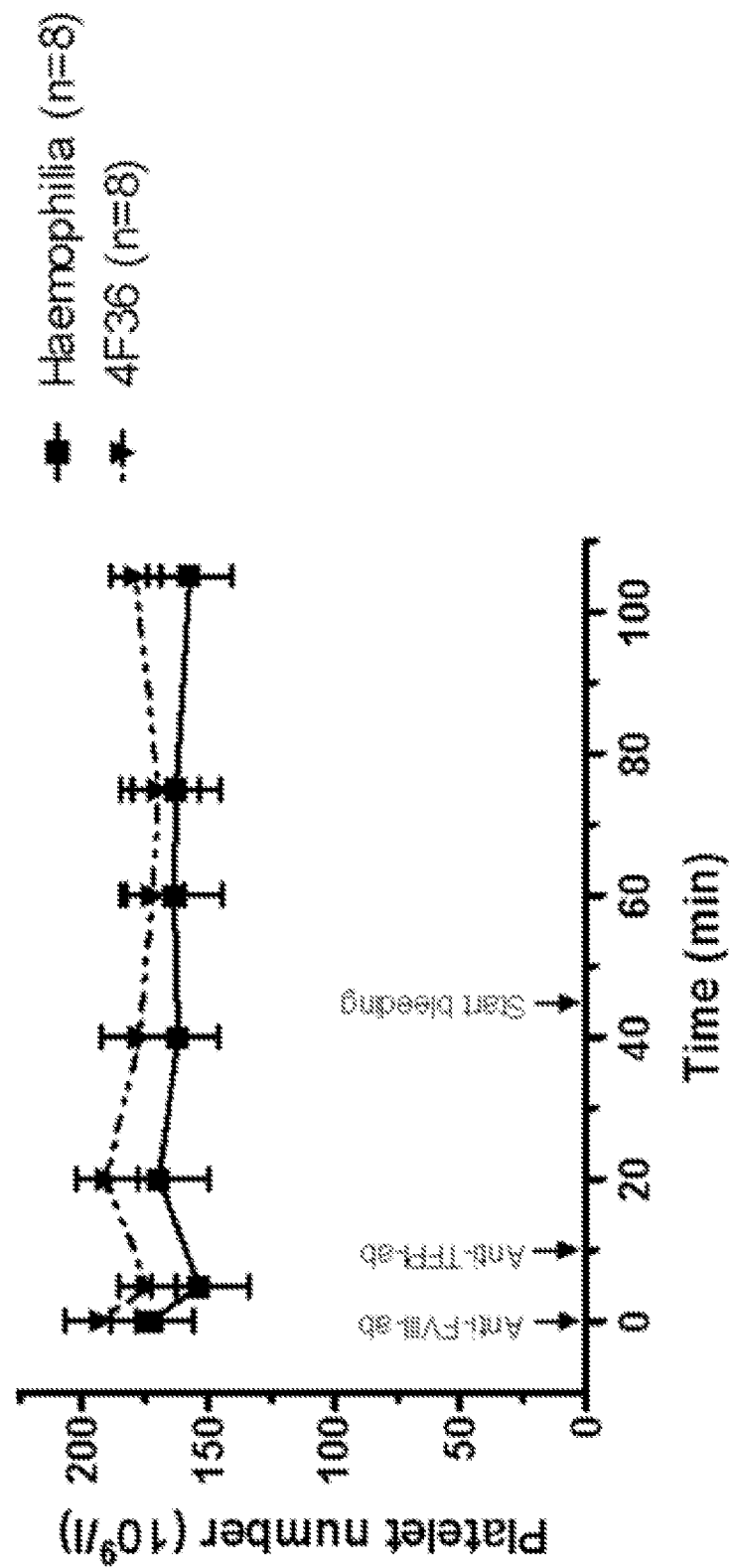

FIG. 13 shows the results when the inhibition by TFPI was abolished by 0-20 nM of HzTFPI4F36 or mAb 2974. TF/FVIIa-mediated activation of FX was stimulated by HzTFPI4F36 with a half maximal effect concentration, ($EC_{50}$~2 nM) whereas stimulation of FXa generation was obtained at a substantially higher concentration of the 2974 mAb ($EC_{50}$>20 nM).

Example 11

Figure 19:
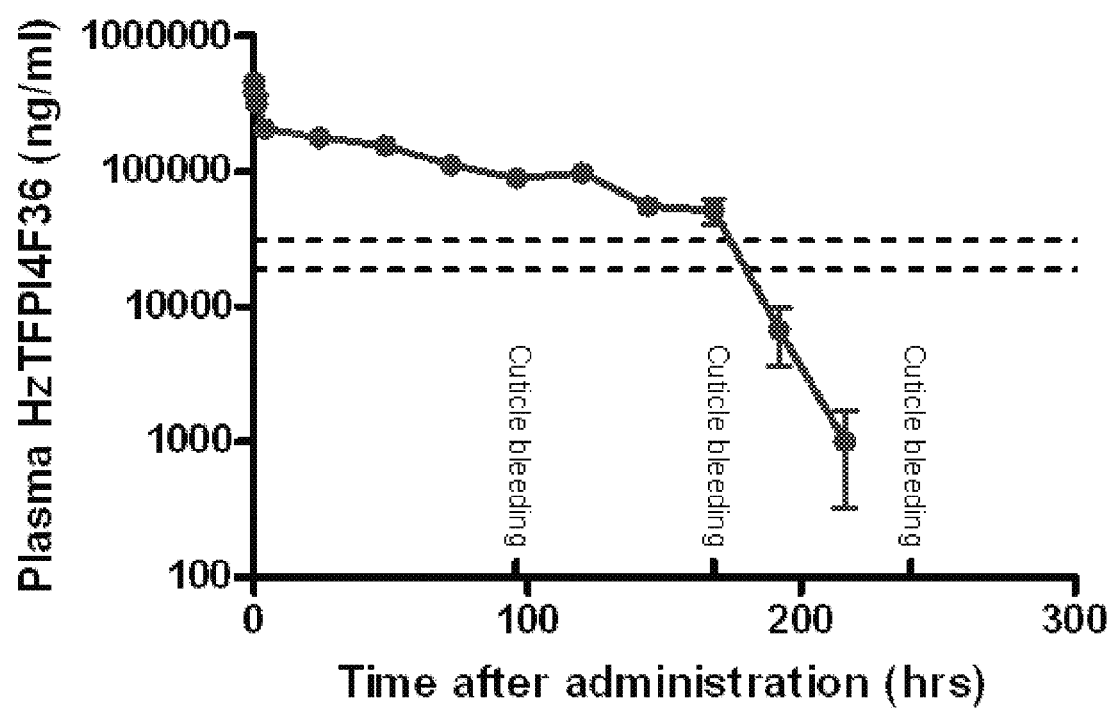

Mapping the Binding Epitopes of the anti-TFPI Monoclonal Antibodies, HzTFPI4F36 and mAb2974, Using ELISA The binding epitope for HzTFPI4F36 on TFPI Kunitz-domain 2 (K2) has been mapped by solving the crystal structure of the TFPI-K2/HzTFPI4F36 complex. The effect of mutating single amino acid residues in TFPI within (E10, R17 and Y19) and outside (D5) the binding epitope for HzTFPI4F36 on the binding affinity to HzTFPI4F36 and mAb2974 (R&Dsystems) was analyzed by ELISA. The TFPI variants were expressed in HEK293-F cells and the ELISAs were carried out using the conditioned medium from the cell cultures.

The concentrations of TFPI-WT and TFPI mutants were estimated by an ELISA, which bind TFPI K1 (MAb4903, American Diagnostica) and K3 (MAb4F110, in-house) and hence is not affected by the mutations. The effect of the mutations on binding to HzTFPI4F36 was analyzed using MAb4903 and HzTFPI4F36 in the ELISA. The effect on MAb2974 binding was determined using an ELISA with MAb2974 and MAb4F110.

The effects of the mutations in TFPI-Kunitz 2 on binding to HzTFPI4F36 and MAb2974 respectively, were calculated relative to TFPI-WT (100% binding) and illustrated in FIG. 14. The numbers have been corrected for differences in expression levels.

Conclusion:

Alanine mutation of the three amino acid residues within the binding epitope for HzTFPI4F36 resulted in reduced binding to HzTFPI4F36, whereas alanine substitution of the residue located outside the epitope (TFPI-D5A) had no effect. Only one of the four alanine mutants, TFPI-Y19A, had reduced binding to MAb2974.

In conclusion, HzTFPI4F36 and MAb2974 have distinct but overlapping binding epitopes located on TFPI-Kunitz 2.

Example 12

In vivo Studies

Rabbits were made transiently haemophilic by intravenous administration of 2000 RBU/kg of monoclonal anti-FVIII-antibodies. After 10 minutes, the rabbits received 12000 U/kg of anti-TFPI-antibody (4F36; 1.93 mg/kg). Cuticle bleeding was induced 45 minutes after anti-FVIII-antibody administration.

The 4F36 antibody caused a significant reduction in cuticle bleeding time (FIG. 15). Administration of the 4F36 antibody led to no significant drop in platelet number (FIG. 18).

A similar experiment was repeated in which three groups of eight transiently haemophilic rabbits received either isotype control antibody (negative control group), 2 mg/kg anti-TFPI (mAb 4F36) or 9 mg/kg NovoSeven (positive control group) 5 minutes after cuticle bleeding was induced. Results are illustrated in FIG. 16: administration of mAB 4F36 resulted in a considerable reduction in blood loss (approximately 85%) in all recipients, demonstrating that mAb4F36 can be used "on demand".

Example 13

Estimation of Dose-Effect Relationship in Rabbit

The dose-effect relationship of the humanized mAb HzTFPI4F36 was examined in a rabbit haemophilia model. Rabbits were made transient haemophilic by iv administration of a monoclonal anti-FVIII-antibody. After 10 minutes, the rabbits received 0.5, 1, 2 mg/kg HzTFPI4F36 or an isotype control antibody. After another 35 minutes cuticle bleeding was induced, followed by a 60 minutes observation period. HzTFPI4F36 significantly and dose-dependently reduced bleeding time as well as blood loss when increasing the dose from 0.5 to 2 mg/kg (FIG. 17). Thus, a significant reduction of both bleeding time and blood loss was achieved with 1 mg/kg HzTFPI4F36, corresponding to a plasma concentration of 18780 ng/ml HzTFPI4F36. Normalization of the bleeding was achieved at 2 mg/kg, corresponding to a plasma concentration of 30980 ng/ml HzTFPI4F36.

These data indicate that the 'efficacious concentration', e.g. the plasma concentration needed for normalization in the present model—of HzTFPI4F36 is in the range of 18780 and 30980 ng/ml.

Example 14

PK/PD in Rabbits—'Duration of Action'

A pharmacokinetic study of HzTFPI4F36 in rabbits dosed with 20 mg/kg was performed. At predetermined time-points during the study blood samples were drawn from the rabbits for pharmacokinetic profiling by an ELISA measuring free HzTFPI4F36 (shown in FIG. 3 below). Effect studies were performed at 4 days (96 hours), 7 days (168 hours) and 10 days (240 hours) after administration, using the cuticle bleeding model in transient haemophilic rabbits, the effect time points are indicated in FIG. 19.

The pharmacokinetic profile is biphasic indicative of target mediated clearance. Thus, above the bend of the curve excess free mAb is present ($mAB_{free} > TFPI_{total}$), below the bend: $mAb_{free} < TFPI_{total}$. In good accordance with the pharmacokinetic profile, both bleeding time and blood loss was significantly reduced both at 4 and 7 days after administration of 20 mg/kg HzTFPI4F36 intravenously, whereas no significant effect was observed after 10 days (FIG. 20).

These data confirm that the efficacious plasma concentration of HzTFPI4F36 in a cuticle bleeding model in haemophilic rabbits is between 18780 and 30980 ng/ml which is close to the TFPI saturation limit (curve bend). Accordingly, a single iv. dose of 20 mg/kg HzTFPI4F36 reduced cuticle bleeding for at least 7 days, which corresponded to the period of time the plasma concentration was above the 'efficacious concentration'

Example 15

Pharmacokinetic Model Based on Monkey PK Data

Figure 21:
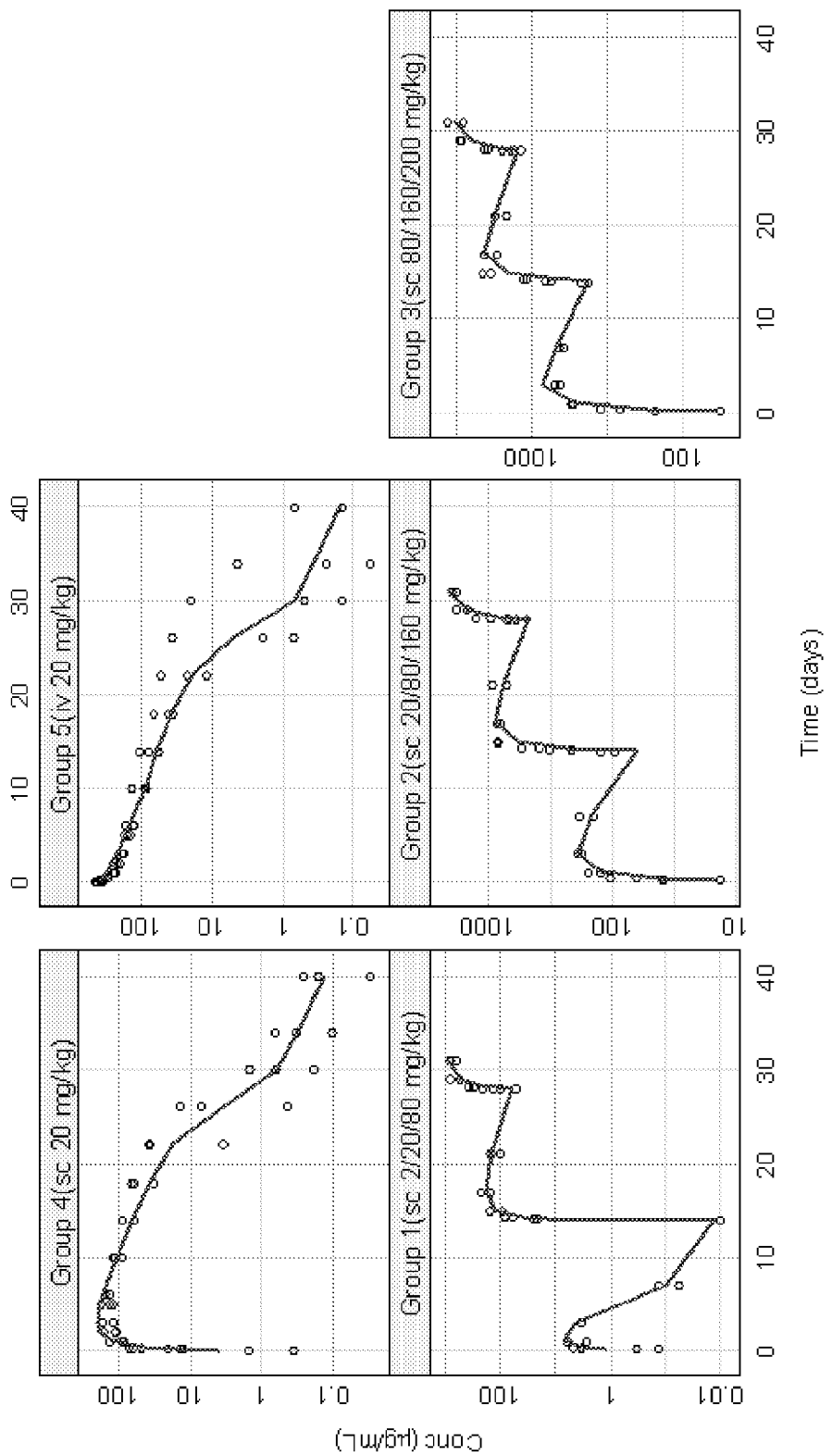
FIG. 21 shows the plasma concentration levels after IV and SC HzTFPI4F36 (mAbTFPI 2021) administration to monkeys. On the three lower plots two monkeys were administered three doses of HzTFPI4F36 with two weeks interval. On the lower left three doses of 2, 20 and 80 mg/kg were administered, on the lower middle three doses of 20, 80 and 160 mg/kg were administered; on the lower right three doses of 80, 160 and 200 mg/kg were dosed. On the upper left a single dose of 20 mg/kg were administered to three monkeys; on the upper right as single IV dose were administered to three monkeys. On plots the points represent individual observations whereas the line represents the model fit.

A pharmacokinetic evaluation was made based on a pharmacokinetic study in monkeys, where both single and multiple doses were administered (FIG. 21). Dose levels ranged from 2 to 200 mg/kg.

The PK profile in monkey (20 mgs/kg, upper panel) is similar to rabbit indicating the presence of similar distribution of soluble and endothelium bound TFPI. Thus, these data indicate that rabbit effect data may be employed to predict the effect range in monkey. Furthermore, the affinity of HzTFPI4F36 for human, monkey and rabbit TFPI are similar (same epitope) and similar TFPI tissue distribution in the three species allows for dose predictions in monkey and man.

Example 16

Simulations

Figure 22:
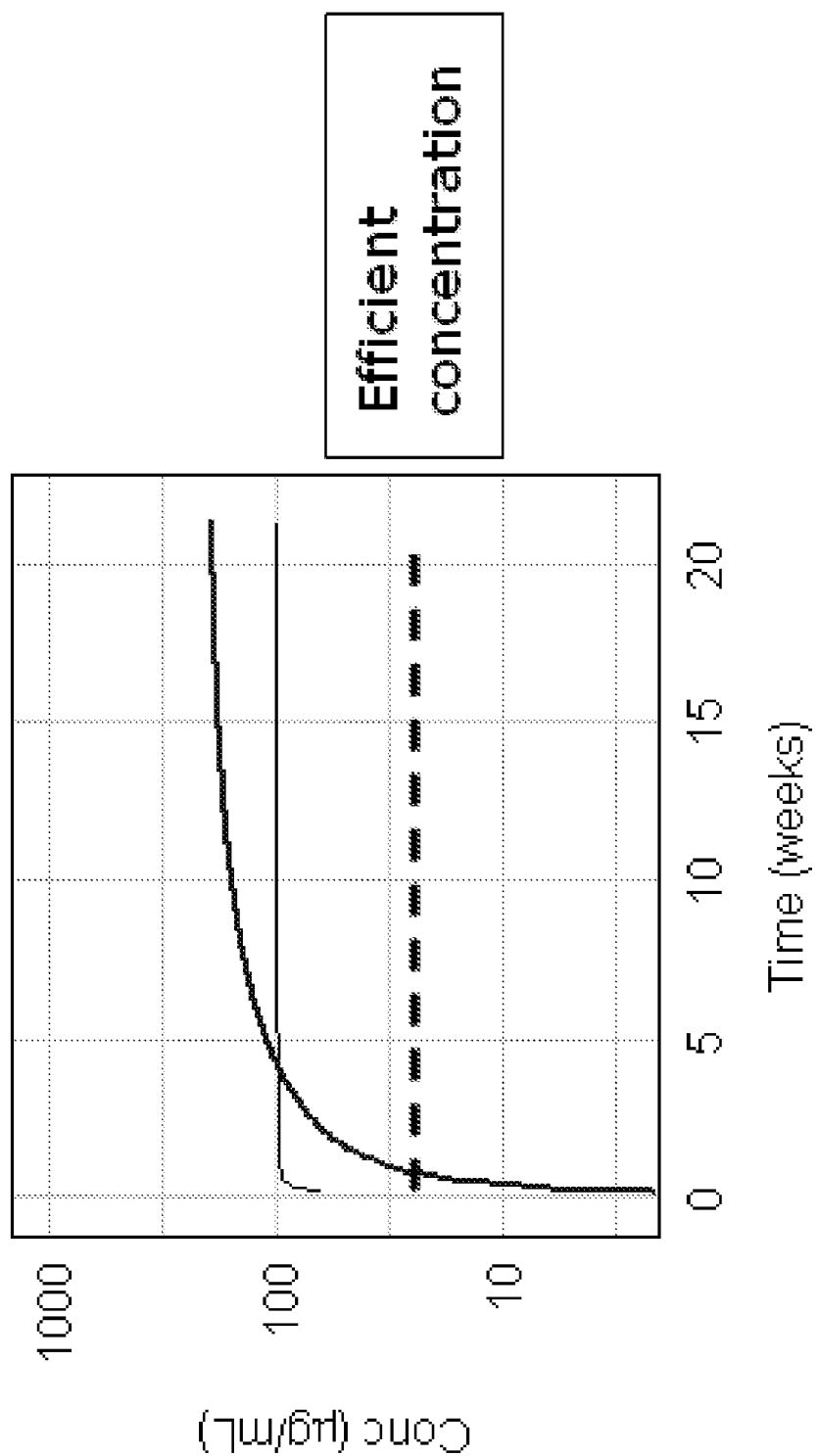
FIG. 22 shows a simulation of 1 mg/kg HzTFPI4F36 (mAbTFPI 2021) administered SC daily. The solid horizontal line represents simulated plasma concentration levels and the dotted horizontal line the upper efficacious concentration as deduced from the effect data.
Figure 23:
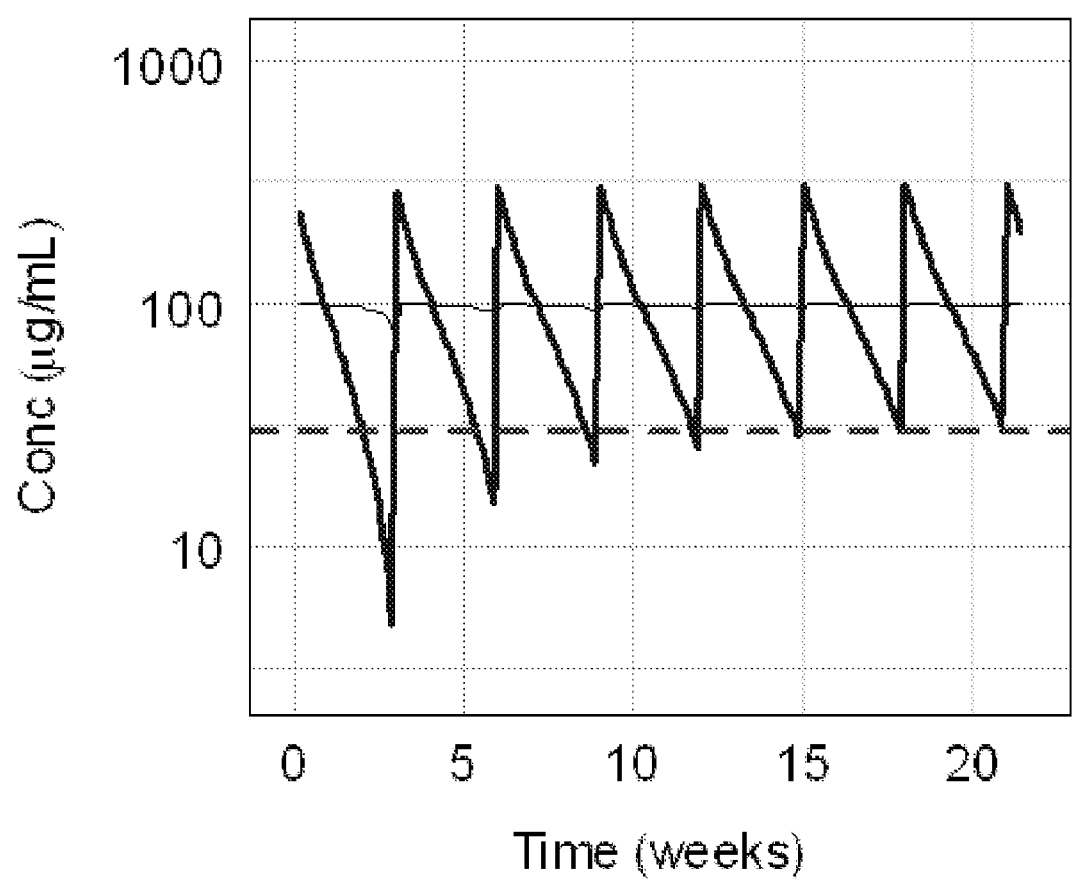
FIG. 23 shows a simulation of 15 mg/kg HzTFPI4F36 (mAbTFPI 2021), administered intravenously every third week. The solid horizontal line represents simulated plasma concentration levels and the dotted horizontal line the upper efficacious concentration as deduced from the effect data.
Figure 24:
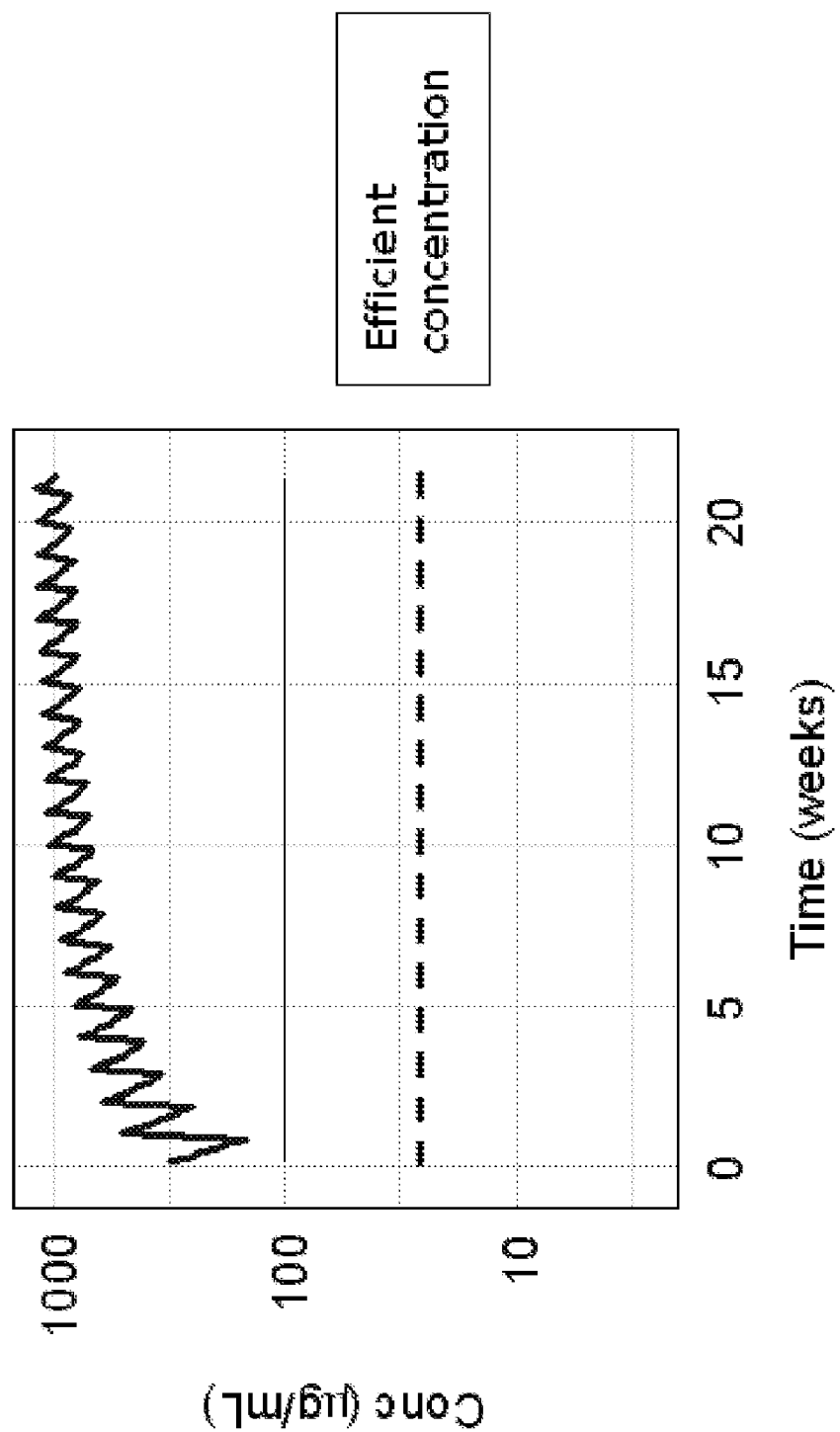
FIG. 24 shows a simulation of 20 mg/kg HzTFPI4F36 (mAbTFPI 2021), administered intravenously every second week. The horizontal solid line represents simulated plasma concentration levels and the horizontal dotted line the expected target saturation as deduced from the effect study.

Based on the model presented above, it was possible to make a series of simulations. The main objective of the simulations was to describe the optimal dosing regimen in a multiple dose setting. The target (TFPI) concentration was not known, but the rabbit effect data above allows for the assumption that if the target is near saturation at a level of 30000 ng/ml then full effect in a bleeding model is obtained. Therefore, the main objective of the simulations was to evaluate which dose levels over a period of time would lead to full saturation. FIG. 22 displays a simulation of 1 mg/kg administered subcutaneously. FIG. 23 shows a simulation of 15 mg/kg HzTFPI4F36 (mAbTFPI 2021) administered IV every third week. FIG. 24 shows a simulation of 20 mg/kg HzTFPI4F36 (mAbTFPI 2021) administered IV every second week.

In summary, based on the above simulations the following dose regimen prediction can be made for human beings:

TABLE 12

| | Dose regimen | |
|---|---|---|
| Type of dose | Dose | Dose regimen |
| S.c. adm | 1 mg/kg | Every $2^{nd}$ day |
| I.v. adm | 10-20 mg/kg | Every $2^{nd}$-$4^{th}$ week |

The invention claimed is:

1. A monoclonal antibody that is capable of binding the Kunitz 2 (K2) domain of tissue factor pathway inhibitor (TFPI), wherein the heavy chain of said antibody comprises:
   a CDR1 sequence of amino acids 31 to 35 (NYAMS) of SEQ ID NO: 18 and
   a CDR2 sequence of amino acids 50 to 66 (TISRSGSYSYFPDSVQG) of SEQ ID NO: 18 and
   a CDR3 sequence of amino acids 99 to 110 (LGGYDEGDAMDS) of SEQ ID NO: 18 and wherein the light chain of said antibody comprises:
   a CDR1 sequence of amino acids 24 to 39 (KSSQSLLESDGKTYLN) of SEQ ID NO: 15; and
   a CDR2 sequence of amino acids 55 to 61 (LVSILDS) of SEQ ID NO: 15; and
   a CDR3 sequence of amino acids 94 to 102 (LQATHFPQT) of SEQ ID NO: 15.

2. A monoclonal antibody according to claim 1, wherein a light chain of said antibody comprises SEQ ID NO: 15 and a heavy chain of said antibody comprises SEQ ID NO: 18.

3. A pharmaceutical composition comprising an antibody according to claim 1 and a pharmaceutically acceptable carrier or diluent.

4. A pharmaceutical composition comprising an antibody according to claim 2 and a pharmaceutically acceptable carrier or diluent.

* * * * *